(12) United States Patent
Coverley

(10) Patent No.: US 9,541,555 B2
(45) Date of Patent: Jan. 10, 2017

(54) REPLICATION PROTEIN

(71) Applicant: Cizzle Biotechnology Limited, York (GB)

(72) Inventor: Dawn Coverley, York (GB)

(73) Assignee: Cizzle Biotech Limited, York (GB)

( * ) Notice: Subject to any disclaimer, the term of this patent is extended or adjusted under 35 U.S.C. 154(b) by 0 days.

(21) Appl. No.: 14/615,045

(22) Filed: Feb. 5, 2015

(65) Prior Publication Data

US 2016/0011200 A1    Jan. 14, 2016

Related U.S. Application Data

(63) Continuation of application No. 12/888,238, filed on Sep. 22, 2010, now abandoned, which is a continuation of application No. 10/537,228, filed as application No. PCT/GB03/05334 on Dec. 5, 2003, now Pat. No. 7,833,702.

(60) Provisional application No. 60/433,925, filed on Dec. 17, 2002.

(30) Foreign Application Priority Data

Dec. 5, 2002    (GB) .................................. 0228337.2

(51) Int. Cl.
*C12Q 1/68* (2006.01)
*G01N 33/574* (2006.01)
*C07K 14/47* (2006.01)

(52) U.S. Cl.
CPC ..... *G01N 33/57496* (2013.01); *C07K 14/4702* (2013.01); *C12Q 1/6883* (2013.01); *G01N 33/5743* (2013.01); *G01N 33/57407* (2013.01); *G01N 33/57426* (2013.01); *G01N 33/57438* (2013.01); *C12Q 2600/158* (2013.01); *G01N 2333/47* (2013.01)

(58) Field of Classification Search
None
See application file for complete search history.

(56) References Cited

U.S. PATENT DOCUMENTS 7,833,702 B2 * 11/2010 Coverley ........... C07K 14/4702
435/6.14

* cited by examiner

*Primary Examiner* — Jim Ketter
(74) *Attorney, Agent, or Firm* — Grimes & Yvon LLP

(57) ABSTRACT

This invention relates to a screening method for the identification of agents which modulate the activity of a DNA replication protein as a target for intervention in cancer therapy and includes agents which modulate said activity. The invention also relates to the use of the DNA replication protein, and its RNA transcripts in the prognosis and diagnosis of proliferative disease e.g., cancer.

13 Claims, 42 Drawing Sheets

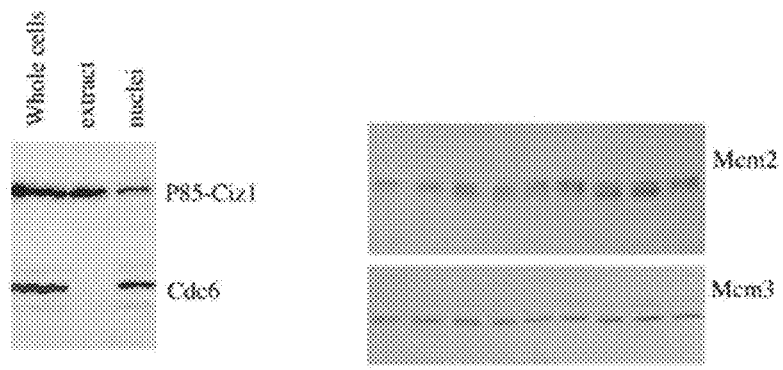
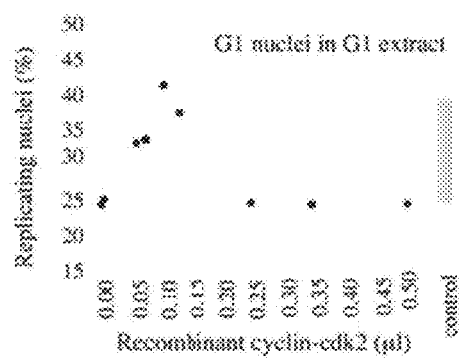
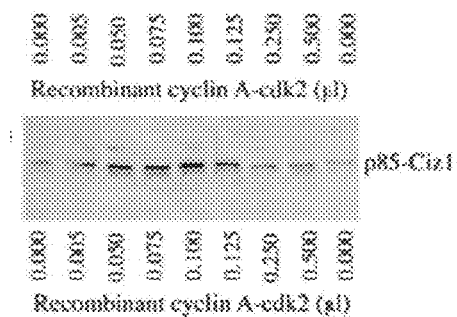
Fig. 1A
Fig. 1C
Fig. 1B
Fig. 1D

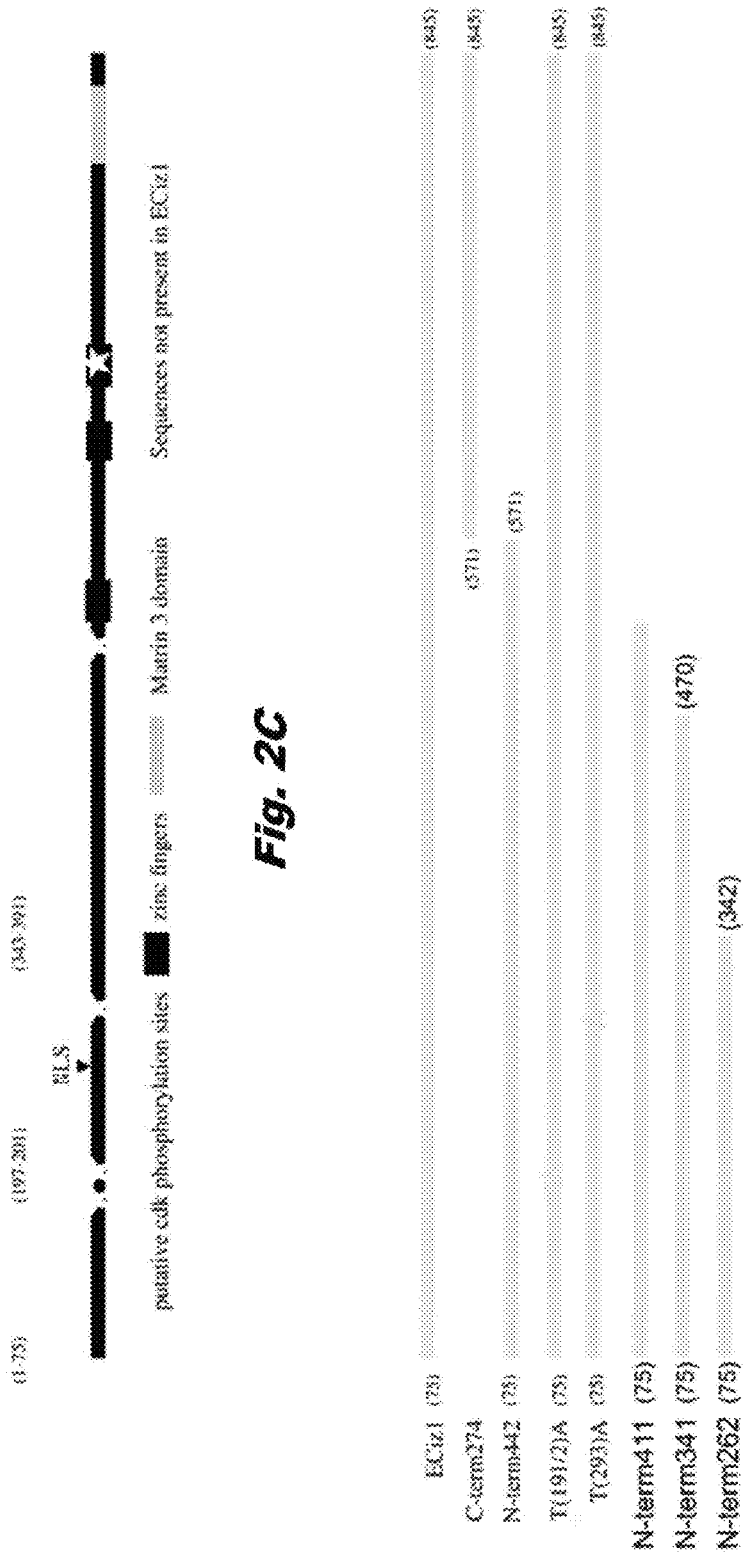

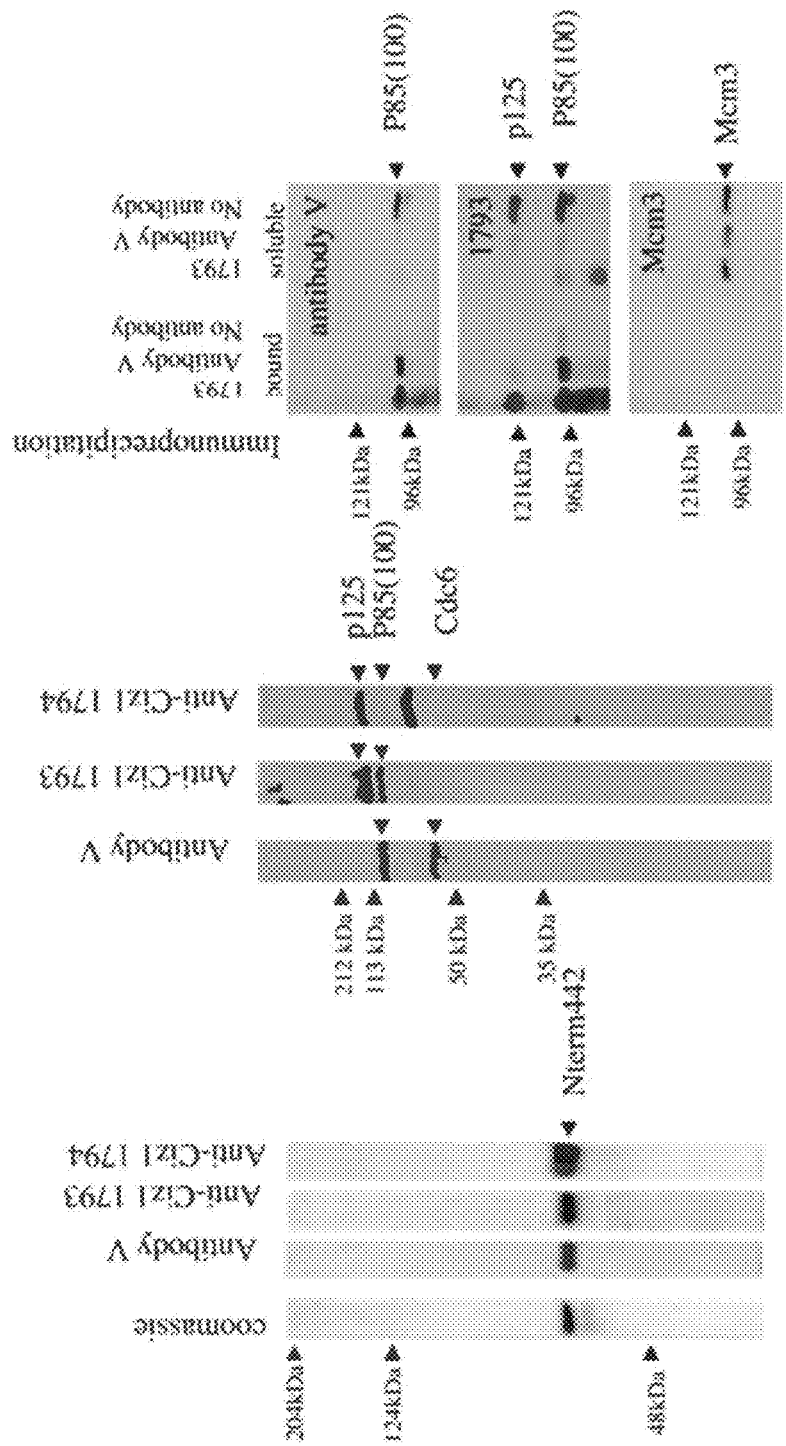

Summary of PCR products

|  | 1 | 2 | 3 | 4 | 5 | 6 | N1 | N2 | 293 |
|---|---|---|---|---|---|---|---|---|---|
| 'DSSSQ' | 0 | 0 | 0 | 0 | 2 | 0 | 1 | 2 | 0 |
| 'exon4' | 1* | 0 | 1* | 3 | 0 | 3 | 1 | 0 | 0 |
| 'FL' | 4 | 1 | 5 | 2 | 2 | 3 | 8 | 3 | 4 |
| other | 0 | 0 | 0 | 1 | 0 | 0 | 1 | 0 | 0 |

ESFTs  
DSSSQ 2/26  
Exon4 8/26

Neuroblastomas  
DSSSQ 3/16  
Exon4 1/16

Examples of PCR products

Ewings 6

Neuroblastoma 2

HEK293

*Fig. 12B*

CATGTTCAAC CTGCAACTCC AGCAGCAGCA ACAGTTGCAG CAGCAGCAGC
AACAGTTGCA GCAGCAGCTC CAGCAGCAGC AGCTCCAGCA GCAGCAACAG
CAGATACTGC AGCTCCAACA GCTGCTGCAA CAGTCTCCAC CACAGGCCTC
CTTGTCCATT CCTGTCAGCC GGGGCCTCCC CCAGCAGTCA TCCCCGCAAC
AGCTTCTGAG TCTCCAGGGC CTCCACTGGA CCTCCCTGCT CAATGCCCC
ATGCTGCAAA GAGCTTTGCT CCTACAGCAG TTGCAAGGAC TGGACCAGTT
TGCAATGCCA CCAGCCACGT ATGACGGTGC CAGCCTCACC ATGCCTACGG
CAACACTGGG TAACCTCCGT GCTTTCAATG TGACAGCCCC AAGCCTAGCA
GCTCCCAGCC TTACACCACC CCAGATGGTC ACCCCAAATC TGCACCAGTT
CTTTCCCCAG GCTACTGAC AGTCTCTGCT GGGGCCTCCT CCTGTTGGGG
TCCCAATAAA CCCTTCTCAG CTCAACCACT CAGGGAGGAA CACCCAGAAA
CAGGCCAGAA CCCCTCTTC CACCACCCCC AATCGCAAGG ATTCTTCTTC
TCAGACGGTG CCTCTGGAAG ACAGGGAAGA CCCCACAGAG GGGCCTGAGG
AAGCCACGGA GCTCCAGATG GACACATGTG AAGACCAAGA TTCACTAGTC
GGTCCAGATA GCATGCTGAG TGAGCCCCAA GTGCCTGAGC CTGAGCCCTT
TGAGACATTG GAACCACCAG CCAAGAGGTG CAGGAGCTCA GAGGAGTCCA
CCGAGAAAGG CCCTACAGGG CAGCCACAAG CAAGGGTCCA GCCCAGACC
CAGATGACAG CACCAAAGCA GACACAGACC CCTGATCGGC TGCCTGAGCC
ACCAGAAGTC CAAATGCTGC CGCGTATCCA GCCACAGGCA CTGCAGATCC
AGACCCAGCC AAAGCTGCTG AGGCAGGCAC AGACACAGAC CTCTCCAGAG
CACTTAGCGC CCCAGCAGGA TCAGGTAGAG CCACAGGTAC CATCACAGCC
CCCATGCCAG TTGCAGCCAC GGGAGACAGA CCCACCTGAAC CAACCTCAGG
CACAGACCCA GCCTCAGCCC CTCTGGCAGG TGCAGTCACA GAAGCAGGCC
CAGACACAGG CACATCCACA GGTACCCACC CAAGCACAGT CACAGGAGCA
GACATCAGAG AAGACCCAGG ACCAGCCTCA GACCTGGCCA CAGGGGTCAG
TACTCCACC AGAACAAGCG TCAGGTCCAG CCTGTGCCAC GGAATCACAG
CTATCCTCTC ACGCTGCAGA AGCTGGGAGT GACCCAGACA AGGCCTTGCC
AGAACCAGTA AGTGCTCAGA GCAGTGAAGA CAGGAGCGG GAGCCGTCCG
CTGGTGGCCT GGATTGGGA GAATGTGAAA AGAGAGCGGG AGAGATGCTG
GGGATGTGGG GGGCTGGGAG CTCCCTGAAG GTCACCATCC TGCAGAGTAG
CAACAGCCGG GCCTTTAACA CCCACACCTCT CACATCTGGA CCTCCCCTG
GGGACTCTAC CTCTGCCACC CCTGCCATTG CCAGCACACC CTCCAAGCAA
AGCCTCCAGT TCTTCTGCTA CATCTGCAAG GCCAGCAGCA GCAGCAGCA
GGAGTTCCAG GATCACATGT CAGAGGCTCA GCACCAACAG CGGCTTGGGG
AAATACAACA CTCGAGCCAG ACCTGCCTGC TGTCCCTGCT GCCCATGCCT
CGGGACATCC TGGAGAAAGA AGCTGGAAGAT CCTCCCCCA AACGCTGGTG
CAACACCTGC CAGGTGTACT ACGTGGGAGA CTTGATCCAG CACCGTAGGA
CACAGGAGCA CAAGGTTGCC AAACAATCCC TGAGGCCCTT CTGCACCATA
TGCAACCGT ACTTCAAGAC CCCTCGAAAG TTTGTGGAGC ACGTCAAGTC
CCAGGGACAC AAGGACAAGG CCCAAGAGCT GAAGACACTT GAAAAGGAGA
CAGGCAGCCC AGATGAGGAC CACTTCATCA CTGTGGACGC CGTCGGTTGC
TTTGAGAGTG GTCAAGAAGA GGACGAGGAT GACGACGAGGGAAGAGAAGA
AGAAGGAGAG ATTGAGGCTG AGGAGGAATT CTGCAAGCAG GTGAAGCCGA
GAGAAACATC CTCAGAGCAA GGGAAGGGCT CTGAGACGTA CAACCCCAAC
ACAGCCTATG GTGACGATTT CCTGCTGCCA GTGATGGCT ATGTCTGTCA
AATCTGTCAC AAGTTCTACG ACAGCAACTC AGAATTGCGC CTTTCCACT
GCAAGTCCCT GGCCCACTTT GAGAACCTGC AGAAATACAA AGCCAAGAAC
CCAAGCCTCC CTCCTACCCG GCCTGTGAGC CGCAAGTGTG CCATCAACCA
CCGCAACGTC CTGACTGCAC TGTTCACCTC TAGCTACCAG CCCAGCCCCC
AGGACACATT GAAAATGCCC AGCAAGGTGA AGCCTGGATC CCCCGGACTC
CCTCCTCCCC TTCGGCGCTC AACACGCCTC AAAACCTGAT AGAGGGAGCT
CTGCCCACCC AGCCTGACTA AGGCTCAGTC TGCTAATGCT TCCTAGGTAT
CTGTGTAGAA ATGTTCAAGT GGTTGGTGTT TTTACTCAAA ATCCAATAAA
GAGTCAGTAG TTTGGCAAAA AAAAAAAAAA AAAAAAA

MFNPQLQQQQ QLQQQQQQLQ QQLQQQQLQQ QQQQILQLQQ LLQQSPPQAS
LSIPVSRGLP QQSSPQQLLS LQGLHSTSLL NGPMLQRALL LQQLQGLDQF
AMPPATYDGA SLTMPTATLG NLRAFNVTAP SLAAPSLTPP QMVTPNLQQF
FPQATRQSLL GPPPVGVPIN PSQLNHSGRN TQKQARTPSS TTPNRKDSSS
QTVPLEDRED PTEGSEEATE LQMDTCEDQD SLVGPDSMLS EPQVPEPEPF
ETLEPPAKRC RSSEESTEKG PTGQPQARVQ PQTQMTAPKQ TQTPDRLPEP
PEVQMLPRIQ PQALQIQTQP KLLRQAQTQT SPEHLAPQQD QVEPQVPSQP
PWQLQPRETD PPNQAQAQTQ PQPLWQAQSQ KQAQTQAHPQ VPTQAQSQEQ
TSEKTQDQPQ TWPQGSVPPP EQASGPACAT EPQLSSHAAE AGSDPDKALP
EPVSAQSSED RSREASAGGL DLGECEKRAG EMLGMWGAGS SLKVTILQSS
NSRAFNTTPL TSGPRPGJST SATPAIASTP SKQSLQFFCY ICKASSSSQQ
EFQDHMSEAQ HQQRLGEIQH SSQTCLLSLL PMPRDILEKE AEDPPPKRWC
NTCQVYYVGD LIQHRRFQEH KVAKQSLRPF CTICNRYFKT PRKFVEHVKS
QGHKDKAQEL KTLEKETGSP DEDHFITVDA VGCFESGQEE DEDDDEEEEE
EGEIEAEEEF CKQVKPRETS SEQGKGSETY NPNTAYGEDF LVPVMGYVCQ
ICHKFYDSNS ELRLSHCKSL AHFENLQKYK AKNPSPPPTR PVSRKCAINA
RNALTALFTS SHQPSPQJTV KMPSKVKPGS PGLPPPLRRS TRLKT

*Fig. 16*

MF SQQQQQLQQQ QQQLQQQLQQQ QLLQLQQLLQQQ QLLQLQQLLQQSPPQ APLPM AVSRGLPPQ PQQPLLNLQG TNSASLLNGS M
LQRALLQQLQ GL DQFAMP PATY DTAGLT MPTATLGNLR GYGMASPGLA APSLTPPQLATPN LQQFFFQ ATRQSLLGPP PVGVPM
NPSQ FNLSGRNPQK QARTSSSTTPRRK DSSSQTM PVEDKSDPPE GSEEAAEPRM DTPEDQDLPP CPEDIAKEKRTPA PEPEPCE ASEL
PAKRLR SSEEPTEKEP PGQLQVKAQP QARMTVPKQTQTP DLLPEAL EAQVLPRFQP RVLQVQAQVQ SQTQPRIPST DTQVQPKLQK
QAQTQTSPEH LVLQQKQVQP QLQQEAEPQK QVQPQVQPQAHSQGPRQ VQLQQEAEPLKQV QPQVQPQAHS QPPRQVQLQLQKQV
QTQTYP QVHT QAQPSVQPQLHPPAQV SVQPPEQTHE QPHTQPQVSL LAPEQTPVVV HVC GLEMPPDAVEAGGGMEK TLPBPVGTQ
V SMEIQNESA CGLDVGLCEN RAREMPGVWGAGGSLKVTIL QSSIDSRAFST VPLTPVPRPS DS/SSTPAAT STPSKQALQHFCYCKA
SCS SQQEFQDHMS EPQHQQRLGE IQHMSQACLL SLLPVPRDVLFTEDHEPPPR RWCNTCQLYYMGDLIQHRRT QDHKIAKQSL RPF
CTVCNRYFRTPRAFVEH VKSQHHKDKA KELKSLEKEI ACQDEDHFFT VDAVGCFEGDEEEDEDEDE EEHEVEEELC KQVRSRDISR E
EWKGSETYS PNTAYGVDFLVPVMGYICRI CHKFYHSNSG AQLSHCKSLG HEENLQKYKA AKNISPTTRPVSRRCAINAR NALTALFTS
S GRPPSQPNTQ DKTPSKVTAR PSQPPLPRRSTRLKT

*Fig. 17*

From exons 2/3 (at least two versions)
MFSQQQQQQL QQQQQQLQQL QQQQLQQQQL QQQQLLQLQQ LLQQSPPQA

QQLQQL QQQQLQQQQL QQQQLLQLQQ LLQQSPP

Exon 4
GLDQFAMPPATYDTAGLTMPTATL

From exon 6
DSSSQ

From exon 8 (at least three versions)
PQVQPQAHSQPPRQVQLQLQKQVQTQTY

PQVQPQAHSQGPRQVQLQQEAEPLKQVQPQVQPQAHSQPPRQVQLQLQKQVQTQTY

QVQSQTQPRIPSTDTQVQPKLQKQAQTQ
TSPEHLVLQOKQVQPQLQQEAEPQKCVQ
PQVQPQAHSQGPRQVQLQQEAEPLKQVQ
PQVQPQAHSQPPRQVQLQLQKQVQTQTY

From exon 14
VEEELCKQ

The following sequence is inserted in one carcinoma derived library (MGC102) between the third and fourth zinc finger, altering the spacing between them.
PPTPRRDVFAHVPVQGWSTARLVTDN

*Fig. 18*

From exons 2/3 (at least two versions)
TGGGGCTGC GGGGCCGGCC CATCCGTGGG GGCGACTTGA GCGTTGAGGC CTCGCGGGGA GCYGAGCCAC
CATGTTCAGC CAGCAGCAGC AGCAGTTCAG AACAGCAG CAGCAGCTCC AGCAGTTACA GCAGCAGCAG
CTCCAGCAGCAGCAGCAATTGCA GCAGCAGCAG TTACTGCAGC TCCAGCAGCT GCTCCAGCAGTCCCACCAC
AGGCC CAGCAG CTCCAGCAGT TACAGCAGCA GCAGCAGCCAG CAGCAGTCCAG CAGCACCAATTGCAGCAGCA GCAGTTACTG CAGC
TCCAGC AGTCGCTCCA GCAGTCCCACCACA Exon 4
GGACTGGAC CAGTTTGCAA TGCCACCAGC CACGTATGAC ACTGCCGGTCTCACC ATGCC CACAGCAACA CTG
From exon 6
AGGATTCTTCTTCTC
From exon 8 (at least three versions)
CCACAGGTGC AGCCCCAGCC ACATTCACAG CCCCCAAGGC AGGTGCAGTCCACCTGCAG AAGCAGGTCC
AGACACAGAC ATATCC CCACAGGTAC AGCCACAGGC ACATTCACAG GGCCCAAGGC AGCCCAAGGC AGGTGCAGGAG GCAGAGCCGC
TGAAGCAGGT GCAGCCACAG GTCAGCCACAG CCAGGCACATTC ACAGCCCCA AGGCAGGTGC AGCTGCAGCT
GCAGAAGCAGGTCCAGACAC AGACATAT CAGGTGCAGT CACAGAATTCA GCCCCGGATA CCATCCACAG ACACCCAGTTGCAGCAAAG CTTCAGAAGC
AGCCGCAAAC ACAGACCTCT CCAGAGCACTTAGTGCTGCA ACAGAAGCAG GTGCAGCCAC AGTGCAGCA
GGAGGCAGAGCCAGACCAAGC AGTGCAGCC ACAGGTACAG CCACAGCAC CATTCACAGGGCCC AAGCCAG
GTGCAGCTCC AGCAGGAGGC AGAGCCGCTG AAGCAGGTCCAGGTGCAGTG CAGCCCCAG GCACATTCAC
AGCCCCAAG GCAGGTGCAGTCC AGGTGCAGGT CCAGACACAG ACACAT
From exon 14
GTTGAGGAGGAACTCTGCAAGCAG
The following sequence is inserted in re Ciz1 transcripts in one carcinoma library (from Ciz1 intron 12)
GCCACCCACACCACGAAGAGATGTGTTTGCCCACGTTCCAGTGCAGGGTGGAGCACAGCCCGGCTTGTTACAGATAT

*Fig. 19*

Part of exons 2/3 absent
MF SQQQQQLQQQ QQ APLPM AVSRGLPPQQ POQPLLSLQG TNSASLLNGS MLQRALLLQQLQ GL DQFAMP PATYDTAGLT MPTAT GNLR GYGMASPGLA APSLTPPQLA ATRQSLLGPP PVGVPMNPSQ FNLSGRNPQK QARTSSSTTPNRK DSSSQTM PVEDKSDPPE GSEEAAEPRM DTPEDQDI PP CPEDIALEKRTPA PEPEPCE ASELPAKRI R SSEEPTEKEP PCQOI QVKAQP QARMTVPKQTQTP DLLPEAL EAQVLPRFQP RVLQVQAQVQ SQTQPRIPST DTQVQPKLQKQAQTQTSPEH LVLQQKQVQP QLQQEAEPQK QVQPQVQPQAHSQGPRQ VQLQQEA EPLKQV QPQVQPQAHS QPPRQVQLQL QKQVQTQTYP QVHT QAQPSVQPQEHPPAQV SVQPPEQTHE QPHTQPQVSL LAPEQTPV VV HVC GLEMPPDAVE AGGGMEK TLPEPVGTQV SME EHQNESA CGLDVGECEN RAREMPGVWGAGGGSLKVTIL QSSDSRAFST VPLTPV PRFS DSVSSTPAAT STPSKQALQFFCYICKASCS SQQEFQDHMS EPQHQQRLGE IQHMSQALL SLLPVPRD VLETEDEEPPPR RWCNTCQLYY MGDLIQHRRT QDHKIAKQSL RPFCTVCNRYFKTPRKFVEH VKSQGHKDKA KELKSLEKEI AGQDEDHFIT VDAVGCFEGDEEEEDDEDE EEHEVEHLC K QVRSRDISR EEWKGSETYS PNTAYGVDFLVPVMGYICRI CHKFYHSNSG AQLSHCKSLG HFENLQKYKA AKNPSPTTRPVSRRCAINAR NALTALFTSS GRPPSQPNTQ DKTPSKVTAR PSQPP LPRRSTRLKT Exon 4 absent
MF SQQQQQLQQQ QQQQLQQQ QL QQQQQLQQQ QLQLQQLLQQSPPQ APLPM AVSRGLPPQQ POQPLLNLQG TNSASLLNGS MLQRALLLQQLQQNLR GYGMASPGLA APSLTPPQLA TPN LQQFFPQ ATRQSLLGPP PVGVPMNPSQ FNLSGRNPQK QARTSSSTTPNRK DSSSQTM PVEDKSDPPE GSEEAAEPRM DTPEDQDI PP CPEDIAKEKRTPA PEPEPCE ASEI PAKRI R SSE EPTEKEP PCQOLQVK AQP QARMTVPKQTQTP DLLPEAL EAQVLPRFQP RVLQVQAQVQ SQTQPRIPST DTQVQPKL QKQAQTQTSPEH LVLQQKQVQP QLQQEAEPQK QVQPQVQPQAHSQ GPRQ VQLQQEAEPLKQV QPQVQPQAHS QPPRQVQLQL QKQVQTQTYP QVHT QAQPSVQPQEHPPAQV SVQPPEQTHE QPHTQPQVSL LAPEQTPV VV HVC GLEMPPDAVE AGGGMEK T LPEPVGTQV SMEEHQNESA CGLDVGECEN RAREMPGVWGAGGGSLKVTIL QSSDSRAFST VPLTPV PRFS DSVSSTPAAT STPSKQALQFFCYICKASCS SQQEFQDHMS EPQHQQRLGE IQHM SQACLL SLLPVPRD VLETEDEEPPR RWCNTCQLYY MGDLIQHRRT QDHKIAKQSL RPFCTVCNRYFKTPRKFVEH VKSQGHKDKA KELKSLEKEI AGQDEDHFIT VDAVGCFEGDEEEED DEDE EEHEVEHLC C KQVRSRDISR EEWKGSETYS PNTAYGVDFLVPVMGYICRI CHKFYHSNSG AQLSHCKSLG HFENLQKYKA AKPSPTTRPVSRRCAIN AR NALTALFTSS GRPPSQPNTQ DKTPSKVTAR PSQPPLPRRSTRLKT Part of exon 6 absent
MF SQQQQQLQQQ QQQQLQQQ QL QQQQQLQQQ QLQLQQLLQQSPPQ APLPM AVSRGL PPQQ POQPL LNLQG TNSASLLNGS MLQRALLLQQLQ GL DQFAMP PATYDTAGLT MPTAT LGNLR GYGMASPGLA APSLTPPQLA APSLTPPQLA APSLTPPQLA ATRQSLLGPP PVGVPMNPSQ FNLSGRNPQK QARTSSSTTPNRK TM PVEDKSDPPE GSEEAAEPRM DTPEDQDLPP CPEDIAKEKRTPA PEPEPCE ASELPAKRLR SSEEPTEKEP PCQLQVK AQP QARMTVPKQTQTP DLL PEAL EAQVLPRFQP RVLQVQAQVQ SQTQPRIPST DTQVQPKI QKQAQTQTSPEH LVLQQKQVQP QLQQ EAEPQK QVQPQVQPQAHSQGPRQ VQLQQEAEPLKQV QPQVQPQAHS QPPRQVQLQL QKQVQTQTYP QVHT QAQPSVQPQEHPPAQV SVQPPEQTHE QPHTQPQVSL LAPEQTPV VV HVC GLEMPPDAVEAGGGMEK TLPEPVGTQV SMEEHQNESA CGLDVGECEN RAREMPGVWG AGGGSI KVTIL QSSDSRAFST VPLTPVPRFS DSVSSTPAAT STPSKQAI QFFCYICKASCS SQQEF QDHMS EPQHQQRLGE IQHMSQACLL SLLPVPRDVLETEDEEPPR RWCNTCQLYY MGDLIQHRRT QDHKIAKQSL RPFCTVCNRYIKTPRKFVEH VKSQGHKDKA KEI KSLEKEI AGQDE DHFIT VDAVGCFEGDEEEEDDEDE EEHEVEHLC KQVRSRDISR EEWKGSETYS PNTAYGVDFLVPVMGYICRI CHKFYHSNSG AQLSHCKSLG HFENLQKYKA AKNPSPTTRPVSRRCAIN AR NALTALFTSS GRPPSQPNTQ DKTPSKVTAR PSQPPLPRRSTRLKT Exon 8 minus variant 1
MF SQQQQQLQQQ QQQQLQQQ QL QQQQQLQQQ QLLLQLQQLLQQSPPQ APLPM AVSRGLPPQQ PQQPLLNLQG TNSASLLNGS MLQRALLLQQLQ GL DQFAMP PATYDTAGLT MPT ATL GNLR GYGMASPGLA APSLTPPQLA APSLTPPQLA APSLTPPQLA APSLTPPQLA ATPN LQQFFPQATRQSLLGPP PVGVPMNPSQ LQQFFPQATRQSLLGPP LQQFFPQATRQSLLGPP LQQFFPQATRQSLLGPP PVGVPMNPSQ FNLSGRNPQK QARTSSSTTPNRK DSSSQTN PVEDKSDPPE GSEEAAEPRM DTPEDKSDPPE LPP CPE DIAKEKRTPA PEPEPCE ASELPAKRLR SSE EPTEKEP PCQLQVK AQP QARMTV PKQTQTP DLLPEAL EAQVLPRFQP RVLQVQAQV0 SQTQPRIPST DTQVQPKLQKQAQTQTSPEH LVL QQKQVQP QLQQEAEPLKQV QPQVQPQAHSQGPRQ VQLQQEAEPLKQV QVQHT QAQPSVQPQEHPPAQV SVQPPEQTHE QPHTQPQVSL LAPEQTPV VV HVC GLEMPPDAVE AGGG MEK TLPEPVGTQV SMEEIQNESA CGLDVGECEN RAREMPGVWGAGGGSLKVTIL QSSDSRAFST VPLTPVPRFS DSVSSTPAAT STPSKQALQFFCYICKASCS SQQEFQDHMS EPQHQQR LGE IQHMSQACLL SLLPVPRDVLETEDEEPPPR RWCNTCQLYY MGDLIQHRRT QDHKIAKQSL RPFCTVCNRYFKTPRKFVEH VKSXGHKDKA KELKSLEKEI AGQDEDHFIT VDAVGC FEGDEEEEDDEDE EEHEVEHLC C KQVRSRDISR EEWIGSETYS PNTAYGVDFLVPVMGYICRI CHKFYHSNSG AQLSHCKSLG HFENLQKYKA AKNPSPTTRPVSRRCAINAR NALTAL FTSS GRPPSQPNTQ DKTPSKVTAR PSQPPLPRRSTRLKT

SEQUENCE LISTING

<160> NUMBER OF SEQ ID NOS: 74

<210> SEQ ID NO 1
<211> LENGTH: 5
<212> TYPE: PRT
<213> ORGANISM: Homo sapiens

<400> SEQUENCE: 1

Asp Ser Ser Ser Gln
1               5

<210> SEQ ID NO 2
<211> LENGTH: 24
<212> TYPE: DNA
<213> ORGANISM: Homo sapiens

<400> SEQUENCE: 2
gttgaggagg aactctgcaa gcag                                              24

<210> SEQ ID NO 3
<211> LENGTH: 8
<212> TYPE: PRT
<213> ORGANISM: Homo sapiens

<400> SEQUENCE: 3

Val Glu Glu Glu Leu Cys Lys Gln
1               5

<210> SEQ ID NO 4
<211> LENGTH: 78
<212> TYPE: DNA
<213> ORGANISM: Homo sapiens

<400> SEQUENCE: 4
gccacccaca ccacgaagag atgtgtttgc ccacgttcca gtgcaggggt ggagcacagc       60
ccggcttgtt acagatat                                                     78

<210> SEQ ID NO 5
<211> LENGTH: 32
<212> TYPE: DNA
<213> ORGANISM: Artificial
<220> FEATURE:
<223> OTHER INFORMATION: Oligonucleotide primer

<400> SEQUENCE: 5
aaccccctct tccgccgccc ccaatcgcaa ga                                     32

<210> SEQ ID NO 6
<211> LENGTH: 32
<212> TYPE: DNA
<213> ORGANISM: Artificial
<220> FEATURE:
<223> OTHER INFORMATION: Oligonucleotide primer

<400> SEQUENCE: 6
tcttgcgatt gggggcggcg gaagaggggg tt                                     32

<210> SEQ ID NO 7
<211> LENGTH: 30
<212> TYPE: DNA
<213> ORGANISM: Artificial
<220> FEATURE:
<223> OTHER INFORMATION: Oligonucleotide primer

<400> SEQUENCE: 7
aagcagacac aggcccccgga tcggctgcct                                       30

<210> SEQ ID NO 8
<211> LENGTH: 30
<212> TYPE: DNA
<213> ORGANISM: Artificial
<220> FEATURE:
<223> OTHER INFORMATION: Oligonucleotide primer

```
<400> SEQUENCE: 8
aggcagccga tccggggcct gtgtctgctt                                        30

<210> SEQ ID NO 9
<211> LENGTH: 29
<212> TYPE: DNA
<213> ORGANISM: Artificial
<220> FEATURE:
<223> OTHER INFORMATION: Oligonucleotide primer

<400> SEQUENCE: 9
aagcacagtc acaggagcag acctgtctc                                         29

<210> SEQ ID NO 10
<211> LENGTH: 29
<212> TYPE: DNA
<213> ORGANISM: Artificial
<220> FEATURE:
<223> OTHER INFORMATION: Oligonucleotide primer

<400> SEQUENCE: 10
aatctgctcc tgtgactgtg ccctgtctc                                         29

<210> SEQ ID NO 11
<211> LENGTH: 29
<212> TYPE: DNA
<213> ORGANISM: Artificial
<220> FEATURE:
<223> OTHER INFORMATION: Oligonucleotide primer

<400> SEQUENCE: 11
aatctgtcac aagttctacg acctgtctc                                         29

<210> SEQ ID NO 12
<211> LENGTH: 29
<212> TYPE: DNA
<213> ORGANISM: Artificial
<220> FEATURE:
<223> OTHER INFORMATION: Oligonucleotide primer

<400> SEQUENCE: 12
aatcgtagaa cttgtgacag acctgtctc                                         29

<210> SEQ ID NO 13
<211> LENGTH: 29
<212> TYPE: DNA
<213> ORGANISM: Artificial
<220> FEATURE:
<223> OTHER INFORMATION: Oligonucleotide primer

<400> SEQUENCE: 13
aatcgcaagg attcttcttc tcctgtctc                                         29

<210> SEQ ID NO 14
<211> LENGTH: 29
<212> TYPE: DNA
<213> ORGANISM: Artificial
<220> FEATURE:
<223> OTHER INFORMATION: Oligonucleotide primer

<400> SEQUENCE: 14
aaagaagaag aatccttgcg acctgtctc                                         29

<210> SEQ ID NO 15
```

```
<211> LENGTH: 29
<212> TYPE: DNA
<213> ORGANISM: Artificial
<220> FEATURE:
<223> OTHER INFORMATION: Oligonucleotide primer

<400> SEQUENCE: 15
aatctgcagc agttctttcc ccctgtctc                                       29

<210> SEQ ID NO 16
<211> LENGTH: 29
<212> TYPE: DNA
<213> ORGANISM: Artificial
<220> FEATURE:
<223> OTHER INFORMATION: Oligonucleotide primer

<400> SEQUENCE: 16
aagggaaaga actgctgcag acctgtctc                                       29

<210> SEQ ID NO 17
<211> LENGTH: 18
<212> TYPE: DNA
<213> ORGANISM: Artificial
<220> FEATURE:
<223> OTHER INFORMATION: Oligonucleotide primer

<400> SEQUENCE: 17
cagtccccac cacaggcc                                                   18

<210> SEQ ID NO 18
<211> LENGTH: 20
<212> TYPE: DNA
<213> ORGANISM: Artificial
<220> FEATURE:
<223> OTHER INFORMATION: Oligonucleotide primer

<400> SEQUENCE: 18
ggcttcctca gaccccctctg                                                20

<210> SEQ ID NO 19
<211> LENGTH: 25
<212> TYPE: DNA
<213> ORGANISM: Artificial
<220> FEATURE:
<223> OTHER INFORMATION: Oligonucleotide primer

<400> SEQUENCE: 19
acacagacct ctccagagca cttag                                           25

<210> SEQ ID NO 20
<211> LENGTH: 19
<212> TYPE: DNA
<213> ORGANISM: Artificial
<220> FEATURE:
<223> OTHER INFORMATION: Oligonucleotide primer

<400> SEQUENCE: 20
atggtgacct tcagggagc                                                  19

<210> SEQ ID NO 21
<211> LENGTH: 25
<212> TYPE: DNA
<213> ORGANISM: Artificial
<220> FEATURE:
<223> OTHER INFORMATION: Oligonucleotide primer

<400> SEQUENCE: 21
```
tccttggcga tgtcctctgg gcagg                                         25

<210> SEQ ID NO 22
<211> LENGTH: 25
<212> TYPE: DNA
<213> ORGANISM: Artificial
<220> FEATURE:
<223> OTHER INFORMATION: Oligonucleotide primer

<400> SEQUENCE: 22
tccctcctca acggctccat gctgc                                         25

<210> SEQ ID NO 23
<211> LENGTH: 25
<212> TYPE: DNA
<213> ORGANISM: Artificial
<220> FEATURE:
<223> OTHER INFORMATION: Oligonucleotide primer

<400> SEQUENCE: 23
cgtgggggcg acttgagcgt tgagg                                         25

<210> SEQ ID NO 24
<211> LENGTH: 25
<212> TYPE: DNA
<213> ORGANISM: Artificial
<220> FEATURE:
<223> OTHER INFORMATION: Oligonucleotide primer

<400> SEQUENCE: 24
gatgccaggg gtatggggcg ccggg                                         25

<210> SEQ ID NO 25
<211> LENGTH: 25
<212> TYPE: DNA
<213> ORGANISM: Artificial
<220> FEATURE:
<223> OTHER INFORMATION: Oligonucleotide primer

<400> SEQUENCE: 25
tccgagccct ccactcctc tctgg                                          25

<210> SEQ ID NO 26
<211> LENGTH: 845
<212> TYPE: PRT
<213> ORGANISM: Mus musculus

<400> SEQUENCE: 26

Met Phe Asn Pro Gln Leu Gln Gln Gln Gln Leu Gln Gln Gln Gln
1               5                   10                  15

Gln Gln Leu Gln Gln Leu Gln Gln Gln Leu Gln Gln Gln
            20                  25                  30

Gln Gln Ile Leu Gln Leu Gln Leu Leu Gln Ser Pro Pro Gln
        35                  40                  45

Ala Ser Leu Ser Ile Pro Val Ser Arg Gly Leu Pro Gln Gln Ser Ser
    50                  55                  60

Pro Gln Gln Leu Leu Ser Leu Gln Gly Leu His Ser Thr Ser Leu Leu
65                  70                  75                  80

Asn Gly Pro Met Leu Gln Arg Ala Leu Leu Leu Gln Leu Gln Gly
                85                  90                  95

Leu Asp Gln Phe Ala Met Pro Pro Ala Thr Tyr Asp Gly Ala Ser Leu
            100                 105                 110

-continued

```
Thr Met Pro Thr Ala Thr Leu Gly Asn Leu Arg Ala Phe Asn Val Thr
        115                 120                 125
Ala Pro Ser Leu Ala Ala Pro Ser Leu Thr Pro Pro Gln Met Val Thr
130                 135                 140
Pro Asn Leu Gln Gln Phe Phe Pro Gln Ala Thr Arg Gln Ser Leu Leu
145                 150                 155                 160
Gly Pro Pro Pro Val Gly Val Pro Ile Asn Pro Ser Gln Leu Asn His
                165                 170                 175
Ser Gly Arg Asn Thr Gln Lys Gln Ala Arg Thr Pro Ser Ser Thr Thr
            180                 185                 190
Pro Asn Arg Lys Asp Ser Ser Gln Thr Val Pro Leu Glu Asp Arg
        195                 200                 205
Glu Asp Pro Thr Glu Gly Ser Glu Glu Ala Thr Glu Leu Gln Met Asp
    210                 215                 220
Thr Cys Glu Asp Gln Asp Ser Leu Val Gly Pro Asp Ser Met Leu Ser
225                 230                 235                 240
Glu Pro Gln Val Pro Glu Pro Glu Pro Phe Glu Thr Leu Glu Pro Pro
                245                 250                 255
Ala Lys Arg Cys Arg Ser Ser Glu Glu Ser Thr Glu Lys Gly Pro Thr
            260                 265                 270
Gly Gln Pro Gln Ala Arg Val Gln Pro Gln Thr Gln Met Thr Ala Pro
        275                 280                 285
Lys Gln Thr Gln Thr Pro Asp Arg Leu Pro Glu Pro Pro Glu Val Gln
    290                 295                 300
Met Leu Pro Arg Ile Gln Pro Gln Ala Leu Gln Ile Gln Thr Gln Pro
305                 310                 315                 320
Lys Leu Leu Arg Gln Ala Gln Thr Gln Thr Ser Pro Glu His Leu Ala
                325                 330                 335
Pro Gln Gln Asp Gln Val Glu Pro Gln Val Pro Ser Gln Pro Pro Trp
            340                 345                 350
Gln Leu Gln Pro Arg Glu Thr Asp Pro Pro Asn Gln Ala Gln Ala Gln
        355                 360                 365
Thr Gln Pro Gln Pro Leu Trp Gln Ala Gln Ser Gln Lys Gln Ala Gln
    370                 375                 380
Thr Gln Ala His Pro Gln Val Pro Thr Gln Ala Gln Ser Gln Glu Gln
385                 390                 395                 400
Thr Ser Glu Lys Thr Gln Asp Gln Pro Gln Thr Trp Pro Gln Gly Ser
                405                 410                 415
Val Pro Pro Pro Glu Gln Ala Ser Gly Pro Ala Cys Ala Thr Glu Pro
            420                 425                 430
Gln Leu Ser Ser His Ala Ala Glu Ala Gly Ser Asp Pro Asp Lys Ala
        435                 440                 445
Leu Pro Glu Pro Val Ser Ala Gln Ser Ser Glu Asp Arg Ser Arg Glu
    450                 455                 460
Ala Ser Ala Gly Gly Leu Asp Leu Gly Glu Cys Glu Lys Arg Ala Gly
465                 470                 475                 480
Glu Met Leu Gly Met Trp Gly Ala Gly Ser Ser Leu Lys Val Thr Ile
                485                 490                 495
Leu Gln Ser Ser Asn Ser Arg Ala Phe Asn Thr Thr Pro Leu Thr Ser
            500                 505                 510
Gly Pro Arg Pro Gly Asp Ser Thr Ser Ala Thr Pro Ala Ile Ala Ser
        515                 520                 525
```

```
Thr Pro Ser Lys Gln Ser Leu Gln Phe Phe Cys Tyr Ile Cys Lys Ala
    530                 535                 540

Ser Ser Ser Ser Gln Gln Glu Phe Gln Asp His Met Ser Glu Ala Gln
545                 550                 555                 560

His Gln Gln Arg Leu Gly Glu Ile Gln His Ser Ser Gln Thr Cys Leu
                565                 570                 575

Leu Ser Leu Leu Pro Met Pro Arg Asp Ile Leu Glu Lys Glu Ala Glu
            580                 585                 590

Asp Pro Pro Lys Arg Trp Cys Asn Thr Cys Gln Val Tyr Tyr Val
            595                 600                 605

Gly Asp Leu Ile Gln His Arg Arg Thr Gln Glu His Lys Val Ala Lys
    610                 615                 620

Gln Ser Leu Arg Pro Phe Cys Thr Ile Cys Asn Arg Tyr Phe Lys Thr
625                 630                 635                 640

Pro Arg Lys Phe Val Glu His Val Lys Ser Gln Gly His Lys Asp Lys
                645                 650                 655

Ala Gln Glu Leu Lys Thr Leu Glu Lys Glu Thr Gly Ser Pro Asp Glu
            660                 665                 670

Asp His Phe Ile Thr Val Asp Ala Val Gly Cys Phe Glu Ser Gly Gln
    675                 680                 685

Glu Glu Asp Glu Asp Asp Glu Glu Glu Glu Glu Gly Glu Ile
690                 695                 700

Glu Ala Glu Glu Glu Phe Cys Lys Gln Val Lys Pro Arg Glu Thr Ser
705                 710                 715                 720

Ser Glu Gln Gly Lys Gly Ser Glu Thr Tyr Asn Pro Asn Thr Ala Tyr
                725                 730                 735

Gly Glu Asp Phe Leu Val Pro Val Met Gly Tyr Val Cys Gln Ile Cys
            740                 745                 750

His Lys Phe Tyr Asp Ser Asn Ser Glu Leu Arg Leu Ser His Cys Lys
    755                 760                 765

Ser Leu Ala His Phe Glu Asn Leu Gln Lys Tyr Lys Ala Lys Asn Pro
770                 775                 780

Ser Pro Pro Pro Thr Arg Pro Val Ser Arg Lys Cys Ala Ile Asn Ala
785                 790                 795                 800

Arg Asn Ala Leu Thr Ala Leu Phe Thr Ser Ser His Gln Pro Ser Pro
                805                 810                 815

Gln Asp Thr Val Lys Met Pro Ser Lys Val Lys Pro Gly Ser Pro Gly
            820                 825                 830

Leu Pro Pro Leu Arg Arg Ser Thr Arg Leu Lys Thr
    835                 840                 845

<210> SEQ ID NO 27
<211> LENGTH: 716
<212> TYPE: PRT
<213> ORGANISM: Mus musculus

<400> SEQUENCE: 27

Ser Thr Ser Leu Leu Asn Gly Pro Met Leu Gln Arg Ala Leu Leu Leu
1               5                   10                  15

Gln Gln Leu Gln Gly Leu Asp Gln Phe Ala Met Pro Pro Ala Thr Tyr
            20                  25                  30

Asp Gly Ala Ser Leu Thr Met Pro Thr Ala Leu Gly Asn Leu Arg
        35                  40                  45

Ala Phe Asn Val Thr Ala Pro Ser Leu Ala Ala Pro Ser Leu Thr Pro
50                  55                  60
```

```
Pro Gln Met Val Thr Pro Asn Leu Gln Gln Phe Phe Pro Gln Ala Thr
 65                  70                  75                  80

Arg Gln Ser Leu Leu Gly Pro Pro Val Gly Val Pro Ile Asn Pro
             85                  90                  95

Ser Gln Leu Asn His Ser Gly Arg Asn Thr Gln Lys Gln Ala Arg Thr
            100                 105                 110

Pro Ser Ser Thr Thr Pro Asn Arg Lys Thr Val Pro Leu Glu Asp Arg
        115                 120                 125

Glu Asp Pro Thr Glu Gly Ser Glu Ala Thr Glu Leu Gln Met Asp
    130                 135                 140

Thr Cys Glu Asp Gln Asp Ser Leu Val Gly Pro Asp Ser Met Leu Ser
145                 150                 155                 160

Glu Pro Gln Val Pro Glu Pro Glu Pro Phe Glu Thr Leu Glu Pro Pro
                165                 170                 175

Ala Lys Arg Cys Arg Ser Ser Glu Glu Ser Thr Glu Lys Gly Pro Thr
            180                 185                 190

Gly Gln Pro Gln Ala Arg Val Gln Pro Gln Thr Gln Met Thr Ala Pro
        195                 200                 205

Lys Gln Thr Gln Thr Pro Asp Arg Leu Pro Glu Pro Pro Glu Val Gln
210                 215                 220

Met Leu Pro Arg Ile Gln Pro Gln Ala Leu Gln Ile Gln Thr Gln Pro
225                 230                 235                 240

Lys Leu Leu Arg Gln Ala Gln Thr Gln Thr Ser Pro Glu His Leu Ala
            245                 250                 255

Pro Gln Gln Asp Gln Val Pro Thr Gln Ala Gln Ser Gln Glu Gln Thr
        260                 265                 270

Ser Glu Lys Thr Gln Asp Gln Pro Gln Thr Trp Pro Gln Gly Ser Val
    275                 280                 285

Pro Pro Pro Glu Gln Ala Ser Gly Pro Ala Cys Ala Thr Glu Pro Gln
290                 295                 300

Leu Ser Ser His Ala Ala Glu Ala Gly Ser Asp Pro Asp Lys Ala Leu
305                 310                 315                 320

Pro Glu Pro Val Ser Ala Gln Ser Ser Glu Asp Arg Ser Arg Glu Ala
            325                 330                 335

Ser Ala Gly Gly Leu Asp Leu Gly Glu Cys Glu Lys Arg Ala Gly Glu
        340                 345                 350

Met Leu Gly Met Trp Gly Ala Gly Ser Ser Leu Lys Val Thr Ile Leu
    355                 360                 365

Gln Ser Ser Asn Ser Arg Ala Phe Asn Thr Thr Pro Leu Thr Ser Gly
    370                 375                 380

Pro Arg Pro Gly Asp Ser Thr Ser Ala Thr Pro Ala Ile Ala Ser Thr
385                 390                 395                 400

Pro Ser Lys Gln Ser Leu Gln Phe Phe Cys Tyr Ile Cys Lys Ala Ser
            405                 410                 415

Ser Ser Ser Gln Gln Glu Phe Gln Asp His Met Ser Glu Ala Gln His
        420                 425                 430

Gln Gln Arg Leu Gly Glu Ile Gln His Ser Ser Gln Thr Cys Leu Leu
    435                 440                 445

Ser Leu Leu Pro Met Pro Arg Asp Ile Leu Glu Lys Glu Ala Glu Asp
    450                 455                 460

Pro Pro Pro Lys Arg Trp Cys Asn Thr Cys Gln Val Tyr Tyr Val Gly
465                 470                 475                 480
```

```
Asp Leu Ile Gln His Arg Arg Thr Gln Glu His Lys Val Ala Lys Gln
            485                 490                 495
Ser Leu Arg Pro Phe Cys Thr Ile Cys Asn Arg Tyr Phe Lys Thr Pro
        500                 505                 510
Arg Lys Phe Val Glu His Val Lys Ser Gln Gly His Lys Asp Lys Ala
    515                 520                 525
Gln Glu Leu Lys Thr Leu Glu Lys Glu Thr Gly Ser Pro Asp Glu Asp
530                 535                 540
His Phe Ile Thr Val Asp Ala Val Gly Cys Phe Glu Ser Gly Gln Glu
545                 550                 555                 560
Glu Asp Glu Asp Asp Glu Glu Glu Glu Gly Glu Ile Glu
                565                 570                 575
Ala Glu Glu Glu Phe Cys Lys Gln Val Lys Pro Arg Glu Thr Ser Ser
            580                 585                 590
Glu Gln Gly Lys Gly Ser Glu Thr Tyr Asn Pro Asn Thr Ala Tyr Gly
        595                 600                 605
Glu Asp Phe Leu Val Pro Val Met Gly Tyr Val Cys Gln Ile Cys His
    610                 615                 620
Lys Phe Tyr Asp Ser Asn Ser Glu Leu Arg Leu Ser His Cys Lys Ser
625                 630                 635                 640
Leu Ala His Phe Glu Asn Leu Gln Lys Tyr Lys Ala Lys Asn Pro Ser
                645                 650                 655
Pro Pro Pro Thr Arg Pro Val Ser Arg Lys Cys Ala Ile Asn Ala Arg
            660                 665                 670
Asn Ala Leu Thr Ala Leu Phe Thr Ser Ser His Gln Pro Ser Pro Gln
        675                 680                 685
Asp Thr Val Lys Met Pro Ser Lys Val Lys Pro Gly Ser Pro Gly Leu
    690                 695                 700
Pro Pro Pro Leu Arg Arg Ser Thr Arg Leu Lys Thr
705                 710                 715

<210> SEQ ID NO 28
<211> LENGTH: 714
<212> TYPE: PRT
<213> ORGANISM: Mus musculus

<400> SEQUENCE: 28

Met Phe Asn Pro Gln Leu Gln Gln Gln Gln Leu Gln Gln Gln Gln
1               5                   10                  15
Gln Gln Leu Gln Gln Gln Leu Gln Gln Gln Leu Gln Gln Gln
            20                  25                  30
Gln Gln Ile Leu Gln Leu Gln Gln Leu Leu Gln Ser Pro Pro Gln
            35                  40                  45
Ala Ser Leu Ser Ile Pro Val Ser Arg Gly Leu Pro Gln Gln Ser Ser
    50                  55                  60
Pro Gln Gln Leu Ser Leu Gln Gly Leu His Ser Thr Ser Leu Leu
65                  70                  75                  80
Asn Gly Pro Met Leu Gln Arg Ala Leu Leu Leu Gln Gln Leu Gln Gly
                85                  90                  95
Leu Asp Gln Phe Ala Met Pro Pro Ala Thr Tyr Asp Gly Ala Ser Leu
            100                 105                 110
Thr Met Pro Thr Ala Thr Leu Gly Asn Leu Arg Ala Phe Asn Val Thr
        115                 120                 125
Ala Pro Ser Leu Ala Ala Pro Ser Leu Thr Pro Pro Gln Met Val Thr
    130                 135                 140
```

```
Pro Asn Leu Gln Gln Phe Phe Pro Gln Ala Thr Arg Gln Ser Leu Leu
145                 150                 155                 160

Gly Pro Pro Pro Val Gly Val Pro Ile Asn Pro Ser Gln Leu Asn His
            165                 170                 175

Ser Gly Arg Asn Thr Gln Lys Gln Ala Arg Thr Pro Ser Ser Thr Thr
        180                 185                 190

Pro Asn Arg Lys Thr Val Pro Leu Glu Asp Arg Glu Asp Pro Thr Glu
    195                 200                 205

Gly Ser Glu Glu Ala Thr Glu Leu Gln Met Asp Thr Cys Glu Asp Gln
210                 215                 220

Asp Ser Leu Val Gly Pro Asp Ser Met Leu Ser Glu Pro Gln Val Pro
225                 230                 235                 240

Glu Pro Glu Pro Phe Glu Thr Leu Glu Pro Ala Lys Arg Cys Arg
                245                 250                 255

Ser Ser Glu Glu Ser Thr Glu Lys Gly Pro Thr Gly Gln Pro Gln Ala
            260                 265                 270

Arg Val Gln Pro Gln Thr Gln Met Thr Ala Pro Lys Gln Thr Gln Thr
        275                 280                 285

Pro Asp Arg Leu Pro Glu Pro Pro Glu Val Gln Met Leu Pro Arg Ile
    290                 295                 300

Gln Pro Gln Ala Leu Gln Ile Gln Thr Gln Pro Lys Leu Leu Arg Gln
305                 310                 315                 320

Ala Gln Thr Gln Thr Ser Pro Glu His Leu Ala Pro Gln Gln Asp Gln
                325                 330                 335

Val Pro Thr Gln Ala Gln Ser Gln Glu Gln Thr Ser Glu Lys Thr Gln
            340                 345                 350

Asp Gln Pro Gln Thr Trp Pro Gln Gly Ser Val Pro Pro Glu Gln
        355                 360                 365

Ala Ser Gly Pro Ala Cys Ala Thr Glu Pro Gln Leu Ser Ser His Ala
    370                 375                 380

Ala Glu Ala Gly Ser Asp Pro Asp Lys Ala Leu Pro Glu Pro Val Ser
385                 390                 395                 400

Ala Gln Ser Ser Glu Asp Arg Ser Arg Glu Ala Ser Ala Gly Gly Leu
                405                 410                 415

Asp Leu Gly Glu Cys Glu Lys Arg Ala Gly Glu Met Leu Gly Met Trp
            420                 425                 430

Gly Ala Gly Ser Ser Leu Lys Val Thr Ile Leu Gln Ser Ser Asn Ser
        435                 440                 445

Arg Ala Phe Asn Thr Thr Pro Leu Thr Ser Gly Pro Ser Pro Gly Asp
    450                 455                 460

Ser Thr Ser Ala Thr Pro Ala Ile Ala Ser Thr Pro Lys Gln Ser
465                 470                 475                 480

Leu Gln Phe Phe Cys Tyr Ile Cys Lys Ala Ser Ser Ser Ser Gln Gln
                485                 490                 495

Glu Phe Gln Asp His Met Ser Glu Ala Gln His Gln Gln Arg Leu Gly
            500                 505                 510

Glu Ile Gln His Ser Ser Gln Thr Cys Leu Leu Ser Leu Leu Pro Met
        515                 520                 525

Pro Arg Asp Ile Leu Glu Lys Glu Ala Glu Asp Pro Pro Lys Arg
    530                 535                 540

Trp Cys Asn Thr Cys Gln Val Tyr Tyr Val Gly Asp Leu Ile Gln His
545                 550                 555                 560
```

```
Arg Arg Thr Gln Glu His Lys Val Ala Lys Gln Ser Leu Arg Pro Phe
                565                 570                 575
Cys Thr Ile Cys Asn Arg Tyr Phe Lys Thr Pro Arg Lys Phe Val Glu
            580                 585                 590
His Val Lys Ser Gln Gly His Lys Asp Lys Ala Gln Glu Leu Lys Thr
        595                 600                 605
Leu Glu Lys Glu Thr Gly Ser Pro Asp Glu Asp His Phe Ile Thr Val
    610                 615                 620
Glu Ala Val Gly Cys Phe Glu Ser Gly Gln Glu Asp Glu Asp Asp
625                 630                 635                 640
Asp Glu Glu Glu Glu Glu Gly Glu Ile Glu Ala Glu Glu Phe
                645                 650                 655
Cys Lys Gln Val Lys Pro Arg Glu Thr Ser Glu Gln Gly Lys Gly
                660                 665                 670
Ser Glu Thr Tyr Asn Pro Asn Thr Ala Tyr Gly Glu Asp Phe Leu Val
                675                 680                 685
Pro Val Met Gly Tyr Val Cys Gln Ile Cys His Lys Phe Tyr Asp Ser
            690                 695                 700
Asn Ser Glu Leu Arg Leu Ser His Cys Lys
705                 710

<210> SEQ ID NO 29
<211> LENGTH: 898
<212> TYPE: PRT
<213> ORGANISM: Homo sapiens

<400> SEQUENCE: 29

Met Phe Ser Gln Gln Gln Gln Gln Leu Gln Gln Gln Gln Gln Gln
1               5                   10                  15
Leu Gln Gln Leu Gln Gln Gln Leu Gln Gln Gln Leu Gln Gln
                20                  25                  30
Gln Gln Leu Leu Gln Leu Gln Gln Leu Leu Gln Gln Ser Pro Pro Gln
            35                  40                  45
Ala Pro Leu Pro Met Ala Val Ser Arg Gly Leu Pro Pro Gln Gln Pro
        50                  55                  60
Gln Gln Pro Leu Leu Asn Leu Gln Gly Thr Asn Ser Ala Ser Leu Leu
65                  70                  75                  80
Asn Gly Ser Met Leu Gln Arg Ala Leu Leu Gln Gln Leu Gln Gly
                85                  90                  95
Leu Asp Gln Phe Ala Met Pro Pro Ala Thr Tyr Asp Thr Ala Gly Leu
            100                 105                 110
Thr Met Pro Thr Ala Thr Leu Gly Asn Leu Arg Gly Tyr Gly Met Ala
        115                 120                 125
Ser Pro Gly Leu Ala Ala Pro Ser Leu Thr Pro Gln Leu Ala Thr
            130                 135                 140
Pro Asn Leu Gln Gln Phe Phe Pro Gln Ala Thr Arg Gln Ser Leu Leu
145                 150                 155                 160
Gly Pro Pro Pro Val Gly Val Pro Met Asn Pro Ser Gln Phe Asn Leu
                165                 170                 175
Ser Gly Arg Asn Pro Gln Lys Gln Ala Arg Thr Ser Ser Thr Thr
            180                 185                 190
Pro Asn Arg Lys Asp Ser Ser Ser Gln Thr Met Pro Val Glu Asp Lys
        195                 200                 205
Ser Asp Pro Pro Glu Gly Ser Glu Glu Ala Ala Glu Pro Arg Met Asp
    210                 215                 220
```

```
Thr Pro Glu Asp Gln Asp Leu Pro Pro Cys Pro Asp Ile Ala Lys
225                 230                 235                 240

Glu Lys Arg Thr Pro Ala Pro Glu Pro Glu Pro Cys Glu Ala Ser Glu
            245                 250                 255

Leu Pro Ala Lys Arg Leu Arg Ser Ser Glu Glu Pro Thr Glu Lys Glu
            260                 265                 270

Pro Pro Gly Gln Leu Gln Val Lys Ala Gln Pro Gln Ala Arg Met Thr
            275                 280                 285

Val Pro Lys Gln Thr Gln Thr Pro Asp Leu Leu Pro Glu Ala Leu Glu
        290                 295                 300

Ala Gln Val Leu Pro Arg Phe Gln Pro Arg Val Leu Gln Val Gln Ala
305                 310                 315                 320

Gln Val Gln Ser Gln Thr Gln Pro Arg Ile Pro Ser Thr Asp Thr Gln
                325                 330                 335

Val Gln Pro Lys Leu Gln Lys Gln Ala Gln Thr Gln Thr Ser Pro Glu
        340                 345                 350

His Leu Val Leu Gln Gln Lys Gln Val Gln Pro Gln Leu Gln Gln Glu
        355                 360                 365

Ala Glu Pro Gln Lys Gln Val Gln Pro Gln Val Gln Pro Gln Ala His
370                 375                 380

Ser Gln Gly Pro Arg Gln Val Gln Leu Gln Gln Glu Ala Glu Pro Leu
385                 390                 395                 400

Lys Gln Val Gln Pro Gln Val Gln Pro Gln Ala His Ser Gln Pro Pro
                405                 410                 415

Arg Gln Val Gln Leu Gln Leu Gln Lys Gln Val Gln Thr Gln Thr Tyr
                420                 425                 430

Pro Gln Val His Thr Gln Ala Gln Pro Ser Val Gln Pro Gln Glu His
        435                 440                 445

Pro Pro Ala Gln Val Ser Val Gln Pro Glu Gln Thr His Glu Gln
450                 455                 460

Pro His Thr Gln Pro Gln Val Ser Leu Leu Ala Pro Glu Gln Thr Pro
465                 470                 475                 480

Val Val Val His Val Cys Gly Leu Glu Met Pro Pro Asp Ala Val Glu
                485                 490                 495

Ala Gly Gly Gly Met Glu Lys Thr Leu Pro Glu Pro Val Gly Thr Gln
                500                 505                 510

Val Ser Met Glu Glu Ile Gln Asn Glu Ser Ala Cys Gly Leu Asp Val
        515                 520                 525

Gly Glu Cys Glu Asn Arg Ala Arg Glu Met Pro Gly Val Trp Gly Ala
            530                 535                 540

Gly Gly Ser Leu Lys Val Thr Ile Leu Gln Ser Ser Asp Ser Arg Ala
545                 550                 555                 560

Phe Ser Thr Val Pro Leu Thr Pro Val Pro Arg Pro Ser Asp Ser Val
                565                 570                 575

Ser Ser Thr Pro Ala Ala Thr Ser Thr Pro Ser Lys Gln Ala Leu Gln
            580                 585                 590

Phe Phe Cys Tyr Ile Cys Lys Ala Ser Cys Ser Ser Gln Gln Glu Phe
            595                 600                 605

Gln Asp His Met Ser Glu Pro Gln His Gln Gln Arg Leu Gly Glu Ile
            610                 615                 620

Gln His Met Ser Gln Ala Cys Leu Leu Ser Leu Leu Pro Val Pro Arg
625                 630                 635                 640
```

```
Asp Val Leu Glu Thr Glu Asp Glu Glu Pro Pro Arg Arg Trp Cys
            645             650             655
Asn Thr Cys Gln Leu Tyr Tyr Met Gly Asp Leu Ile Gln His Arg Arg
        660                 665                 670
Thr Gln Asp His Lys Ile Ala Lys Gln Ser Leu Arg Pro Phe Cys Thr
            675                 680                 685
Val Cys Asn Arg Tyr Phe Lys Thr Pro Arg Lys Phe Val Glu His Val
        690                 695                 700
Lys Ser Gln Gly His Lys Asp Lys Ala Lys Glu Leu Lys Ser Leu Glu
705                 710                 715                 720
Lys Glu Ile Ala Gly Gln Asp Glu Asp His Phe Ile Thr Val Asp Ala
                725                 730                 735
Val Gly Cys Phe Glu Gly Asp Glu Glu Glu Asp Asp Glu Asp
            740                 745                 750
Glu Glu Glu Ile Glu Val Glu Glu Leu Cys Lys Gln Val Arg Ser
        755                 760                 765
Arg Asp Ile Ser Arg Glu Glu Trp Lys Gly Ser Glu Thr Tyr Ser Pro
770                 775                 780
Asn Thr Ala Tyr Gly Val Asp Phe Leu Val Pro Val Met Gly Tyr Ile
785                 790                 795                 800
Cys Arg Ile Cys His Lys Phe Tyr His Ser Asn Ser Gly Ala Gln Leu
                805                 810                 815
Ser His Cys Lys Ser Leu Gly His Phe Glu Asn Leu Gln Lys Tyr Lys
                820                 825                 830
Ala Ala Lys Asn Pro Ser Pro Thr Thr Arg Pro Val Ser Arg Arg Cys
                835                 840                 845
Ala Ile Asn Ala Arg Asn Ala Leu Thr Ala Leu Phe Thr Ser Ser Gly
        850                 855                 860
Arg Pro Pro Ser Gln Pro Asn Thr Gln Asp Lys Thr Pro Ser Lys Val
865                 870                 875                 880
Thr Ala Arg Pro Ser Gln Pro Pro Leu Pro Arg Arg Ser Thr Arg Leu
                885                 890                 895
Lys Thr

<210> SEQ ID NO 30
<211> LENGTH: 898
<212> TYPE: PRT
<213> ORGANISM: Homo sapiens

<400> SEQUENCE: 30

Met Phe Ser Gln Gln Gln Gln Gln Leu Gln Gln Gln Gln Gln Gln Gln
1               5                   10                  15
Leu Gln Gln Leu Gln Gln Gln Leu Gln Gln Gln Leu Gln Gln
            20                  25                  30
Gln Gln Leu Leu Gln Leu Gln Gln Leu Leu Gln Ser Pro Pro Gln
        35                  40                  45
Ala Pro Leu Pro Met Ala Val Ser Arg Gly Leu Pro Gln Gln Pro
    50                  55                  60
Gln Gln Pro Leu Leu Asn Leu Gln Gly Thr Asn Ser Ala Ser Leu Leu
65                  70                  75                  80
Asn Gly Ser Met Leu Gln Arg Ala Leu Leu Leu Gln Leu Gln Gly
                85                  90                  95
Leu Asp Gln Phe Ala Met Pro Pro Ala Thr Tyr Asp Thr Ala Gly Leu
                100                 105                 110
```

```
Thr Met Pro Thr Ala Thr Leu Gly Asn Leu Arg Gly Tyr Gly Met Ala
            115                 120                 125
Ser Pro Gly Leu Ala Ala Pro Ser Leu Thr Pro Gln Leu Ala Thr
130                 135                 140
Pro Asn Leu Gln Gln Phe Phe Pro Gln Ala Thr Arg Gln Ser Leu Leu
145                 150                 155                 160
Gly Pro Pro Pro Val Gly Val Pro Met Asn Pro Ser Gln Phe Asn Leu
                165                 170                 175
Ser Gly Arg Asn Pro Gln Lys Gln Ala Arg Thr Ser Ser Ser Thr Thr
            180                 185                 190
Pro Asn Arg Lys Asp Ser Ser Gln Thr Met Pro Val Glu Asp Lys
            195                 200                 205
Ser Asp Pro Pro Glu Gly Ser Glu Glu Ala Ala Glu Pro Arg Met Asp
210                 215                 220
Thr Pro Glu Asp Gln Asp Leu Leu Pro Cys Pro Glu Asp Ile Ala Lys
225                 230                 235                 240
Glu Lys Arg Thr Pro Ala Pro Glu Pro Glu Pro Cys Glu Ala Ser Glu
                245                 250                 255
Leu Pro Ala Lys Arg Leu Arg Ser Ser Glu Glu Pro Thr Glu Lys Glu
                260                 265                 270
Pro Pro Gly Gln Leu Gln Val Lys Ala Gln Pro Gln Ala Arg Met Thr
            275                 280                 285
Val Pro Lys Gln Thr Gln Thr Pro Asp Leu Leu Pro Glu Ala Leu Glu
            290                 295                 300
Ala Gln Val Leu Pro Arg Phe Gln Pro Arg Val Leu Gln Val Gln Ala
305                 310                 315                 320
Gln Val Gln Ser Gln Thr Gln Pro Arg Ile Pro Ser Thr Asp Thr Gln
                325                 330                 335
Val Gln Pro Lys Leu Gln Lys Gln Ala Gln Thr Gln Thr Ser Pro Glu
            340                 345                 350
His Leu Val Leu Gln Gln Lys Gln Val Gln Pro Gln Leu Gln Gln Glu
            355                 360                 365
Ala Glu Pro Gln Lys Gln Val Gln Pro Gln Val Gln Pro Gln Ala His
370                 375                 380
Ser Gln Gly Pro Arg Gln Val Gln Leu Gln Gln Glu Ala Glu Pro Leu
385                 390                 395                 400
Lys Gln Val Gln Pro Gln Val Gln Pro Gln Ala His Ser Gln Pro Pro
                405                 410                 415
Arg Gln Val Gln Leu Gln Leu Gln Lys Gln Val Gln Thr Gln Thr Tyr
            420                 425                 430
Pro Gln Val His Thr Gln Ala Gln Pro Ser Val Gln Pro Gln Glu His
            435                 440                 445
Pro Pro Ala Gln Val Ser Val Gln Pro Pro Glu Gln Thr His Glu Gln
450                 455                 460
Pro His Thr Gln Pro Gln Val Ser Leu Leu Ala Pro Glu Gln Thr Pro
465                 470                 475                 480
Val Val Val His Val Cys Gly Leu Glu Met Pro Pro Asp Ala Val Glu
                485                 490                 495
Ala Gly Gly Gly Met Glu Lys Thr Leu Pro Glu Pro Val Gly Thr Gln
            500                 505                 510
Val Ser Met Glu Glu Ile Gln Asn Glu Ser Ala Cys Gly Leu Asp Val
            515                 520                 525
Gly Glu Cys Glu Asn Arg Ala Arg Glu Met Pro Gly Val Trp Gly Ala
```

```
            530                 535                 540
Gly Gly Ser Leu Lys Val Thr Ile Leu Gln Gly Ser Asp Ser Arg Ala
545                 550                 555                 560

Phe Ser Thr Val Pro Leu Thr Pro Val Pro Arg Pro Ser Asp Ser Val
                565                 570                 575

Ser Ser Thr Pro Ala Ala Thr Ser Pro Ser Lys Gln Ala Leu Gln
            580                 585                 590

Phe Phe Cys Tyr Ile Cys Lys Ala Ser Cys Ser Ser Gln Gln Glu Phe
                595                 600                 605

Gln Asp His Met Ser Glu Pro Gln His Gln Gln Arg Leu Gly Glu Ile
            610                 615                 620

Gln His Met Ser Gln Ala Cys Leu Leu Ser Leu Leu Pro Val Pro Arg
625                 630                 635                 640

Asp Val Leu Glu Thr Glu Asp Glu Glu Pro Pro Arg Arg Trp Cys
                645                 650                 655

Asn Thr Cys Gln Leu Tyr Tyr Met Gly Asp Leu Ile Gln His Arg Arg
                660                 665                 670

Thr Gln Asp His Lys Ile Ala Lys Gln Ser Leu Arg Pro Phe Cys Thr
                675                 680                 685

Val Cys Asn Arg Tyr Phe Lys Thr Pro Arg Lys Phe Val Glu His Val
690                 695                 700

Lys Ser Gln Gly His His Lys Asp Lys Ala Lys Glu Leu Lys Ser Leu Glu
705                 710                 715                 720

Lys Glu Ile Ala Gly Gln Asp Glu Asp His Phe Ile Thr Val Asp Ala
                725                 730                 735

Val Gly Cys Phe Glu Gly Asp Glu Glu Glu Asp Asp Glu Asp
                740                 745                 750

Glu Glu Glu Ile Glu Val Glu Glu Leu Cys Lys Gln Val Arg Ser
            755                 760                 765

Arg Asp Ile Ser Arg Glu Glu Trp Lys Gly Ser Glu Thr Tyr Ser Pro
770                 775                 780

Asn Thr Ala Tyr Gly Val Asp Phe Leu Val Pro Val Met Gly Tyr Ile
785                 790                 795                 800

Cys Arg Ile Cys His Lys Phe Tyr His Ser Asn Ser Gly Ala Gln Leu
                805                 810                 815

Ser His Cys Lys Ser Leu Gly His Phe Glu Asn Leu Gln Lys Tyr Lys
            820                 825                 830

Ala Ala Lys Asn Pro Ser Pro Thr Thr Arg Pro Val Ser Arg Arg Cys
            835                 840                 845

Ala Ile Asn Ala Arg Asn Ala Leu Thr Ala Leu Phe Thr Ser Ser Gly
850                 855                 860

Arg Pro Pro Ser Gln Pro Asn Thr Gln Asp Lys Thr Pro Ser Lys Val
865                 870                 875                 880

Thr Ala Arg Pro Ser Gln Pro Pro Leu Pro Arg Arg Ser Thr Arg Leu
                885                 890                 895

Lys Thr

<210> SEQ ID NO 31
<211> LENGTH: 896
<212> TYPE: PRT
<213> ORGANISM: Homo sapiens

<400> SEQUENCE: 31

Phe Ser Gln Gln Gln Gln Gln Leu Gln Gln Gln Gln Gln Gln Leu Gln
```

-continued

```
1               5                   10                  15
Gln Leu Gln Gln Gln Gln Leu Gln Gln Gln Gln Leu Gln Gln Gln Gln
                20                  25                  30
Ser Leu Gln Leu Gln Gln Leu Leu Gln Gln Ser Pro Pro Gln Ala Pro
                35                  40                  45
Leu Pro Met Ala Val Ser Arg Gly Leu Pro Pro Gln Gln Pro Gln Gln
50                                  55                  60
Pro Leu Leu Asn Leu Gln Gly Thr Asn Ser Ala Ser Leu Leu Asn Gly
65                                  70                  75                  80
Ser Met Leu Gln Arg Ala Leu Leu Gln Gln Leu Gln Gly Leu Asp
                85                  90                  95
Gln Phe Ala Met Pro Ala Thr Tyr Asp Thr Ala Gly Leu Thr Met
                100                 105                 110
Pro Thr Ala Thr Leu Gly Asn Leu Arg Gly Tyr Gly Met Ala Ser Pro
                115                 120                 125
Gly Leu Ala Ala Pro Ser Leu Thr Pro Pro Gln Leu Ala Thr Pro Asn
                130                 135                 140
Leu Gln Gln Phe Phe Pro Gln Ala Thr Arg Gln Ser Leu Leu Gly Pro
145                 150                 155                 160
Pro Pro Val Gly Val Pro Met Asn Pro Ser Gln Phe Asn Leu Ser Gly
                165                 170                 175
Arg Asn Pro Gln Lys Gln Ala Arg Thr Ser Ser Ser Thr Pro Asn
                180                 185                 190
Arg Lys Asp Ser Ser Ser Gln Thr Met Pro Val Glu Asp Lys Ser Asp
                195                 200                 205
Pro Pro Glu Gly Ser Glu Glu Ala Ala Glu Pro Arg Met Asp Thr Pro
                210                 215                 220
Glu Asp Gln Asp Leu Pro Pro Cys Pro Glu Asp Ile Ala Lys Glu Lys
225                 230                 235                 240
Arg Thr Pro Ala Pro Glu Pro Glu Pro Cys Glu Ala Ser Glu Leu Pro
                245                 250                 255
Ala Lys Arg Leu Arg Ser Ser Glu Glu Pro Thr Glu Lys Glu Pro Pro
                260                 265                 270
Gly Gln Leu Gln Val Lys Ala Gln Pro Gln Ala Arg Met Thr Val Pro
                275                 280                 285
Lys Gln Thr Gln Thr Pro Asp Leu Leu Pro Glu Ala Leu Glu Ala Gln
                290                 295                 300
Val Leu Pro Arg Phe Gln Pro Arg Val Leu Gln Val Gln Ala Gln Val
305                 310                 315                 320
Gln Ser Gln Thr Gln Pro Arg Ile Pro Ser Thr Asp Thr Gln Val Gln
                325                 330                 335
Pro Lys Leu Gln Lys Gln Ala Gln Thr Gln Thr Ser Pro Glu His Leu
                340                 345                 350
Val Leu Gln Gln Lys Gln Val Gln Pro Gln Leu Gln Gln Glu Ala Glu
                355                 360                 365
Pro Gln Lys Gln Val Gln Pro Gln Val Gln Pro Gln Ala His Ser Gln
                370                 375                 380
Gly Pro Arg Gln Val Gln Leu Gln Gln Glu Ala Glu Pro Leu Lys Gln
385                 390                 395                 400
Val Gln Pro Gln Val Gln Pro Gln Ala His Ser Gln Pro Pro Arg Gln
                405                 410                 415
Val Gln Leu Gln Leu Gln Lys Gln Val Gln Thr Gln Thr Tyr Pro Gln
                420                 425                 430
```

-continued

```
Val His Thr Gln Ala Gln Pro Ser Val Gln Pro Gln Glu His Pro Pro
            435                 440                 445

Ala Gln Val Ser Val Gln Pro Pro Glu Gln Thr His Glu Gln Pro His
450                 455                 460

Thr Gln Pro Gln Val Ser Leu Leu Ala Pro Glu Gln Thr Pro Val Val
465                 470                 475                 480

Val His Val Cys Gly Leu Glu Met Pro Pro Asp Ala Val Glu Ala Gly
                    485                 490                 495

Gly Gly Met Glu Lys Thr Leu Pro Glu Pro Val Gly Thr Gln Val Ser
                500                 505                 510

Met Glu Glu Ile Gln Asn Glu Ser Ala Cys Gly Leu Asp Val Gly Glu
            515                 520                 525

Cys Glu Asn Arg Ala Arg Glu Met Pro Gly Val Trp Gly Ala Gly Gly
530                 535                 540

Ser Leu Lys Val Thr Ile Leu Gln Ser Ser Asp Ser Arg Ala Phe Ser
545                 550                 555                 560

Thr Val Pro Leu Thr Leu Val Pro Arg Pro Ser Asp Ser Val Ser Ser
                    565                 570                 575

Thr Pro Ala Ala Thr Ser Thr Pro Ser Lys Gln Ala Leu Gln Phe Phe
                580                 585                 590

Cys Tyr Ile Cys Lys Ala Ser Cys Ser Ser Gln Gln Glu Phe Gln Asp
            595                 600                 605

His Met Ser Glu Pro Gln His Gln Gln Arg Leu Gly Glu Ile Gln His
610                 615                 620

Met Ser Gln Ala Cys Leu Leu Pro Leu Leu Val Pro Arg Asp Val
625                 630                 635                 640

Leu Glu Thr Glu Asp Glu Glu Pro Pro Arg Arg Trp Cys Asn Thr
                    645                 650                 655

Cys Gln Leu Tyr Tyr Met Gly Asp Leu Ile Gln His Arg Arg Thr Gln
                660                 665                 670

Asp His Lys Ile Ala Lys Gln Ser Leu Arg Pro Phe Cys Thr Val Cys
            675                 680                 685

Asn Arg Tyr Phe Lys Thr Pro Arg Lys Phe Val Glu His Val Lys Ser
690                 695                 700

Gln Gly His Lys Asp Lys Ala Lys Glu Leu Lys Ser Leu Glu Lys Glu
705                 710                 715                 720

Ile Ala Gly Gln Asp Glu Asp His Phe Ile Thr Val Gly Ala Val Gly
                    725                 730                 735

Cys Phe Glu Gly Asp Glu Glu Glu Glu Asp Asp Glu Asp Glu Glu
                740                 745                 750

Glu Ile Glu Val Glu Glu Glu Leu Cys Lys Gln Val Arg Ser Arg Asp
            755                 760                 765

Ile Ser Arg Glu Glu Trp Lys Gly Ser Glu Thr Tyr Ser Pro Asn Thr
770                 775                 780

Ala Tyr Gly Val Asp Phe Leu Val Pro Val Met Gly Tyr Ile Cys Arg
785                 790                 795                 800

Ile Cys His Lys Phe Tyr His Ser Asn Ser Gly Ala Gln Leu Ser His
                    805                 810                 815

Cys Lys Ser Leu Gly His Phe Glu Asn Leu Gln Lys Tyr Lys Ala Ala
                820                 825                 830

Lys Asn Pro Ser Pro Thr Thr Arg Pro Val Ser Arg Arg Cys Ala Ile
            835                 840                 845
```

```
Asn Ala Arg Asn Ala Leu Thr Ala Leu Phe Thr Ser Ser Gly Arg Pro
            850                 855                 860
Pro Ser Gln Pro Asn Thr Gln Asp Lys Thr Pro Ser Lys Val Thr Ala
865                 870                 875                 880
Arg Pro Ser Gln Pro Pro Leu Pro Arg Arg Ser Thr Arg Leu Lys Thr
                885                 890                 895

<210> SEQ ID NO 32
<211> LENGTH: 842
<212> TYPE: PRT
<213> ORGANISM: Homo sapiens

<400> SEQUENCE: 32

Met Phe Ser Gln Gln Gln Gln Gln Leu Gln Gln Gln Gln Gln Gln Gln
1               5                   10                  15
Leu Gln Gln Leu Gln Gln Gln Leu Gln Gln Gln Gln Leu Gln Gln
            20                  25                  30
Gln Gln Leu Leu Gln Leu Gln Gln Leu Leu Gln Ser Pro Pro Gln
            35                  40                  45
Ala Pro Leu Pro Met Ala Val Ser Arg Gly Leu Pro Pro Gln Gln Pro
    50                  55                  60
Gln Gln Pro Leu Leu Asn Leu Gln Gly Thr Asn Ser Ala Ser Leu Leu
65                  70                  75                  80
Asn Gly Ser Met Leu Gln Arg Ala Leu Leu Gln Gln Leu Gln Gly
                85                  90                  95
Leu Asp Gln Phe Val Met Pro Ala Thr Tyr Asp Thr Ala Gly Leu
            100                 105                 110
Thr Met Pro Thr Ala Thr Leu Gly Asn Leu Arg Gly Tyr Gly Met Ala
            115                 120                 125
Ser Pro Gly Leu Ala Ala Pro Ser Leu Thr Pro Pro Gln Leu Ala Thr
    130                 135                 140
Pro Asn Leu Gln Gln Phe Phe Pro Gln Ala Thr Arg Gln Ser Leu Leu
145                 150                 155                 160
Gly Pro Pro Pro Val Gly Val Pro Met Asn Pro Ser Gln Phe Asn Leu
                165                 170                 175
Ser Gly Arg Asn Pro Gln Lys Gln Ala Arg Thr Ser Ser Ser Thr Thr
            180                 185                 190
Pro Asn Arg Lys Asp Ser Ser Ser Gln Thr Met Pro Val Glu Asp Lys
        195                 200                 205
Ser Asp Pro Pro Glu Gly Ser Glu Glu Ala Ala Glu Pro Arg Met Asp
    210                 215                 220
Thr Pro Glu Asp Gln Asp Leu Pro Pro Cys Pro Glu Asp Ile Ala Lys
225                 230                 235                 240
Glu Lys Arg Thr Pro Ala Pro Glu Pro Glu Pro Cys Glu Ala Ser Glu
                245                 250                 255
Leu Pro Ala Lys Arg Leu Arg Ser Ser Glu Glu Pro Thr Glu Lys Glu
            260                 265                 270
Pro Pro Gly Gln Leu Gln Val Lys Ala Gln Pro Gln Ala Arg Met Thr
        275                 280                 285
Val Pro Lys Gln Thr Gln Thr Pro Asp Leu Leu Pro Glu Ala Leu Glu
    290                 295                 300
Ala Gln Val Leu Pro Arg Phe Gln Pro Arg Val Leu Gln Val Gln Ala
305                 310                 315                 320
Gln Val Gln Ser Gln Thr Gln Pro Arg Ile Pro Ser Thr Asp Thr Gln
                325                 330                 335
```

-continued

Val Gln Pro Lys Leu Gln Lys Gln Ala Gln Thr Gln Thr Ser Pro Glu
            340                 345                 350

His Leu Val Leu Gln Gln Lys Gln Val Gln Pro Gln Leu Gln Gln Glu
            355                 360                 365

Ala Glu Pro Gln Lys Gln Val Gln Pro Gln Val His Thr Gln Ala Gln
            370                 375                 380

Pro Ser Val Gln Pro Gln Glu His Pro Pro Ala Gln Val Ser Val Gln
385                 390                 395                 400

Pro Pro Glu Gln Thr His Glu Gln Pro His Thr Gln Pro Gln Val Ser
            405                 410                 415

Leu Leu Ala Pro Glu Gln Thr Pro Val Val His Val Cys Gly Leu
            420                 425                 430

Glu Met Pro Pro Asp Ala Val Glu Ala Gly Gly Gly Met Glu Lys Thr
            435                 440                 445

Leu Pro Glu Pro Val Gly Thr Gln Val Ser Met Glu Glu Ile Gln Asn
            450                 455                 460

Glu Ser Ala Cys Gly Leu Asp Val Gly Glu Cys Glu Asn Arg Ala Arg
465                 470                 475                 480

Glu Met Pro Gly Val Trp Gly Ala Gly Gly Ser Leu Lys Val Thr Ile
            485                 490                 495

Leu Gln Ser Ser Asp Ser Arg Ala Phe Ser Thr Val Pro Leu Thr Pro
            500                 505                 510

Val Pro Arg Pro Ser Asp Ser Val Ser Ser Thr Pro Ala Ala Thr Ser
            515                 520                 525

Thr Pro Ser Lys Gln Ala Leu Gln Phe Phe Cys Tyr Ile Cys Lys Ala
            530                 535                 540

Ser Cys Ser Ser Gln Gln Glu Phe Gln Asp His Met Ser Glu Pro Gln
545                 550                 555                 560

His Gln Gln Arg Leu Gly Glu Ile Gln His Met Ser Gln Ala Cys Leu
            565                 570                 575

Leu Ser Leu Leu Pro Met Pro Arg Asp Val Leu Glu Thr Glu Asp Glu
            580                 585                 590

Glu Pro Pro Pro Arg Arg Trp Cys Asn Thr Cys Gln Leu Tyr Tyr Met
            595                 600                 605

Gly Asp Leu Ile Gln His Arg Arg Thr Gln Asp His Lys Val Ala Lys
            610                 615                 620

Gln Pro Leu Arg Pro Phe Cys Thr Val Cys Asn Arg Tyr Phe Lys Thr
625                 630                 635                 640

Pro Arg Lys Phe Val Glu His Val Lys Ser Gln Gly His Lys Asp Lys
            645                 650                 655

Ala Lys Glu Leu Lys Ser Leu Gly Lys Glu Ile Ala Gly Gln Asp Glu
            660                 665                 670

Asp His Phe Ile Thr Val Asp Ala Val Gly Cys Phe Glu Gly Asp Glu
            675                 680                 685

Glu Glu Glu Glu Asp Asp Glu Asp Glu Glu Ile Lys Val Glu Glu
            690                 695                 700

Glu Leu Cys Lys Gln Val Arg Ser Arg Asp Ile Ser Arg Glu Glu Trp
705                 710                 715                 720

Lys Gly Ser Glu Thr Tyr Ser Pro Asn Thr Ala Tyr Gly Val Asp Phe
            725                 730                 735

Leu Val Pro Val Met Gly Tyr Ile Cys Arg Ile Cys His Lys Phe Tyr
            740                 745                 750

His Ser Asn Ser Gly Ala Gln Leu Ser His Cys Lys Ser Leu Gly His
            755                 760                 765

Phe Glu Asn Leu Gln Lys Tyr Lys Ala Ala Lys Asn Pro Ser Pro Thr
            770                 775                 780

Thr Arg Pro Val Ser Arg Arg Cys Ala Ile Asn Ala Arg Asn Ala Leu
785                 790                 795                 800

Thr Ala Leu Phe Thr Ser Ser Gly Arg Pro Pro Ser Gln Pro Asn Thr
                    805                 810                 815

Gln Asp Lys Thr Pro Ser Lys Val Thr Ala Arg Pro Ser Gln Pro Pro
                    820                 825                 830

Leu Pro Arg Arg Ser Thr Arg Leu Lys Thr
            835                 840

<210> SEQ ID NO 33
<211> LENGTH: 837
<212> TYPE: PRT
<213> ORGANISM: Homo sapiens

<400> SEQUENCE: 33

Met Phe Ser Gln Gln Gln Gln Gln Leu Gln Gln Gln Gln Gln Gln Ala
1               5                   10                  15

Pro Leu Pro Met Ala Val Ser Arg Gly Leu Pro Pro Gln Gln Pro Gln
                20                  25                  30

Gln Pro Leu Leu Asn Leu Gln Gly Thr Asn Ser Ala Ser Leu Leu Asn
            35                  40                  45

Gly Ser Met Leu Gln Arg Ala Leu Leu Leu Gln Gln Leu Gln Gly Leu
        50                  55                  60

Asp Gln Phe Ala Met Pro Pro Ala Thr Tyr Asp Thr Ala Gly Leu Thr
65              70                  75                  80

Met Pro Thr Ala Thr Leu Gly Asn Leu Arg Gly Tyr Gly Met Ala Ser
                85                  90                  95

Pro Gly Leu Ala Ala Pro Ser Leu Thr Pro Pro Gln Leu Ala Thr Pro
            100                 105                 110

Asn Leu Gln Gln Phe Phe Pro Gln Ala Thr Arg Gln Ser Leu Leu Gly
        115                 120                 125

Pro Pro Pro Val Gly Val Pro Met Asn Pro Ser Gln Phe Asn Leu Ser
130                 135                 140

Gly Arg Asn Pro Gln Lys Gln Ala Arg Thr Ser Ser Ser Thr Thr Pro
145                 150                 155                 160

Asn Arg Lys Asp Ser Ser Ser Gln Thr Met Pro Val Glu Asp Lys Ser
                165                 170                 175

Asp Pro Pro Glu Gly Ser Glu Glu Ala Ala Glu Pro Arg Met Asp Thr
            180                 185                 190

Pro Glu Asp Gln Asp Leu Pro Cys Pro Glu Asp Ile Ala Lys Glu
        195                 200                 205

Lys Arg Thr Pro Ala Pro Glu Pro Glu Pro Cys Glu Ala Ser Glu Leu
        210                 215                 220

Pro Ala Lys Arg Leu Arg Ser Ser Glu Glu Pro Thr Glu Lys Glu Pro
225                 230                 235                 240

Pro Gly Gln Leu Gln Val Lys Ala Gln Pro Ala Arg Met Thr Val
                245                 250                 255

Pro Lys Gln Thr Gln Thr Pro Asp Leu Leu Pro Glu Ala Leu Glu Ala
            260                 265                 270

Gln Val Leu Pro Arg Phe Gln Pro Arg Val Leu Gln Val Gln Ala Gln
        275                 280                 285

```
        Val Gln Ser Gln Thr Gln Pro Arg Ile Pro Ser Thr Asp Thr Gln Val
            290                 295                 300

Gln Pro Lys Leu Gln Lys Gln Ala Gln Thr Gln Ser Pro Glu His
        305                 310                 315                 320

Leu Val Leu Gln Gln Lys Gln Val Gln Pro Gln Leu Gln Gln Glu Ala
                        325                 330                 335

Glu Pro Gln Lys Gln Val Gln Pro Gln Val Gln Pro Gln Ala His Ser
                        340                 345                 350

Gln Gly Pro Arg Gln Val Gln Leu Gln Gln Glu Ala Glu Pro Leu Lys
                        355                 360                 365

Gln Val Gln Pro Gln Val His Thr Gln Ala Gln Pro Ser Val Gln Pro
            370                 375                 380

Gln Glu His Pro Pro Ala Gln Val Ser Val Gln Pro Pro Glu Gln Thr
        385                 390                 395                 400

His Glu Gln Pro His Thr Gln Pro Gln Val Ser Leu Leu Ala Pro Glu
                        405                 410                 415

Gln Thr Pro Val Val His Val Cys Gly Leu Glu Met Pro Pro Asp
                        420                 425                 430

Ala Val Glu Ala Gly Gly Met Glu Lys Thr Leu Pro Glu Pro Val
                        435                 440                 445

Gly Thr Gln Val Ser Met Glu Glu Ile Gln Asn Glu Ser Ala Cys Gly
            450                 455                 460

Leu Asp Val Gly Glu Cys Glu Asn Arg Ala Arg Glu Met Pro Gly Val
        465                 470                 475                 480

Trp Gly Ala Gly Gly Ser Leu Lys Val Thr Ile Leu Gln Ser Ser Asp
                        485                 490                 495

Ser Arg Ala Phe Ser Thr Val Pro Leu Thr Pro Val Pro Arg Pro Ser
                        500                 505                 510

Asp Ser Val Ser Ser Thr Pro Ala Ala Thr Ser Thr Pro Ser Lys Gln
                        515                 520                 525

Ala Leu Gln Phe Phe Cys Tyr Ile Cys Lys Ala Ser Cys Ser Ser Gln
            530                 535                 540

Gln Glu Phe Gln Asp His Met Ser Glu Pro Gln His Gln Gln Arg Leu
        545                 550                 555                 560

Gly Glu Ile Gln His Met Ser Gln Ala Cys Leu Leu Ser Leu Leu Pro
                        565                 570                 575

Val Pro Arg Asp Val Leu Glu Thr Glu Asp Glu Pro Pro Pro Arg
                        580                 585                 590

Arg Trp Cys Asn Thr Cys Gln Leu Tyr Tyr Met Gly Asp Leu Ile Gln
            595                 600                 605

His Arg Arg Thr Gln Asp His Lys Ile Ala Lys Gln Ser Leu Arg Pro
        610                 615                 620

Phe Cys Thr Val Cys Asn Arg Tyr Phe Lys Thr Pro Arg Lys Phe Val
        625                 630                 635                 640

Glu His Val Lys Ser Gln Gly His His Lys Asp Lys Ala Lys Glu Leu Lys
                        645                 650                 655

Ser Leu Glu Lys Glu Ile Ala Gly Gln Asp Glu Asp His Phe Ile Thr
                        660                 665                 670

Val Asp Ala Val Gly Cys Phe Glu Gly Asp Glu Glu Glu Glu Asp
                        675                 680                 685

Asp Glu Asp Glu Glu Glu Ile Glu Val Glu Glu Leu Cys Lys Gln
            690                 695                 700
```

-continued

```
Val Arg Ser Arg Asp Ile Ser Arg Glu Glu Trp Lys Gly Ser Glu Thr
705                 710                 715                 720

Tyr Ser Pro Asn Thr Ala Tyr Gly Val Asp Phe Leu Val Pro Val Met
            725                 730                 735

Gly Tyr Ile Cys Arg Ile Cys His Lys Phe Tyr His Ser Asn Ser Gly
            740                 745                 750

Ala Gln Leu Ser His Cys Lys Ser Leu Gly His Phe Glu Asn Leu Gln
        755                 760                 765

Lys Tyr Lys Ala Ala Lys Asn Pro Ser Pro Thr Thr Arg Pro Val Ser
770                 775                 780

Arg Arg Cys Ala Ile Asn Ala Arg Asn Ala Leu Thr Ala Leu Phe Thr
785                 790                 795                 800

Ser Ser Gly Arg Pro Pro Ser Gln Pro Asn Thr Gln Asp Lys Thr Pro
            805                 810                 815

Ser Lys Val Thr Ala Arg Pro Ser Gln Pro Pro Leu Pro Arg Arg Ser
            820                 825                 830

Thr Arg Leu Lys Thr
        835

<210> SEQ ID NO 34
<211> LENGTH: 818
<212> TYPE: PRT
<213> ORGANISM: Homo sapiens

<400> SEQUENCE: 34

Met Phe Ser Gln Gln Gln Gln Gln Leu Gln Gln Gln Gln Gln Gln Gln
1               5                   10                  15

Leu Gln Gln Leu Gln Gln Gln Leu Gln Gln Gln Leu Gln Gln Leu Gln
            20                  25                  30

Gln Gln Leu Leu Gln Leu Gln Leu Leu Gln Gln Ser Pro Pro Gln
        35                  40                  45

Ala Pro Leu Pro Met Ala Val Ser Arg Gly Leu Pro Pro Gln Gln Pro
    50                  55                  60

Gln Gln Pro Leu Leu Asn Leu Gln Gly Thr Asn Ser Ala Ser Leu Leu
65                  70                  75                  80

Asn Gly Ser Met Leu Gln Arg Ala Leu Leu Leu Gln Gln Leu Gln Gly
                85                  90                  95

Asn Leu Arg Gly Tyr Gly Met Ala Ser Pro Gly Leu Ala Ala Pro Ser
            100                 105                 110

Leu Thr Pro Pro Gln Leu Ala Thr Pro Asn Leu Gln Gln Phe Phe Pro
        115                 120                 125

Gln Ala Thr Arg Gln Ser Leu Leu Gly Pro Pro Val Gly Val Pro
    130                 135                 140

Met Asn Pro Ser Gln Phe Asn Leu Ser Gly Arg Asn Pro Gln Lys Gln
145                 150                 155                 160

Ala Arg Thr Ser Ser Ser Thr Thr Pro Asn Arg Lys Asp Ser Ser Ser
                165                 170                 175

Gln Thr Met Pro Val Glu Asp Lys Ser Asp Pro Pro Glu Gly Ser Glu
            180                 185                 190

Glu Ala Glu Pro Arg Met Asp Thr Pro Glu Asp Gln Asp Leu Pro
        195                 200                 205

Pro Cys Pro Glu Asp Ile Ala Lys Glu Lys Arg Thr Pro Ala Pro Glu
    210                 215                 220

Pro Glu Pro Cys Glu Ala Ser Glu Leu Pro Ala Lys Arg Leu Arg Ser
225                 230                 235                 240
```

-continued

```
Ser Glu Glu Pro Thr Glu Lys Glu Pro Gly Gln Leu Gln Val Lys
            245             250                 255

Ala Gln Pro Gln Ala Arg Met Thr Val Pro Lys Gln Thr Gln Thr Pro
        260                 265                 270

Asp Leu Leu Pro Glu Ala Leu Glu Ala Gln Val Leu Pro Arg Phe Gln
            275                 280                 285

Pro Arg Val Leu Gln Val Gln Ala Gln Val Gln Ser Gln Thr Gln Pro
    290                 295                 300

Arg Ile Pro Ser Thr Asp Thr Gln Val Gln Pro Lys Leu Gln Lys Gln
305                 310                 315                 320

Ala Gln Thr Gln Thr Ser Pro Glu His Leu Val Leu Gln Lys Gln
                325                 330                 335

Val Gln Pro Gln Leu Gln Gln Glu Ala Glu Pro Gln Lys Gln Val Gln
                340                 345                 350

Pro Gln Val His Thr Gln Ala Gln Pro Ser Val Gln Pro Gln Glu His
            355                 360                 365

Pro Pro Ala Gln Val Ser Val Gln Pro Glu Gln Thr His Glu Gln
    370                 375                 380

Pro His Thr Gln Pro Gln Val Ser Leu Leu Ala Pro Glu Gln Thr Pro
385                 390                 395                 400

Val Val Val His Val Cys Gly Leu Glu Met Pro Pro Asp Ala Val Glu
                405                 410                 415

Ala Gly Gly Gly Met Glu Lys Thr Leu Pro Glu Pro Val Gly Thr Gln
                420                 425                 430

Val Ser Met Glu Glu Ile Gln Asn Glu Ser Ala Cys Gly Leu Asp Val
            435                 440                 445

Gly Glu Cys Glu Asn Arg Ala Arg Glu Met Pro Gly Val Trp Gly Ala
            450                 455                 460

Gly Gly Ser Leu Lys Val Thr Ile Leu Gln Ser Ser Asp Ser Arg Ala
465                 470                 475                 480

Phe Ser Thr Val Pro Leu Thr Pro Val Pro Arg Pro Ser Asp Ser Val
                485                 490                 495

Ser Ser Thr Pro Ala Ala Thr Ser Thr Pro Ser Lys Gln Ala Leu Gln
            500                 505                 510

Phe Phe Cys Tyr Ile Cys Lys Ala Ser Cys Ser Ser Gln Gln Glu Phe
            515                 520                 525

Gln Asp His Met Ser Glu Pro Gln His Gln Arg Leu Gly Glu Ile
    530                 535                 540

Gln His Met Ser Gln Ala Cys Leu Leu Ser Leu Leu Pro Val Pro Arg
545                 550                 555                 560

Asp Val Leu Glu Thr Glu Asp Glu Glu Pro Pro Pro Arg Arg Trp Cys
                565                 570                 575

Asn Thr Cys Gln Leu Tyr Tyr Met Gly Asp Leu Ile Gln His Arg Arg
            580                 585                 590

Thr Gln Asp His Lys Ile Ala Lys Gln Ser Leu Arg Pro Phe Cys Thr
        595                 600                 605

Val Cys Asn Arg Tyr Phe Lys Thr Pro Arg Lys Phe Val Glu His Val
    610                 615                 620

Lys Ser Gln Gly His His Lys Asp Lys Ala Lys Glu Leu Lys Ser Leu Glu
625                 630                 635                 640

Lys Glu Ile Ala Gly Gln Asp Glu Asp His Phe Ile Thr Val Asp Ala
                645                 650                 655
```

```
Val Gly Cys Phe Glu Gly Asp Glu Glu Glu Asp Glu Asp
            660             665             670
Glu Glu Glu Ile Glu Val Glu Glu Leu Cys Lys Gln Val Arg Ser
        675             680             685
Arg Asp Ile Ser Arg Glu Glu Trp Lys Gly Ser Glu Thr Tyr Ser Pro
    690             695             700
Asn Thr Ala Tyr Gly Val Asp Phe Leu Val Pro Val Met Gly Tyr Ile
705             710             715             720
Cys Arg Ile Cys His Lys Phe Tyr His Ser Asn Ser Gly Ala Gln Leu
            725             730             735
Ser His Cys Lys Ser Leu Gly His Phe Glu Asn Leu Gln Lys Tyr Lys
        740             745             750
Ala Ala Lys Asn Pro Ser Pro Thr Thr Arg Pro Val Ser Arg Arg Cys
        755             760             765
Ala Ile Asn Ala Arg Asn Ala Leu Thr Ala Leu Phe Thr Ser Ser Gly
        770             775             780
Arg Pro Pro Ser Gln Pro Asn Thr Gln Asp Lys Thr Pro Ser Lys Val
785             790             795             800
Thr Ala Arg Pro Ser Gln Pro Leu Pro Arg Arg Ser Thr Arg Leu
            805             810             815
Lys Thr

<210> SEQ ID NO 35
<211> LENGTH: 820
<212> TYPE: PRT
<213> ORGANISM: Homo sapiens

<400> SEQUENCE: 35

Pro Leu Pro Met Ala Val Ser Arg Gly Leu Pro Pro Gln Gln Pro Gln
1               5               10              15
Gln Pro Leu Leu Asn Leu Gln Gly Thr Asn Ser Ala Ser Leu Leu Asn
            20              25              30
Gly Ser Met Leu Gln Arg Ala Leu Leu Leu Gln Gln Leu Gln Gly Asn
        35              40              45
Leu Arg Gly Tyr Gly Met Ala Ser Pro Gly Leu Ala Ala Pro Ser Leu
    50              55              60
Thr Pro Pro Gln Leu Ala Thr Pro Asn Leu Gln Gln Phe Phe Pro Gln
65              70              75              80
Ala Thr Arg Gln Ser Leu Leu Gly Pro Pro Val Gly Val Pro Met
            85              90              95
Asn Pro Ser Gln Phe Asn Leu Ser Gly Arg Asn Pro Gln Lys Gln Ala
        100             105             110
Arg Thr Ser Ser Ser Thr Thr Pro Asn Arg Lys Thr Met Pro Val Glu
    115             120             125
Asp Lys Ser Asp Pro Pro Glu Gly Ser Glu Glu Ala Ala Glu Pro Arg
130             135             140
Met Asp Thr Pro Glu Asp Gln Asp Leu Pro Cys Pro Glu Asp Ile
145             150             155             160
Ala Lys Glu Lys Arg Thr Pro Ala Pro Glu Pro Glu Pro Cys Glu Ala
            165             170             175
Ser Glu Leu Pro Ala Lys Arg Leu Arg Ser Ser Glu Glu Pro Thr Glu
        180             185             190
Lys Glu Pro Pro Gly Gln Leu Gln Val Lys Ala Gln Pro Gln Ala Arg
    195             200             205
```

Met Thr Val Pro Lys Gln Thr Gln Thr Pro Asp Leu Leu Pro Glu Ala
210                 215                 220

Leu Glu Ala Gln Val Leu Pro Arg Phe Gln Pro Arg Val Leu Gln Val
225                 230                 235                 240

Gln Ala Gln Val Gln Ser Gln Thr Gln Pro Arg Ile Pro Ser Thr Asp
                245                 250                 255

Thr Gln Val Gln Pro Lys Leu Gln Lys Gln Ala Gln Thr Gln Thr Ser
            260                 265                 270

Pro Glu His Leu Val Leu Gln Gln Lys Gln Val Gln Pro Gln Leu Gln
        275                 280                 285

Gln Glu Ala Glu Pro Gln Lys Gln Val Gln Pro Gln Val Gln Pro Gln
290                 295                 300

Ala His Ser Gln Gly Pro Arg Gln Val Gln Leu Gln Gln Glu Ala Glu
305                 310                 315                 320

Pro Leu Lys Gln Val Gln Pro Gln Val Gln Pro Gln Ala His Ser Gln
                325                 330                 335

Pro Pro Arg Gln Val Gln Leu Gln Leu Gln Lys Gln Val Gln Thr Gln
            340                 345                 350

Thr Tyr Pro Gln Val His Thr Gln Ala Gln Pro Ser Val Gln Pro Gln
        355                 360                 365

Glu His Pro Pro Ala Gln Val Ser Val Gln Pro Pro Glu Gln Thr His
370                 375                 380

Glu Gln Pro His Thr Gln Pro Gln Val Ser Leu Leu Ala Pro Glu Gln
385                 390                 395                 400

Thr Pro Val Val His Val Cys Gly Leu Glu Met Pro Pro Asp Ala
                405                 410                 415

Val Glu Ala Gly Gly Ser Met Glu Lys Thr Leu Pro Glu Pro Val Gly
            420                 425                 430

Thr Gln Val Ser Met Glu Glu Ile Gln Asn Glu Ser Ala Cys Gly Leu
        435                 440                 445

Asp Val Gly Glu Cys Glu Asn Arg Ala Arg Glu Met Pro Gly Val Trp
450                 455                 460

Gly Ala Gly Gly Ser Leu Lys Val Thr Ile Leu Gln Ser Ser Asp Ser
465                 470                 475                 480

Arg Ala Phe Ser Thr Val Pro Leu Thr Pro Val Pro Arg Pro Ser Asp
                485                 490                 495

Ser Val Ser Ser Thr Pro Ala Ala Thr Ser Thr Pro Ser Lys Gln Ala
            500                 505                 510

Leu Gln Phe Phe Cys Tyr Ile Cys Lys Ala Ser Cys Ser Ser Gln Gln
        515                 520                 525

Glu Phe Gln Asp His Met Ser Glu Pro Gln His Gln Gln Arg Leu Gly
530                 535                 540

Glu Ile Gln His Met Ser Gln Ala Cys Leu Leu Ser Leu Leu Pro Val
545                 550                 555                 560

Pro Arg Asp Val Leu Glu Thr Glu Asp Glu Pro Pro Arg Arg
                565                 570                 575

Trp Cys Asn Thr Cys Gln Leu Tyr Tyr Met Gly Asp Leu Ile Gln His
            580                 585                 590

Arg Arg Thr Gln Asp His Arg Ile Ala Lys Gln Ser Leu Arg Pro Phe
        595                 600                 605

Cys Thr Val Cys Asn Arg Tyr Phe Lys Thr Pro Arg Lys Phe Val Glu
610                 615                 620

His Val Lys Ser Gln Gly His Lys Asp Lys Ala Lys Glu Leu Lys Ser

```
               625                 630                 635                 640
Leu Glu Lys Glu Ile Ala Gly Gln Asp Glu His Phe Ile Thr Val
                645                 650                 655

Asp Ala Val Gly Cys Phe Glu Gly Asp Glu Glu Glu Glu Asp Asp
                660                 665                 670

Glu Asp Glu Glu Ile Glu Val Glu Glu Leu Cys Lys Gln Val
        675                 680                 685

Arg Ser Arg Asp Ile Ser Arg Glu Glu Trp Lys Gly Ser Glu Thr Tyr
        690                 695                 700

Ser Pro Asn Thr Ala Tyr Gly Val Asp Phe Leu Val Pro Val Met Gly
705                 710                 715                 720

Tyr Ile Cys Arg Ile Cys His Lys Phe Tyr His Asn Asn Ser Gly Ala
                725                 730                 735

Gln Leu Ser His Cys Lys Ser Leu Gly His Phe Glu Asn Leu Gln Lys
                740                 745                 750

Tyr Lys Ala Ala Lys Asn Pro Ser Pro Thr Thr Arg Pro Val Ser Arg
                755                 760                 765

Arg Cys Ala Ile Asn Ala Arg Asn Ala Leu Thr Ala Leu Phe Thr Ser
        770                 775                 780

Ser Gly Arg Pro Pro Ser Gln Pro Asn Thr Gln Asp Lys Thr Pro Ser
785                 790                 795                 800

Lys Val Thr Ala Arg Pro Ser Gln Pro Leu Pro Arg Arg Ser Thr
                805                 810                 815

Arg Leu Lys Thr
            820

<210> SEQ ID NO 36
<211> LENGTH: 391
<212> TYPE: PRT
<213> ORGANISM: Homo sapiens

<400> SEQUENCE: 36

Met Phe Ser Gln Gln Gln Gln Gln Leu Gln Gln Gln Gln Gln Gln
1               5                   10                  15

Leu Gln Gln Leu Gln Gln Gln Leu Gln Gln Gln Gln Leu Gln Gln
                20                  25                  30

Gln Gln Leu Leu Gln Leu Gln Gln Leu Leu Gln Gln Ser Pro Pro Gln
                35                  40                  45

Ala Pro Leu Pro Met Ala Val Ser Arg Gly Leu Pro Pro Gln Gln Pro
        50                  55                  60

Gln Gln Pro Leu Leu Asn Leu Gln Gly Thr Asn Ser Ala Ser Leu Leu
65                  70                  75                  80

Asn Gly Ser Met Leu Gln Arg Ala Leu Leu Gln Gln Leu Gln Gly
                85                  90                  95

Asn Leu Arg Gly Tyr Gly Met Ala Ser Pro Gly Leu Ala Ala Pro Ser
                100                 105                 110

Leu Thr Pro Pro Gln Leu Ala Thr Pro Asn Leu Gln Gln Phe Pro
                115                 120                 125

Gln Ala Thr Arg Gln Ser Leu Leu Gly Pro Pro Val Gly Val Pro
        130                 135                 140

Met Asn Pro Ser Gln Phe Asn Leu Ser Gly Arg Asn Pro Gln Lys Gln
145                 150                 155                 160

Ala Arg Thr Ser Ser Ser Thr Pro Asn Arg Lys Asp Ser Ser Ser
                165                 170                 175
```

```
Gln Thr Met Pro Val Glu Asp Lys Ser Asp Pro Glu Gly Ser Glu
            180                 185                 190

Glu Ala Ala Glu Pro Arg Met Asp Thr Pro Glu Asp Gln Asp Leu Pro
        195                 200                 205

Pro Cys Pro Glu Asp Ile Ala Lys Glu Lys Arg Thr Pro Ala Pro Glu
    210                 215                 220

Pro Glu Pro Cys Glu Ala Ser Glu Leu Pro Ala Lys Arg Leu Arg Ser
225                 230                 235                 240

Ser Glu Glu Pro Thr Glu Lys Glu Pro Pro Gly Gln Leu Gln Val Lys
                245                 250                 255

Ala Gln Pro Gln Ala Arg Met Thr Val Pro Lys Gln Thr Gln Thr Pro
            260                 265                 270

Asp Leu Leu Pro Glu Ala Leu Glu Ala Gln Val Leu Pro Arg Phe Gln
        275                 280                 285

Pro Arg Val Leu Gln Val Gln Ala Gln Val Gln Ser Gln Thr Gln Pro
    290                 295                 300

Arg Ile Pro Ser Thr Asp Thr Gln Val Gln Pro Lys Leu Gln Lys Gln
305                 310                 315                 320

Ala Gln Thr Gln Thr Ser Pro Glu His Leu Val Leu Gln Gln Lys Gln
                325                 330                 335

Val Gln Pro Gln Leu Gln Glu Ala Glu Pro Gln Lys Gln Val Gln
            340                 345                 350

Pro Gln Val Gln Pro Gln Ala His Ser Gln Gly Pro Arg Gln Val Gln
        355                 360                 365

Leu Gln Gln Glu Ala Glu Pro Leu Lys Gln Val Gln Pro Gln Val Gln
    370                 375                 380

Pro Gln Ala His Ser Gln Pro
385                 390

<210> SEQ ID NO 37
<211> LENGTH: 75
<212> TYPE: PRT
<213> ORGANISM: Homo sapiens

<400> SEQUENCE: 37

Leu Gln Gln Gln Gln Gln Leu Gln Gln Leu Gln Gln Gln Gln Leu
1               5                   10                  15

Gln Gln Gln Gln Leu Gln Gln Gln Leu Leu Gln Leu Gln Gln Leu
                20                  25                  30

Leu Gln Gln Ser Pro Pro Gln Ala Pro Leu Pro Met Ala Val Ser Arg
            35                  40                  45

Gly Leu Pro Pro Gln Gln Pro Gln Pro Leu Leu Asn Leu Gln Gly
    50                  55                  60

Thr Asn Ser Ala Ser Leu Leu Asn Gly Ser Met
65                  70                  75

<210> SEQ ID NO 38
<211> LENGTH: 33
<212> TYPE: PRT
<213> ORGANISM: Homo sapiens

<400> SEQUENCE: 38

Gln Gln Leu Gln Gln Leu Gln Gln Gln Leu Gln Gln Gln Gln Leu
1               5                   10                  15

Gln Gln Gln Gln Leu Leu Gln Leu Gln Gln Leu Leu Gln Gln Ser Pro
                20                  25                  30
```

Pro

<210> SEQ ID NO 39
<211> LENGTH: 52
<212> TYPE: PRT
<213> ORGANISM: Homo sapiens

<400> SEQUENCE: 39

Met Phe Ser Gln Gln Gln Gln Gln Leu Gln Gln Gln Gln Gln
1               5                   10                  15

Leu Gln Gln Leu Gln Gln Gln Leu Gln Gln Gln Leu Gln Gln
                20                  25                  30

Gln Gln Leu Leu Gln Leu Gln Gln Leu Leu Gln Gln Ser Pro Pro Gln
            35                  40                  45

Ala Pro Leu Pro
    50

<210> SEQ ID NO 40
<211> LENGTH: 26
<212> TYPE: PRT
<213> ORGANISM: Homo sapiens

<400> SEQUENCE: 40

Pro Pro Thr Pro Arg Arg Asp Val Phe Ala His Val Pro Val Gln Gly
1               5                   10                  15

Trp Ser Thr Ala Arg Leu Val Thr Asp Met
                20                  25

<210> SEQ ID NO 41
<211> LENGTH: 24
<212> TYPE: PRT
<213> ORGANISM: Homo sapiens

<400> SEQUENCE: 41

Gly Leu Asp Gln Phe Ala Met Pro Pro Ala Thr Tyr Asp Thr Ala Gly
1               5                   10                  15

Leu Thr Met Pro Thr Ala Thr Leu
                20

<210> SEQ ID NO 42
<211> LENGTH: 56
<212> TYPE: PRT
<213> ORGANISM: Homo sapiens

<400> SEQUENCE: 42

Pro Gln Val Gln Pro Gln Ala His Ser Gln Gly Pro Arg Gln Val Gln
1               5                   10                  15

Leu Gln Gln Glu Ala Glu Pro Leu Lys Gln Val Gln Pro Gln Val Gln
                20                  25                  30

Pro Gln Ala His Ser Gln Pro Pro Arg Gln Val Gln Leu Gln Leu Gln
            35                  40                  45

Lys Gln Val Gln Thr Gln Thr Tyr
    50                  55

<210> SEQ ID NO 43
<211> LENGTH: 28
<212> TYPE: PRT
<213> ORGANISM: Homo sapiens

<400> SEQUENCE: 43

Pro Gln Val Gln Pro Gln Ala His Ser Gln Pro Pro Arg Gln Val Gln

```
                1               5                      10                     15
Leu Gln Leu Gln Lys Gln Val Gln Thr Gln Thr Tyr
            20                     25

<210> SEQ ID NO 44
<211> LENGTH: 112
<212> TYPE: PRT
<213> ORGANISM: Homo sapiens

<400> SEQUENCE: 44

Gln Val Gln Ser Gln Thr Gln Pro Arg Ile Pro Ser Thr Asp Thr Gln
1               5                      10                     15

Val Gln Pro Lys Leu Gln Lys Gln Ala Gln Thr Gln Thr Ser Pro Glu
            20                     25                     30

His Leu Val Leu Gln Gln Lys Gln Val Gln Pro Gln Leu Gln Gln Glu
        35                     40                     45

Ala Glu Pro Gln Lys Gln Val Gln Pro Gln Val Gln Pro Gln Ala His
    50                     55                     60

Ser Gln Gly Pro Arg Gln Val Gln Leu Gln Gln Glu Ala Glu Pro Leu
65                  70                     75                     80

Lys Gln Val Gln Pro Gln Val Gln Pro Gln Ala His Ser Gln Pro Pro
                85                     90                     95

Arg Gln Val Gln Leu Gln Leu Gln Lys Gln Val Gln Thr Gln Thr Tyr
            100                    105                    110

<210> SEQ ID NO 45
<211> LENGTH: 2687
<212> TYPE: DNA
<213> ORGANISM: Mus musculus

<400> SEQUENCE: 45
catgttcaac ccgcaactcc agcagcagca acagttgcag cagcagcagc aacagttgca      60
gcagcagctc cagcagcagc agctccagca gcagcaacag cagatactgc agctccaaca     120
gctgctgcaa cagtccccac cacaggcctc cttgtccatt cctgtcagcc ggggcctccc     180
ccagcagtca tccccgcaac agcttctgag tctccaggga ctccactcga cctccctgct     240
caatggcccc atgctgcaaa gagctttgct cctacagcag ttgcaaggac tggaccagtt     300
tgcaatgcca ccagccacgt atgacggtgc agcctcacc atgcctacgg caacactggg      360
taacctccgt gctttcaatg tgacagcccc aagcctagca gctcccagcc ttacaccacc     420
ccagatggtc accccaaatc tgcagcagtt cttcccag gctactcgac agtctctgct       480
ggggcctcct cctgttgggg tcccaataaa cccttctcag ctcaaccact cagggaggaa     540
cacccagaaa caggccagaa ccccctcttc caccaccccc aatcgcaagg attcttcttc     600
tcagacggtg cctctggaag acagggaaga ccccacagag gggtctgagg aagccacgga     660
gctccagatg gacacatgtg aagaccaaga ttcactagtc ggtccagata gcatgctgag     720
tgagccccaa gtgcctgagc ctgagccctt tgagacattg gaaccaccag ccaagaggtg     780
caggagctca gaggagtcca ccgagaaagg ccctacaggg cagccacaag caagggtcca     840
gcctcagacc cagatgacag caccaaagca gacacagacc ccggatcggc tgcctgagcc     900
accagaagtc caaatgctgc cgcgtatcca gccacaggca ctgcagatcc agacccagcc     960
aaagctgctg aggcaggcac agacacagac ctctccagag cacttagcgc cccagcagga    1020
tcaggtagag ccacaggtac catcacagcc ccatggcag ttgcagccac gggagacaga     1080
cccaccgaac caagctcagg cacagaccca gcctcagccc ctctggcagg cgcagtcaca    1140
```

```
gaagcaggcc cagacacagg cacatccaca ggtacccacc caagcacagt cacaggagca      1200
gacatcagag aagacccagg accagcctca gacctggcca caggggtcag taccccccacc     1260 agaacaagcg tcaggtccag cctgtgccac ggaaccacag ctatcctctc acgctgcaga      1320
agctgggagt gacccagaca aggccttgcc agaaccagta agtgcccaga gcagtgaaga      1380
caggagccgg gaggcgtccg ctggtggcct ggatttggga gaatgtgaaa agagagcggg     1440
agagatgctg gggatgtggg gggctgggag ctccctgaag gtcaccatcc tgcagagtag      1500
caacagccgg gcctttaaca ccacaccccct cacatctgga cctcgccctg ggactctac     1560 ctctgccacc cctgccattg ccagcacacc ctccaagcaa agcctccagt tcttctgcta      1620
catctgcaag gccagcagca gcagccagca ggagttccag gatcacatgt cagaggctca      1680
gcaccaacag cggcttgggg aaatacaaca ctcgagccag acctgcctgc tgtccctgct     1740
gcccatgcct cgggacatcc tggagaaaga agcggaagat cctccgccca acgctggtg      1800 caacacctgc caggtgtact acgtgggaga cttgatccag caccgtagga cacaggagca     1860
caaggttgcc aaacaatccc tgaggccctt ctgcaccata tgcaaccgtt acttcaagac     1920
ccctcgaaag tttgtggagc acgtgaagtc ccagggacac aaggacaagg cccaagagct      1980
gaagacactt gaaaggaga caggcagccc agatgaggac cacttcatca ctgtggacgc       2040
cgtcggttgc tttgagagtg gtcaagaaga ggacgaggat gacgacgagg aagaagaaga     2100
agaaggagag attgaggctg aggaggaatt ctgcaagcag gtgaagccga gaaacatc      2160 ctcagagcaa gggaagggct ctgagacgta caaccccaac acagcctatg gtgaggattt      2220
cctggtgcca gtgatgggct atgtctgtca aatctgtcac aagttctacg acagcaactc     2280
agaattgcgg ctttctcact gcaagtccct ggcccacttt gagaacctgc agaaatacaa     2340
agccaagaac ccaagccctc ctcctacccg gcctgtgagc cgcaagtgtg ccatcaacgc    2400
ccgcaacgcc ctgactgcac tgttcacctc tagccaccag cccagccccc aggacacagt     2460
gaaaatgccc agcaaggtga agcctggatc ccccggactc cctcctcccc ttcggcgctc    2520
aacacgcctc aaaacctgat agagggagct ctggccactc agcctgacta aggctcagtc     2580
tgctaatgct tcctaggtat ctgtgtagaa atgttcaagt ggttggtgtt tttactcaaa     2640
atccaataaa gagtcagtag tttggcaaaa aaaaaaaaaa aaaaaaa                  2687
```

<210> SEQ ID NO 46  
<211> LENGTH: 2922  
<212> TYPE: DNA  
<213> ORGANISM: Homo sapiens

<400> SEQUENCE: 46

```
tgggggctgc ggggccggcc catccgtggg ggcgacttga gcgttgaggg cgcgcgggga        60
ggcgagccac catgttcagc cagcagcagc agcagctcca gcaacagcag cagcagctcc       120
agcagttaca gcagcagcag ctccagcagc agcaattgca gcagcagcag ttactgcagc       180
tccagcagct gctccagcag tccccaccac aggccccgtt gcccatggct gtcagccggg      240
ggctcccccc gcagcagcca cagcagccgc ttctgaatct ccagggcacc aactcagcct       300
ccctcctcaa cggctccatg ctgcagagag cttttgctttt acagcagttg caaggactgg      360
accagtttgc aatgccacca gccacgtatg acactgccgg tctcaccatg cccacagcaa       420
cactgggtaa cctccgaggc tatggcatgg catcccagg cctcgcagcc ccagcctca       480 cacccccaca actggccact ccaaatttgc aacagttctt tccccaggcc actcgccagt      540
```

-continued

```
ccttgctggg acctcctcct gttggggtcc ccatgaaccc ttcccagttc aacctttcag    600
gacggaaccc ccagaaacag gcccggacct cctcctctac cacccccaat cgaaaggatt    660
cttcttctca gacaatgcct gtggaagaca agtcagaccc cccagagggg tctgaggaag    720
ccgcagagcc ccgatggac acaccagaag accaagattt accgccctgc ccagaggaca    780
tcgccaagga aaacgcact ccagcacctg agcctgagcc ttgtgaggcg tccgagctgc    840
cagcaaagag attgaggagc tcagaagagc ccacagagaa ggaacctcca gggcagttac    900
aggtgaaggc ccagccgcag gcccggatga cagtaccgaa acagacacag acaccagacc    960
tgctgcctga ggccctggaa gcccaagtgc tgccacgatt ccagccacgg gtcctgcagg   1020
tccaggccca ggtgcagtca cagactcagc cgcggatacc atccacagac acccaggtgc   1080
agccaaagct gcagaagcag gcgcaaacac agacctctcc agagcactta gtgctgcaac   1140
agaagcaggt gcagccacag ctgcagcagg aggcagagcc acagaagcag gtgcagccac   1200
aggtacagcc acaggcacat tcacagggcc caaggcaggt gcagctgcag caggaggcag   1260
agccgctgaa gcaggtgcag ccacaggtgc agccccaggc acattcacag cccccaaggc   1320
aggtgcagct gcagctgcag aagcaggtcc agacacagac atatccacag gtccacacac   1380
aggcacagcc aagcgtccag ccacaggagc atcctccagc gcaggtgtca gtacagccac   1440
cagagcagac ccatgagcag cctcacaccc agccgcaggt gtcgttgctg gctccagagc   1500
aaacaccagt tgtggttcat gtctgcgggc tggagatgcc acctgatgca gtagaagctg   1560
gtggaggcat ggaaaagacc ttgccagagc ctgtgggcac ccaagtcagc atggaagaga   1620
ttcagaatga gtcggcctgt ggcctagatg tgggagaatg tgaaaacaga gcgagagaga   1680
tgccaggggt atggggcgcc gggggctccc tgaaggtcac cattctgcag agcagtgaca   1740
gccgggcctt tagcactgta cccctgacac ctgtcccccg ccccagtgac tccgtctcct   1800
ccacccctgc ggctaccagc actccctcta agcaggccct ccagttcttc tgctacatct   1860
gcaaggccag ctgctccagc cagcaggagt tccaggacca catgtcggag cctcagcacc   1920
agcagcggct aggggagatc cagcacatga gccaagcctg cctcctgtcc ctgctgcccg   1980
tgccccggga cgtcctggag acagaggatg aggagcctcc accaaggcgc tggtgcaaca   2040
cctgccagct ctactacatg ggggacctga tccaacaccg caggacacag gaccacaaga   2100
ttgccaaaca atccttgcga cccttctgca ccgtttgcaa ccgctacttc aaaaccctc    2160
gcaagtttgt ggagcacgtg aagtcccagg ggcataagga caaagccaag gagctgaagt   2220
cgcttgagaa agaaattgct ggccaagatg aggaccactt cattacagtg gacgctgtgg   2280
gttgcttcga gggtgatgaa gaagaggaag aggatgatga ggatgaagaa gagatcgagg   2340
ttgaggagga actctgcaag caggtgaggt ccagagatat atccagagag gagtggaagg   2400
gctcggagac ctacagcccc aatactgcat atggtgtgga cttcctggtg cccgtgatgg   2460
gctatatctg ccgcatctgc cacaagttct atcacagcaa ctcagggggca cagctctccc   2520
actgcaagtc cctgggccac tttgagaacc tgcagaaata caaggcggcc aagaacccca   2580
gccccaccac ccgacctgtg agccgccggt gcgcaatcaa cgcccggaac gctttgacag   2640
ccctgttcac ctccagcggc cgccaccct cccagcccaa cacccaggac aaaacaccca   2700
gcaaggtgac ggctcgaccc tcccagcccc cactacctcg gcgctcaacc cgcctcaaaa   2760
cctgatagag ggacctccct gtccctggcc tgcctgggtc cagatctgct aatgcttttt   2820
aggagtctgc ctgaaaactt tgacatggtt catgttttta ctcaaaatcc aataaaacaa   2880
ggtagtttgg ctgtgcaaaa aaaaaaaaa aaaaaaaaa aa                         2922
```

<210> SEQ ID NO 47
<211> LENGTH: 897
<212> TYPE: PRT
<213> ORGANISM: Homo sapiens

<400> SEQUENCE: 47

```
Met Phe Ser Gln Gln Gln Gln Leu Gln Gln Gln Gln Gln Gln Gln Leu
1               5                   10                  15

Gln Gln Leu Gln Gln Gln Leu Gln Gln Gln Leu Gln Gln Gln Leu Gln Gln
            20                  25                  30

Gln Leu Leu Gln Leu Gln Gln Leu Leu Gln Gln Ser Pro Pro Gln Ala
        35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
        115                 120                 125

Pro Gly Leu Ala Ala Pro Ser Leu Thr Pro Pro Gln Leu Ala Thr Pro
    130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Ser Gln Thr Met Pro Val Glu Asp Lys Ser
        195                 200                 205

Asp Pro Pro Glu Gly Ser Glu Glu Ala Ala Glu Pro Arg Met Asp Thr
    210                 215                 220

Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
            260                 265                 270

Pro Gly Gln Leu Gln Val Lys Ala Gln Pro Gln Ala Arg Met Thr Val
        275                 280                 285

Pro Lys Gln Thr Gln Thr Pro Asp Leu Leu Pro Glu Ala Leu Glu Ala
    290                 295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
                325                 330                 335

Gln Pro Lys Leu Gln Lys Gln Ala Gln Thr Gln Thr Ser Pro Glu His
            340                 345                 350

Leu Val Leu Gln Gln Lys Gln Val Gln Pro Gln Leu Gln Gln Glu Ala
        355                 360                 365

Glu Pro Gln Lys Gln Val Gln Pro Gln Val Gln Pro Gln Ala His Ser
```

```
                    370                 375                 380
Gln Gly Pro Arg Gln Val Gln Leu Gln Gln Glu Ala Glu Pro Leu Lys
385                 390                 395                 400

Gln Val Gln Pro Gln Val Gln Pro Gln Ala His Ser Gln Pro Pro Arg
                405                 410                 415

Gln Val Gln Leu Gln Leu Gln Lys Gln Val Gln Thr Gln Thr Tyr Pro
                420                 425                 430

Gln Val His Thr Gln Ala Gln Pro Ser Val Gln Pro Gln Glu His Pro
            435                 440                 445

Pro Ala Gln Val Ser Val Gln Pro Glu Gln Thr His Glu Gln Pro
450                 455                 460

His Thr Gln Pro Gln Val Ser Leu Leu Ala Pro Glu Gln Thr Pro Val
465                 470                 475                 480

Val Val His Val Cys Gly Leu Glu Met Pro Pro Asp Ala Val Glu Ala
                485                 490                 495

Gly Gly Gly Met Glu Lys Thr Leu Pro Glu Pro Val Gly Thr Gln Val
            500                 505                 510

Ser Met Glu Glu Ile Gln Asn Glu Ser Ala Cys Gly Leu Asp Val Gly
            515                 520                 525

Glu Cys Glu Asn Arg Ala Arg Glu Met Pro Gly Val Trp Gly Ala Gly
530                 535                 540

Gly Ser Leu Lys Val Thr Ile Leu Gln Ser Ser Asp Ser Arg Ala Phe
545                 550                 555                 560

Ser Thr Val Pro Leu Thr Pro Val Pro Arg Pro Ser Asp Ser Val Ser
                565                 570                 575

Ser Thr Pro Ala Ala Thr Ser Thr Pro Ser Lys Gln Ala Leu Gln Phe
            580                 585                 590

Phe Cys Tyr Ile Cys Lys Ala Ser Cys Ser Ser Gln Gln Glu Phe Gln
            595                 600                 605

Asp His Met Ser Glu Pro Gln His Gln Arg Leu Gly Glu Ile Gln
610                 615                 620

His Met Ser Gln Ala Cys Leu Leu Ser Leu Leu Pro Val Pro Arg Asp
625                 630                 635                 640

Val Leu Glu Thr Glu Asp Glu Pro Pro Arg Arg Trp Cys Asn
                645                 650                 655

Thr Cys Gln Leu Tyr Tyr Met Gly Asp Leu Ile Gln His Arg Arg Thr
            660                 665                 670

Gln Asp His Lys Ile Ala Lys Gln Ser Leu Arg Pro Phe Cys Thr Val
            675                 680                 685

Cys Asn Arg Tyr Phe Lys Thr Pro Arg Lys Phe Val Glu His Val Lys
690                 695                 700

Ser Gln Gly His His Lys Asp Lys Ala Lys Glu Leu Lys Ser Leu Glu Lys
705                 710                 715                 720

Glu Ile Ala Gly Gln Asp Glu Asp His Phe Ile Thr Val Asp Ala Val
                725                 730                 735

Gly Cys Phe Glu Gly Asp Glu Glu Glu Asp Glu Asp Glu
            740                 745                 750

Glu Glu Ile Glu Val Glu Glu Leu Cys Lys Gln Val Arg Ser Arg
            755                 760                 765

Asp Ile Ser Arg Glu Glu Trp Lys Gly Ser Gly Thr Tyr Ser Pro Asn
            770                 775                 780

Thr Ala Tyr Gly Val Asp Phe Leu Val Pro Val Met Gly Tyr Ile Cys
785                 790                 795                 800
```

```
Arg Ile Cys His Lys Phe Tyr His Ser Asn Ser Gly Ala Gln Leu Ser
                805                 810                 815

His Cys Lys Ser Leu Gly His Phe Glu Asn Leu Gln Lys Tyr Lys Ala
            820                 825                 830

Ala Lys Asn Pro Ser Pro Thr Thr Arg Pro Val Ser Arg Arg Cys Ala
            835                 840                 845

Ile Asn Ala Arg Asn Ala Leu Thr Ala Leu Phe Thr Ser Ser Gly Arg
        850                 855                 860

Pro Pro Ser Gln Pro Asn Thr Gln Asp Lys Thr Pro Ser Lys Val Thr
865                 870                 875                 880

Ala Arg Pro Ser Gln Pro Pro Leu Pro Arg Arg Ser Thr Arg Leu Lys
                885                 890                 895

Thr

<210> SEQ ID NO 48
<211> LENGTH: 49
<212> TYPE: PRT
<213> ORGANISM: Homo sapiens

<400> SEQUENCE: 48

Met Phe Ser Gln Gln Gln Gln Gln Leu Gln Gln Gln Gln Gln Gln Gln
1               5                   10                  15

Leu Gln Gln Leu Gln Gln Gln Gln Leu Gln Gln Gln Gln Leu Gln Gln
            20                  25                  30

Gln Gln Leu Leu Gln Leu Gln Gln Leu Leu Gln Gln Ser Pro Pro Gln
        35                  40                  45

Ala

<210> SEQ ID NO 49
<211> LENGTH: 215
<212> TYPE: DNA
<213> ORGANISM: Homo sapiens

<400> SEQUENCE: 49
tgggggctgc ggggccggcc catccgtggg ggcgacttga gcgttgaggg cgcgcgggga    60
ggcgagccac catgttcagc cagcagcagc agcagctcca gcaacagcag cagcagctcc   120
agcagttaca gcagcagcag ctccagcagc agcaattgca gcagcagcag ttactgcagc   180
tccagcagct gctccagcag tccccaccac aggcc                             215

<210> SEQ ID NO 50
<211> LENGTH: 101
<212> TYPE: DNA
<213> ORGANISM: Homo sapiens

<400> SEQUENCE: 50
cagcagctcc agcagttaca gcagcagcag ctccagcagc agcaattgca gcagcagcag    60
ttactgcagc tccagcagct gctccagcag tccccaccac a                       101

<210> SEQ ID NO 51
<211> LENGTH: 72
<212> TYPE: DNA
<213> ORGANISM: Homo sapiens

<400> SEQUENCE: 51
ggactggacc agtttgcaat gccaccagcc acgtatgaca ctgccggtct caccatgccc    60
acagcaacac tg                                                       72
```

<210> SEQ ID NO 52
<211> LENGTH: 15
<212> TYPE: DNA
<213> ORGANISM: Homo sapiens

<400> SEQUENCE: 52
aggattcttc ttctc                                                  15

<210> SEQ ID NO 53
<211> LENGTH: 86
<212> TYPE: DNA
<213> ORGANISM: Homo sapiens

<400> SEQUENCE: 53
ccacaggtgc agccccaggc acattcacag cccccaaggc aggtgcagct gcagctgcag    60
aagcaggtcc agacacagac atatcc                                        86

<210> SEQ ID NO 54
<211> LENGTH: 168
<212> TYPE: DNA
<213> ORGANISM: Homo sapiens

<400> SEQUENCE: 54
ccacaggtac agccacaggc acattcacag ggcccaaggc aggtgcagct gcagcaggag    60
gcagagccgc tgaagcaggt gcagccacag gtgcagcccc aggcacattc acagccccca   120
aggcaggtgc agctgcagct gcagaagcag gtccagacac agacatat                168

<210> SEQ ID NO 55
<211> LENGTH: 336
<212> TYPE: DNA
<213> ORGANISM: Homo sapiens

<400> SEQUENCE: 55
caggtgcagt cacagactca gccgcggata ccatccacag acacccaggt gcagccaaag    60
ctgcagaagc aggcgcaaac acagacctct ccagagcact tagtgctgca acagaagcag   120
gtgcagccac agctgcagca ggaggcagag ccacagaagc aggtgcagcc acaggtacag   180
ccacaggcac attcacaggg cccaaggcag gtgcagctgc agcaggaggc agagccgctg   240
aagcaggtgc agccacaggt gcagcccag gcacattcac agcccccaag gcaggtgcag    300
ctgcagctgc agaagcaggt ccagacacag acatat                             336

<210> SEQ ID NO 56
<211> LENGTH: 24
<212> TYPE: DNA
<213> ORGANISM: Homo sapiens

<400> SEQUENCE: 56
gttgaggagg aactctgcaa gcag                                          24

<210> SEQ ID NO 57
<211> LENGTH: 78
<212> TYPE: DNA
<213> ORGANISM: Homo sapiens

<400> SEQUENCE: 57
gccacccaca ccacgaagag atgtgtttgc ccacgttcca gtgcaggggt ggagcacagc    60
ccggcttgtt acagatat                                                 78

```
<210> SEQ ID NO 58
<211> LENGTH: 863
<212> TYPE: PRT
<213> ORGANISM: Homo sapiens

<400> SEQUENCE: 58

Met Phe Ser Gln Gln Gln Gln Leu Gln Gln Gln Gln Gln Gln Ala Pro
1               5                   10                  15

Leu Pro Met Ala Val Ser Arg Gly Leu Pro Pro Gln Gln Pro Gln Gln
                20                  25                  30

Pro Leu Leu Asn Leu Gln Gly Thr Asn Ser Ala Ser Leu Leu Asn Gly
            35                  40                  45

Ser Met Leu Gln Arg Ala Leu Leu Gln Gln Leu Gln Gly Leu Asp
    50                  55                  60

Gln Phe Ala Met Pro Pro Ala Thr Tyr Asp Thr Ala Gly Leu Thr Met
65                  70                  75                  80

Pro Thr Ala Thr Leu Gly Asn Leu Arg Gly Tyr Gly Met Ala Ser Pro
                85                  90                  95

Gly Leu Ala Ala Pro Ser Leu Thr Pro Pro Gln Leu Ala Thr Pro Asn
            100                 105                 110

Leu Gln Gln Phe Phe Pro Gln Ala Thr Arg Gln Ser Leu Leu Gly Pro
        115                 120                 125

Pro Pro Val Gly Val Pro Met Asn Pro Ser Gln Phe Asn Leu Ser Gly
    130                 135                 140

Arg Asn Pro Gln Lys Gln Ala Arg Thr Ser Ser Ser Thr Thr Pro Asn
145                 150                 155                 160

Arg Lys Asp Ser Ser Ser Gln Thr Met Pro Val Glu Asp Lys Ser Asp
                165                 170                 175

Pro Pro Glu Gly Ser Glu Glu Ala Ala Glu Pro Arg Met Asp Thr Pro
            180                 185                 190

Glu Asp Gln Asp Leu Pro Pro Cys Pro Glu Asp Ile Ala Lys Glu Lys
        195                 200                 205

Arg Thr Pro Ala Pro Glu Pro Glu Pro Cys Glu Ala Ser Glu Leu Pro
    210                 215                 220

Ala Lys Arg Leu Arg Ser Ser Glu Glu Pro Thr Glu Lys Glu Pro Pro
225                 230                 235                 240

Gly Gln Leu Gln Val Lys Ala Gln Pro Gln Ala Arg Met Thr Val Pro
                245                 250                 255

Lys Gln Thr Gln Thr Pro Asp Leu Leu Pro Glu Ala Leu Glu Ala Gln
            260                 265                 270

Val Leu Pro Arg Phe Gln Pro Arg Val Leu Gln Val Gln Ala Gln Val
        275                 280                 285

Gln Ser Gln Thr Gln Pro Arg Ile Pro Ser Thr Asp Thr Gln Val Gln
    290                 295                 300

Pro Lys Leu Gln Lys Gln Ala Gln Thr Gln Thr Ser Pro Glu His Leu
305                 310                 315                 320

Val Leu Gln Gln Lys Gln Val Gln Pro Gln Leu Gln Gln Ala Glu
                325                 330                 335

Pro Gln Lys Gln Val Pro Val Gln Pro Gln Ala His Ser Gln
            340                 345                 350

Gly Pro Arg Gln Val Gln Leu Gln Gln Glu Ala Glu Pro Leu Lys Gln
        355                 360                 365

Val Gln Pro Gln Val Gln Pro Gln Ala His Ser Gln Pro Pro Arg Gln
    370                 375                 380
```

```
Val Gln Leu Gln Leu Gln Lys Gln Val Gln Thr Gln Thr Tyr Pro Gln
385                 390                 395                 400

Val His Thr Gln Ala Gln Pro Ser Val Gln Pro Glu His Pro Pro
            405                 410                 415

Ala Gln Val Ser Val Gln Pro Pro Glu Gln Thr His Gly Gln Pro His
            420                 425                 430

Thr Gln Pro Gln Val Ser Leu Leu Ala Pro Glu Gln Thr Pro Val Val
            435                 440                 445

Val His Val Cys Gly Leu Glu Met Pro Pro Asp Ala Val Glu Ala Gly
450                 455                 460

Gly Gly Met Glu Lys Thr Leu Pro Glu Pro Val Gly Thr Gln Val Ser
465                 470                 475                 480

Met Glu Glu Ile Gln Asn Glu Ser Ala Cys Gly Leu Asp Val Gly Glu
            485                 490                 495

Cys Glu Asn Arg Ala Arg Glu Met Pro Gly Val Trp Gly Ala Gly Gly
            500                 505                 510

Ser Leu Lys Val Thr Ile Leu Gln Ser Ser Asp Ser Arg Ala Phe Ser
            515                 520                 525

Thr Val Pro Leu Thr Pro Val Pro Arg Pro Ser Asp Ser Val Ser Ser
530                 535                 540

Thr Pro Ala Ala Thr Ser Thr Pro Ser Lys Gln Ala Leu Gln Phe Phe
545                 550                 555                 560

Cys Tyr Ile Cys Lys Ala Ser Cys Ser Ser Gln Gln Glu Phe Gln Asp
            565                 570                 575

His Met Ser Glu Pro Gln His Gln Gln Arg Leu Gly Glu Ile Gln His
            580                 585                 590

Met Ser Gln Ala Leu Leu Ser Leu Leu Pro Val Pro Arg Asp Val Leu
            595                 600                 605

Glu Thr Glu Asp Glu Glu Pro Pro Arg Arg Trp Cys Asn Thr Cys
610                 615                 620

Gln Leu Tyr Tyr Met Gly Asp Leu Ile Gln His Arg Arg Thr Gln Asp
625                 630                 635                 640

His Lys Ile Ala Lys Gln Ser Leu Arg Pro Phe Cys Thr Val Cys Asn
            645                 650                 655

Arg Tyr Phe Lys Thr Pro Arg Lys Phe Val Glu His Val Lys Ser Gln
            660                 665                 670

Gly His Lys Asp Lys Ala Lys Glu Leu Lys Ser Leu Glu Lys Glu Ile
            675                 680                 685

Ala Gly Gln Asp Glu Asp His Phe Ile Thr Val Asp Ala Val Gly Cys
            690                 695                 700

Phe Glu Gly Asp Glu Glu Glu Glu Asp Asp Glu Asp Glu Glu Glu
705                 710                 715                 720

Ile Glu Val Glu Glu Glu Leu Cys Lys Gln Val Arg Ser Arg Asp Ile
            725                 730                 735

Ser Arg Glu Glu Trp Lys Gly Ser Glu Thr Tyr Ser Pro Asn Thr Ala
            740                 745                 750

Tyr Gly Val Asp Phe Leu Val Pro Val Met Gly Tyr Ile Cys Arg Ile
            755                 760                 765

Cys His Lys Phe Tyr His Ser Asn Ser Gly Ala Gln Leu Ser His Cys
            770                 775                 780

Lys Ser Leu Gly His Phe Glu Asn Leu Gln Lys Tyr Lys Ala Ala Lys
785                 790                 795                 800
```

-continued

```
Asn Pro Ser Pro Thr Thr Arg Pro Val Ser Arg Arg Cys Ala Ile Asn
                805                 810                 815

Ala Arg Asn Ala Leu Thr Ala Leu Phe Thr Ser Ser Gly Arg Pro Pro
            820                 825                 830

Ser Gln Pro Asn Thr Gln Asp Lys Thr Pro Ser Lys Val Thr Ala Arg
            835                 840                 845

Pro Ser Gln Pro Pro Leu Pro Arg Arg Ser Thr Arg Leu Lys Thr
        850                 855                 860

<210> SEQ ID NO 59
<211> LENGTH: 873
<212> TYPE: PRT
<213> ORGANISM: Homo sapiens

<400> SEQUENCE: 59

Met Phe Ser Gln Gln Gln Gln Leu Gln Gln Gln Gln Gln Gln Gln Leu
1               5                   10                  15

Gln Gln Leu Gln Gln Gln Leu Gln Gln Gln Gln Leu Gln Gln Gln Gln
            20                  25                  30

Gln Leu Leu Gln Leu Gln Gln Leu Leu Gln Gln Ser Pro Pro Gln Ala
        35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Asn
                85                  90                  95

Leu Arg Gly Tyr Gly Met Ala Ser Pro Gly Leu Ala Ala Pro Ser Leu
            100                 105                 110

Thr Pro Pro Gln Leu Ala Thr Pro Asn Leu Gln Gln Phe Phe Pro Gln
        115                 120                 125

Ala Thr Arg Gln Ser Leu Leu Gly Pro Pro Val Gly Val Pro Met
    130                 135                 140

Asn Pro Ser Gln Phe Asn Leu Ser Gly Arg Asn Pro Gln Lys Gln Ala
145                 150                 155                 160

Arg Thr Ser Ser Ser Thr Thr Pro Asn Arg Lys Asp Ser Ser Ser Gln
                165                 170                 175

Thr Met Pro Val Glu Asp Lys Ser Asp Pro Pro Glu Gly Ser Glu Glu
            180                 185                 190

Ala Ala Glu Pro Arg Met Asp Thr Pro Glu Asp Gln Asp Leu Pro Pro
        195                 200                 205

Cys Pro Glu Asp Ile Ala Lys Glu Lys Arg Thr Pro Ala Pro Glu Pro
    210                 215                 220

Glu Pro Cys Glu Ala Ser Glu Leu Pro Ala Lys Arg Leu Arg Ser Ser
225                 230                 235                 240

Glu Glu Pro Thr Glu Lys Glu Pro Pro Gly Gln Leu Gln Val Lys Ala
                245                 250                 255

Gln Pro Gln Ala Arg Met Thr Val Pro Lys Gln Thr Gln Thr Pro Asp
            260                 265                 270

Leu Leu Pro Glu Ala Leu Glu Ala Gln Val Leu Pro Arg Phe Gln Pro
        275                 280                 285

Arg Val Leu Gln Val Gln Ala Gln Val Gln Ser Gln Thr Gln Pro Arg
    290                 295                 300

Ile Pro Ser Thr Asp Thr Gln Val Gln Pro Lys Leu Gln Lys Gln Ala
305                 310                 315                 320
```

-continued

```
Gln Thr Gln Thr Ser Pro Glu His Leu Val Leu Gln Gln Lys Gln Val
            325                 330                 335
Gln Pro Gln Leu Gln Gln Ala Glu Pro Gln Lys Gln Val Gln Pro
        340                 345                 350
Gln Val Gln Pro Gln Ala His Ser Gln Gly Pro Arg Gln Val Gln Leu
            355                 360                 365
Gln Gln Glu Ala Glu Pro Leu Lys Gln Val Gln Pro Gln Val Gln Pro
        370                 375                 380
Gln Ala His Ser Gln Pro Pro Arg Gln Val Gln Leu Gln Leu Gln Lys
385                 390                 395                 400
Gln Val Gln Thr Gln Thr Tyr Pro Gln Val His Thr Gln Ala Gln Pro
            405                 410                 415
Ser Val Gln Pro Gln Glu His Pro Pro Ala Gln Val Ser Val Gln Pro
            420                 425                 430
Pro Glu Gln Thr His Glu Gln Pro His Thr Gln Pro Gln Val Ser Leu
            435                 440                 445
Leu Ala Pro Glu Gln Thr Pro Val Val His Val Cys Gly Leu Glu
        450                 455                 460
Met Pro Pro Asp Ala Val Glu Ala Gly Gly Met Glu Lys Thr Leu
465                 470                 475                 480
Pro Glu Pro Val Gly Thr Gln Val Ser Met Glu Glu Ile Gln Asn Glu
            485                 490                 495
Ser Ala Cys Gly Leu Asp Val Gly Glu Cys Glu Asn Arg Ala Arg Glu
            500                 505                 510
Met Pro Gly Val Trp Gly Ala Gly Gly Ser Leu Lys Val Thr Ile Leu
            515                 520                 525
Gln Ser Ser Asp Ser Arg Ala Phe Ser Thr Val Pro Leu Thr Pro Val
        530                 535                 540
Pro Arg Pro Ser Asp Ser Val Ser Ser Thr Pro Ala Ala Thr Ser Thr
545                 550                 555                 560
Pro Ser Lys Gln Ala Leu Gln Phe Phe Cys Tyr Ile Cys Lys Ala Ser
            565                 570                 575
Cys Ser Ser Gln Gln Glu Phe Gln Asp His Met Ser Glu Pro Gln His
            580                 585                 590
Gln Gln Arg Leu Gly Glu Ile Gln His Met Ser Gln Ala Cys Leu Leu
        595                 600                 605
Ser Leu Leu Pro Val Pro Arg Asp Val Leu Glu Thr Glu Asp Glu Glu
        610                 615                 620
Pro Pro Pro Arg Arg Trp Cys Asn Thr Cys Gln Leu Tyr Tyr Met Gly
625                 630                 635                 640
Asp Leu Ile Gln His Arg Arg Thr Gln Asp His Lys Ile Ala Lys Gln
            645                 650                 655
Ser Leu Arg Pro Phe Cys Thr Val Cys Asn Arg Tyr Phe Lys Thr Pro
            660                 665                 670
Arg Lys Phe Val Glu His Val Lys Ser Gln Gly His Lys Asp Lys Ala
        675                 680                 685
Lys Glu Leu Lys Ser Leu Glu Lys Glu Ile Ala Gly Gln Asp Glu Asp
        690                 695                 700
His Phe Ile Thr Val Asp Ala Val Gly Cys Phe Glu Gly Asp Glu Glu
705                 710                 715                 720
Glu Glu Glu Asp Asp Glu Asp Glu Glu Ile Glu Val Glu Glu Glu
            725                 730                 735
```

```
Leu Cys Lys Gln Val Arg Ser Arg Asp Ile Ser Arg Glu Glu Trp Lys
            740                 745                 750

Gly Ser Glu Thr Tyr Ser Pro Asn Thr Ala Tyr Gly Val Asp Phe Leu
            755                 760                 765

Val Pro Val Met Gly Tyr Ile Cys Arg Ile Cys His Lys Phe Tyr His
    770                 775                 780

Ser Asn Ser Gly Ala Gln Leu Ser His Cys Lys Ser Leu Gly His Phe
785                 790                 795                 800

Glu Asn Leu Gln Lys Tyr Lys Ala Ala Lys Asn Pro Ser Pro Thr Thr
                805                 810                 815

Arg Pro Val Ser Arg Cys Ala Ile Asn Ala Arg Asn Ala Leu Thr
            820                 825                 830

Ala Leu Phe Thr Ser Ser Gly Arg Pro Pro Ser Gln Pro Asn Thr Gln
            835                 840                 845

Asp Lys Thr Pro Ser Lys Val Thr Ala Arg Pro Ser Gln Pro Pro Leu
            850                 855                 860

Pro Arg Arg Ser Thr Arg Leu Lys Thr
865                 870
```

<210> SEQ ID NO 60
<211> LENGTH: 892
<212> TYPE: PRT
<213> ORGANISM: Homo sapiens

<400> SEQUENCE: 60

```
Met Phe Ser Gln Gln Gln Gln Leu Gln Gln Gln Gln Gln Gln Gln Leu
1               5                   10                  15

Gln Gln Leu Gln Gln Gln Gln Leu Gln Gln Gln Leu Gln Gln Gln
            20                  25                  30

Gln Leu Leu Gln Leu Gln Gln Leu Gln Gln Ser Pro Pro Gln Ala
            35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
            115                 120                 125

Pro Gly Leu Ala Ala Pro Ser Leu Thr Pro Pro Gln Leu Ala Thr Pro
    130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Thr Met Pro Val Glu Asp Lys Ser Asp Pro Pro Glu Gly
            195                 200                 205

Ser Glu Glu Ala Ala Glu Pro Arg Met Asp Thr Pro Glu Asp Gln Asp
    210                 215                 220

Leu Pro Pro Cys Pro Glu Asp Ile Ala Lys Glu Lys Arg Thr Pro Ala
225                 230                 235                 240
```

```
Pro Glu Pro Glu Pro Cys Glu Ala Ser Glu Leu Pro Ala Lys Arg Leu
            245                 250                 255
Arg Ser Ser Glu Glu Pro Thr Glu Lys Glu Pro Pro Gly Gln Leu Gln
            260                 265                 270
Val Lys Ala Gln Pro Gln Ala Arg Met Thr Val Pro Lys Gln Thr Gln
            275                 280                 285
Thr Pro Asp Leu Leu Pro Glu Ala Leu Glu Ala Gln Val Leu Pro Arg
            290                 295                 300
Phe Gln Pro Arg Val Leu Gln Val Gln Ala Gln Val Gln Ser Gln Thr
305                 310                 315                 320
Gln Pro Arg Ile Pro Ser Thr Asp Thr Gln Val Gln Pro Lys Leu Gln
            325                 330                 335
Lys Gln Ala Gln Thr Gln Thr Ser Pro Glu His Leu Val Leu Gln Gln
            340                 345                 350
Lys Gln Val Gln Pro Gln Leu Gln Gln Glu Ala Glu Pro Gln Lys Gln
            355                 360                 365
Val Gln Pro Gln Val Gln Pro Gln Ala His Ser Gln Gly Pro Arg Gln
            370                 375                 380
Val Gln Leu Gln Gln Glu Ala Glu Pro Leu Lys Gln Val Gln Pro Gln
385                 390                 395                 400
Val Gln Pro Gln Ala His Ser Gln Pro Arg Gln Val Gln Leu Gln
            405                 410                 415
Leu Gln Lys Gln Val Gln Thr Gln Thr Tyr Pro Gln Val His Thr Gln
            420                 425                 430
Ala Gln Pro Ser Val Gln Pro Gln Glu His Pro Pro Ala Gln Val Ser
            435                 440                 445
Val Gln Pro Pro Glu Gln Thr His Glu Gln Pro His Thr Gln Pro Gln
            450                 455                 460
Val Ser Leu Leu Ala Pro Glu Gln Thr Pro Val Val His Val Cys
465                 470                 475                 480
Gly Leu Glu Met Pro Pro Asp Ala Val Glu Ala Gly Gly Met Glu
            485                 490                 495
Lys Thr Leu Pro Glu Pro Val Gly Thr Gln Val Ser Met Glu Glu Ile
            500                 505                 510
Gln Asn Glu Ser Ala Cys Gly Leu Asp Val Gly Glu Cys Glu Asn Arg
            515                 520                 525
Ala Arg Glu Met Pro Gly Val Trp Gly Ala Gly Gly Ser Leu Lys Val
            530                 535                 540
Thr Ile Leu Gln Ser Ser Asp Ser Arg Ala Phe Ser Thr Val Pro Leu
545                 550                 555                 560
Thr Pro Val Pro Arg Pro Ser Asp Ser Val Ser Ser Thr Pro Ala Ala
            565                 570                 575
Thr Ser Thr Pro Ser Lys Gln Ala Leu Gln Phe Phe Cys Tyr Ile Cys
            580                 585                 590
Lys Ala Ser Cys Ser Ser Gln Gln Glu Phe Gln Asp His Met Ser Glu
            595                 600                 605
Pro Gln His Gln Gln Arg Leu Gly Glu Ile Gln His Met Ser Gln Ala
            610                 615                 620
Cys Leu Leu Ser Leu Leu Pro Val Pro Arg Asp Val Leu Glu Thr Glu
625                 630                 635                 640
Asp Glu Glu Pro Pro Arg Arg Trp Cys Asn Thr Cys Gln Leu Tyr
            645                 650                 655
```

-continued

```
Tyr Met Gly Asp Leu Ile Gln His Arg Arg Thr Gln Asp His Lys Ile
            660                 665                 670

Ala Lys Gln Ser Leu Arg Pro Phe Cys Thr Val Cys Asn Arg Tyr Phe
        675                 680                 685

Lys Thr Pro Arg Lys Phe Val Glu His Val Lys Ser Gln Gly His Lys
    690                 695                 700

Asp Lys Ala Lys Glu Leu Lys Ser Leu Glu Lys Glu Ile Ala Gly Gln
705                 710                 715                 720

Asp Glu Asp His Phe Ile Thr Val Asp Ala Val Gly Cys Phe Glu Gly
                725                 730                 735

Asp Glu Glu Glu Glu Asp Glu Asp Glu Glu Ile Glu Val
            740                 745                 750

Glu Glu Glu Leu Cys Lys Gln Val Arg Ser Arg Asp Ile Ser Arg Glu
        755                 760                 765

Glu Trp Lys Gly Ser Glu Thr Tyr Ser Pro Asn Thr Ala Tyr Gly Val
    770                 775                 780

Asp Phe Leu Val Pro Val Met Gly Tyr Ile Cys Arg Ile Cys His Lys
785                 790                 795                 800

Phe Tyr His Ser Asn Ser Gly Ala Gln Leu Ser His Cys Lys Ser Leu
                805                 810                 815

Gly His Phe Glu Asn Leu Gln Lys Tyr Lys Ala Ala Lys Asn Pro Ser
            820                 825                 830

Pro Thr Thr Arg Pro Val Ser Arg Cys Ala Ile Asn Ala Arg Asn
        835                 840                 845

Ala Leu Thr Ala Leu Phe Thr Ser Ser Gly Arg Pro Pro Ser Gln Pro
    850                 855                 860

Asn Thr Gln Asp Lys Thr Pro Ser Lys Val Thr Ala Arg Pro Ser Gln
865                 870                 875                 880

Pro Pro Leu Pro Arg Arg Ser Thr Arg Leu Lys Thr
                885                 890

<210> SEQ ID NO 61
<211> LENGTH: 868
<212> TYPE: PRT
<213> ORGANISM: Homo sapiens

<400> SEQUENCE: 61

Met Phe Ser Gln Gln Gln Gln Leu Gln Gln Gln Gln Gln Gln Gln Leu
1               5                   10                  15

Gln Gln Leu Gln Gln Gln Gln Leu Gln Gln Gln Leu Gln Gln
            20                  25                  30

Gln Leu Leu Gln Leu Gln Gln Leu Leu Gln Gln Ser Pro Pro Gln Ala
        35                  40                  45

Pro Leu Pro Met Ala Val Ser Arg Gly Leu Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
        115                 120                 125

Pro Gly Leu Ala Ala Pro Ser Leu Thr Pro Pro Gln Leu Ala Thr Pro
    130                 135                 140
```

-continued

```
Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Gln Thr Met Pro Val Glu Asp Lys Ser
        195                 200                 205

Asp Pro Pro Glu Gly Ser Glu Glu Ala Ala Glu Pro Arg Met Asp Thr
210                 215                 220

Pro Glu Asp Gln Asp Leu Pro Pro Cys Pro Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
                260                 265                 270

Pro Gly Gln Leu Gln Val Lys Ala Gln Pro Gln Ala Arg Met Thr Val
            275                 280                 285

Pro Lys Gln Thr Gln Thr Pro Asp Leu Leu Pro Glu Ala Leu Glu Ala
290                 295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
                325                 330                 335

Gln Pro Lys Leu Gln Lys Gln Ala Gln Thr Gln Thr Ser Pro Glu His
            340                 345                 350

Leu Val Leu Gln Gln Lys Gln Val Gln Pro Gln Leu Gln Gln Glu Ala
            355                 360                 365

Glu Pro Gln Lys Gln Val Gln Pro Val Gln Pro Gln Ala His Ser
370                 375                 380

Gln Gly Pro Arg Gln Val Gln Leu Gln Gln Glu Ala Glu Pro Leu Lys
385                 390                 395                 400

Gln Val Gln Gln Val His Thr Gln Ala Gln Pro Ser Val Gln Pro Gln
                405                 410                 415

Glu His Pro Pro Ala Gln Val Ser Val Gln Pro Pro Glu Gln Thr His
            420                 425                 430

Glu Gln Pro His Thr Gln Pro Gln Val Ser Leu Leu Ala Pro Glu Gln
        435                 440                 445

Thr Pro Val Val Val His Val Cys Gly Leu Glu Met Pro Pro Asp Ala
450                 455                 460

Val Glu Ala Gly Gly Gly Met Glu Lys Thr Leu Pro Glu Pro Val Gly
465                 470                 475                 480

Thr Gln Val Ser Met Glu Glu Ile Gln Asn Glu Ser Ala Cys Gly Leu
            485                 490                 495

Asp Val Gly Glu Cys Glu Asn Arg Ala Arg Glu Met Pro Gly Val Trp
            500                 505                 510

Gly Ala Gly Gly Ser Leu Lys Val Thr Ile Leu Gln Ser Ser Asp Ser
            515                 520                 525

Arg Ala Phe Ser Thr Val Pro Leu Thr Pro Val Pro Arg Pro Ser Asp
        530                 535                 540

Ser Val Ser Ser Thr Pro Ala Ala Thr Ser Thr Pro Ser Lys Gln Ala
545                 550                 555                 560
```

-continued

```
Leu Gln Phe Phe Cys Tyr Ile Cys Lys Ala Ser Cys Ser Ser Gln Gln
                565                 570                 575

Glu Phe Gln Asp His Met Ser Glu Pro Gln His Gln Arg Leu Gly
            580                 585                 590

Glu Ile Gln His Met Ser Gln Ala Cys Leu Leu Ser Leu Leu Pro Val
            595                 600                 605

Pro Arg Asp Val Leu Glu Thr Glu Asp Glu Pro Pro Arg Arg
610                 615                 620

Trp Cys Asn Thr Cys Gln Leu Tyr Tyr Met Gly Asp Leu Ile Gln His
625                 630                 635                 640

Arg Arg Thr Gln Asp His Lys Ile Ala Lys Gln Ser Leu Arg Pro Phe
                645                 650                 655

Cys Thr Val Cys Asn Arg Tyr Phe Lys Thr Pro Arg Lys Phe Val Glu
                660                 665                 670

His Val Lys Ser Gln Gly His Lys Asp Lys Ala Lys Glu Leu Lys Ser
            675                 680                 685

Leu Glu Lys Glu Ile Ala Gly Gln Asp Glu Asp His Phe Ile Thr Val
            690                 695                 700

Asp Ala Val Gly Cys Phe Glu Gly Asp Glu Glu Glu Glu Asp Asp
705                 710                 715                 720

Glu Asp Glu Glu Glu Ile Glu Val Glu Glu Leu Cys Lys Gln Val
                725                 730                 735

Arg Ser Arg Asp Ile Ser Arg Glu Glu Trp Lys Gly Ser Glu Thr Tyr
                740                 745                 750

Ser Pro Asn Thr Ala Tyr Gly Val Asp Phe Leu Val Pro Val Met Gly
                755                 760                 765

Tyr Ile Cys Arg Ile Cys His Lys Phe Tyr His Ser Asn Ser Gly Ala
770                 775                 780

Gln Leu Ser His Cys Lys Ser Leu Gly His Phe Glu Asn Leu Gln Lys
785                 790                 795                 800

Tyr Lys Ala Ala Lys Asn Pro Ser Pro Thr Thr Arg Pro Val Ser Arg
                805                 810                 815

Arg Cys Ala Ile Asn Ala Arg Asn Ala Leu Thr Ala Leu Phe Thr Ser
                820                 825                 830

Ser Gly Arg Pro Pro Ser Gln Pro Asn Thr Gln Asp Lys Thr Pro Ser
            835                 840                 845

Lys Val Thr Ala Arg Pro Ser Gln Pro Pro Leu Pro Arg Arg Ser Thr
            850                 855                 860

Arg Leu Lys Thr
865

<210> SEQ ID NO 62
<211> LENGTH: 841
<212> TYPE: PRT
<213> ORGANISM: Homo sapiens

<400> SEQUENCE: 62

Met Phe Ser Gln Gln Gln Gln Leu Gln Gln Gln Gln Gln Gln Gln Leu
1               5                   10                  15

Gln Gln Leu Gln Gln Gln Leu Gln Gln Gln Leu Gln Gln Gln
            20                  25                  30

Gln Leu Leu Gln Leu Gln Leu Leu Gln Gln Ser Pro Pro Gln Ala
            35                  40                  45

Pro Leu Pro Met Ala Val Ser Arg Gly Leu Pro Pro Gln Gln Pro Gln
50                  55                  60
```

-continued

```
Gln Pro Leu Leu Asn Leu Gln Gly Thr Asn Ser Ala Ser Leu Leu Asn
 65                  70                  75                  80

Gly Ser Met Leu Gln Arg Ala Leu Leu Leu Gln Gln Leu Gln Gly Leu
             85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
            115                 120                 125

Pro Gly Leu Ala Ala Pro Ser Leu Thr Pro Gln Leu Ala Thr Pro
            130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
                180                 185                 190

Asn Arg Lys Asp Ser Ser Gln Thr Met Pro Val Glu Asp Lys Ser
            195                 200                 205

Asp Pro Pro Glu Gly Ser Glu Glu Ala Ala Glu Pro Arg Met Asp Thr
210                 215                 220

Pro Glu Asp Gln Asp Leu Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Pro Thr Glu Lys Glu Pro
                260                 265                 270

Pro Gly Gln Leu Gln Val Lys Ala Gln Pro Gln Ala Arg Met Thr Val
            275                 280                 285

Pro Lys Gln Thr Gln Thr Pro Asp Leu Leu Pro Glu Ala Leu Glu Ala
            290                 295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
                325                 330                 335

Gln Pro Lys Leu Gln Lys Gln Ala Gln Thr Gln Thr Ser Pro Glu His
                340                 345                 350

Leu Val Leu Gln Gln Lys Gln Val Gln Pro Gln Leu Gln Gln Glu Ala
            355                 360                 365

Glu Pro Gln Lys Gln Val Gln Pro Gln Val His Thr Gln Ala Gln Pro
            370                 375                 380

Ser Val Gln Pro Gln Glu His Pro Pro Ala Gln Val Ser Val Gln Pro
385                 390                 395                 400

Pro Glu Gln Thr His Glu Gln Pro His Thr Gln Pro Gln Val Ser Leu
                405                 410                 415

Leu Ala Pro Glu Gln Thr Val Val Val His Val Cys Gly Leu Glu
                420                 425                 430

Met Pro Pro Asp Ala Val Glu Ala Gly Gly Gly Met Glu Lys Thr Leu
            435                 440                 445

Pro Glu Pro Val Gly Thr Gln Val Ser Met Glu Glu Ile Gln Asn Glu
            450                 455                 460

Ser Ala Cys Gly Leu Asp Val Gly Glu Cys Glu Asn Arg Ala Arg Glu
465                 470                 475                 480
```

```
Met Pro Gly Val Trp Gly Ala Gly Gly Ser Leu Lys Val Thr Ile Leu
            485                 490                 495

Gln Ser Ser Asp Ser Arg Ala Phe Ser Thr Val Pro Leu Thr Pro Val
        500                 505                 510

Pro Arg Pro Ser Asp Ser Val Ser Ser Thr Pro Ala Ala Thr Ser Thr
        515                 520                 525

Pro Ser Lys Gln Ala Leu Gln Phe Phe Cys Tyr Ile Cys Lys Ala Ser
        530                 535                 540

Cys Ser Ser Gln Gln Glu Phe Gln Asp His Met Ser Glu Pro Gln His
545                 550                 555                 560

Gln Gln Arg Leu Gly Glu Ile Gln His Met Ser Gln Ala Cys Leu Leu
                565                 570                 575

Ser Leu Leu Pro Val Pro Arg Asp Val Leu Glu Thr Glu Asp Glu Glu
                580                 585                 590

Pro Pro Pro Arg Arg Trp Cys Asn Thr Cys Gln Leu Tyr Tyr Met Gly
            595                 600                 605

Asp Leu Ile Gln His Arg Arg Thr Gln Asp His Lys Ile Ala Lys Gln
            610                 615                 620

Ser Leu Arg Pro Phe Cys Thr Val Cys Asn Arg Tyr Phe Lys Thr Pro
625                 630                 635                 640

Arg Lys Phe Val Glu His Val Lys Ser Gln Gly His Lys Asp Lys Ala
                645                 650                 655

Lys Glu Leu Lys Ser Leu Glu Lys Glu Ile Ala Gly Gln Asp Glu Asp
                660                 665                 670

His Phe Ile Thr Val Asp Ala Val Gly Cys Phe Glu Gly Asp Glu Glu
            675                 680                 685

Glu Glu Glu Asp Asp Glu Asp Glu Glu Ile Glu Val Glu Glu Glu
            690                 695                 700

Leu Cys Lys Gln Val Arg Ser Arg Asp Ile Ser Arg Glu Glu Trp Lys
705                 710                 715                 720

Gly Ser Glu Thr Tyr Ser Pro Asn Thr Ala Tyr Gly Val Asp Phe Leu
                725                 730                 735

Val Pro Val Met Gly Tyr Ile Cys Arg Ile Cys His Lys Phe Tyr His
                740                 745                 750

Ser Asn Ser Gly Ala Gln Leu Ser His Cys Lys Ser Leu Gly His Phe
            755                 760                 765

Glu Asn Leu Gln Lys Tyr Lys Ala Ala Lys Asn Pro Ser Thr Thr
            770                 775                 780

Arg Pro Val Ser Arg Cys Ala Ile Asn Ala Arg Asn Ala Leu Thr
785                 790                 795                 800

Ala Leu Phe Thr Ser Ser Gly Arg Pro Pro Ser Gln Pro Asn Thr Gln
                805                 810                 815

Asp Lys Thr Pro Ser Lys Val Thr Ala Arg Pro Ser Gln Pro Pro Leu
            820                 825                 830

Pro Arg Arg Ser Thr Arg Leu Lys Thr
            835                 840

<210> SEQ ID NO 63
<211> LENGTH: 785
<212> TYPE: PRT
<213> ORGANISM: Homo sapiens

<400> SEQUENCE: 63

Met Phe Ser Gln Gln Gln Gln Leu Gln Gln Gln Gln Gln Leu
1               5                   10                  15
```

```
Gln Gln Leu Gln Gln Gln Gln Leu Gln Gln Gln Leu Gln Gln
            20                  25                  30

Gln Leu Leu Gln Leu Gln Gln Leu Leu Gln Ser Pro Pro Gln Ala
        35                  40                  45

Pro Leu Pro Met Ala Val Ser Arg Gly Leu Pro Pro Gln Pro Gln
 50                  55                  60

Gln Pro Leu Leu Asn Leu Gln Gly Thr Asn Ser Ala Ser Leu Leu Asn
 65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
        115                 120                 125

Pro Gly Leu Ala Ala Pro Ser Leu Thr Pro Gln Leu Ala Thr Pro
 130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Gln Thr Met Pro Val Glu Asp Lys Ser
        195                 200                 205

Asp Pro Pro Glu Gly Ser Glu Glu Ala Ala Glu Pro Arg Met Asp Thr
 210                 215                 220

Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
            260                 265                 270

Pro Gly Gln Leu Gln Val Lys Ala Gln Pro Gln Ala Arg Met Thr Val
        275                 280                 285

Pro Lys Gln Thr Gln Thr Pro Asp Leu Leu Pro Glu Ala Leu Glu Ala
 290                 295                 300

Gln Val Leu Pro Arg Phe Gln Pro Arg Val Leu Gln Val Gln Ala Pro
305                 310                 315                 320

Gln Val His Thr Gln Ala Gln Pro Ser Val Gln Pro Gln Glu His Pro
                325                 330                 335

Pro Ala Gln Val Ser Val Gln Pro Glu Gln Thr His Glu Gln Pro
            340                 345                 350

His Thr Gln Pro Gln Val Ser Leu Leu Ala Pro Glu Gln Thr Pro Val
        355                 360                 365

Val Val His Val Cys Gly Leu Glu Met Pro Pro Asp Ala Val Glu Ala
 370                 375                 380

Gly Gly Gly Met Glu Lys Thr Leu Pro Glu Pro Val Gly Thr Gln Val
385                 390                 395                 400

Ser Met Glu Glu Ile Gln Asn Glu Ser Ala Cys Gly Leu Asp Val Gly
                405                 410                 415

Glu Cys Glu Asn Arg Ala Arg Glu Met Pro Gly Val Trp Gly Ala Gly
            420                 425                 430
```

Gly Ser Leu Lys Val Thr Ile Leu Gln Ser Ser Asp Ser Arg Ala Phe
        435                 440                 445

Ser Thr Val Pro Leu Thr Pro Val Pro Arg Pro Ser Asp Ser Val Ser
450                 455                 460

Ser Thr Pro Ala Ala Thr Ser Thr Pro Ser Lys Gln Ala Leu Gln Phe
465                 470                 475                 480

Phe Cys Tyr Ile Cys Lys Ala Ser Cys Ser Ser Gln Gln Glu Phe Gln
                485                 490                 495

Asp His Met Ser Glu Pro Gln His Gln Arg Leu Gly Glu Ile Gln
            500                 505                 510

His Met Ser Gln Ala Cys Leu Leu Ser Leu Leu Pro Val Pro Arg Asp
        515                 520                 525

Val Leu Glu Thr Glu Asp Glu Pro Pro Arg Arg Trp Cys Asn
530                 535                 540

Thr Cys Gln Leu Tyr Tyr Met Gly Asp Leu Ile Gln His Arg Arg Thr
545                 550                 555                 560

Gln Asp His Lys Ile Ala Lys Gln Ser Leu Arg Pro Phe Cys Thr Val
                565                 570                 575

Cys Asn Arg Tyr Phe Lys Thr Pro Arg Lys Phe Val Glu His Val Lys
            580                 585                 590

Ser Gln Gly His His Lys Asp Lys Ala Lys Glu Leu Lys Ser Leu Glu Lys
        595                 600                 605

Glu Ile Ala Gly Gln Asp Glu Asp His Phe Ile Thr Val Asp Ala Val
        610                 615                 620

Gly Cys Phe Glu Gly Asp Glu Glu Glu Asp Asp Glu Asp Glu
625                 630                 635                 640

Glu Glu Ile Glu Val Glu Glu Leu Cys Lys Gln Val Arg Ser Arg
                645                 650                 655

Asp Ile Ser Arg Glu Glu Trp Lys Gly Ser Glu Thr Tyr Ser Pro Asn
            660                 665                 670

Thr Ala Tyr Gly Val Asp Phe Leu Val Pro Val Met Gly Tyr Ile Cys
        675                 680                 685

Arg Ile Cys His Lys Phe Tyr His Ser Asn Ser Gly Ala Gln Leu Ser
690                 695                 700

His Cys Lys Ser Leu Gly His Phe Glu Asn Leu Gln Lys Tyr Lys Ala
705                 710                 715                 720

Ala Lys Asn Pro Ser Pro Thr Thr Arg Pro Val Ser Arg Arg Cys Ala
                725                 730                 735

Ile Asn Ala Arg Asn Ala Leu Thr Ala Leu Phe Thr Ser Ser Gly Arg
            740                 745                 750

Pro Pro Ser Gln Pro Asn Thr Gln Asp Lys Thr Pro Ser Lys Val Thr
        755                 760                 765

Ala Arg Pro Ser Gln Pro Pro Leu Pro Arg Arg Ser Thr Arg Leu Lys
    770                 775                 780

Thr
785

<210> SEQ ID NO 64
<211> LENGTH: 889
<212> TYPE: PRT
<213> ORGANISM: Homo sapiens

<400> SEQUENCE: 64

Met Phe Ser Gln Gln Gln Gln Leu Gln Gln Gln Gln Gln Leu
1               5                   10                  15

```
Gln Gln Leu Gln Gln Gln Gln Leu Gln Gln Gln Leu Gln Gln
        20                  25                  30

Gln Leu Leu Gln Leu Gln Gln Leu Gln Gln Ser Pro Gln Ala
            35                  40                  45

Pro Leu Pro Met Ala Val Ser Arg Gly Leu Pro Pro Gln Pro Gln
 50                      55                  60

Gln Pro Leu Leu Asn Leu Gln Gly Thr Asn Ser Ala Ser Leu Leu Asn
 65                  70                  75                  80

Gly Ser Met Leu Gln Arg Ala Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
                115                 120                 125

Pro Gly Leu Ala Ala Pro Ser Leu Thr Pro Pro Gln Leu Ala Thr Pro
 130                     135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Gln Thr Met Pro Val Glu Asp Lys Ser
            195                 200                 205

Asp Pro Pro Glu Gly Ser Glu Glu Ala Ala Glu Pro Arg Met Asp Thr
 210                     215                 220

Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
                260                 265                 270

Pro Gly Gln Leu Gln Val Lys Ala Gln Pro Gln Ala Arg Met Thr Val
            275                 280                 285

Pro Lys Gln Thr Gln Thr Pro Asp Leu Leu Pro Glu Ala Leu Glu Ala
 290                     295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
                325                 330                 335

Gln Pro Lys Leu Gln Lys Gln Ala Gln Thr Gln Thr Ser Pro Glu His
            340                 345                 350

Leu Val Leu Gln Gln Lys Gln Val Gln Pro Gln Leu Gln Gln Glu Ala
            355                 360                 365

Glu Pro Gln Lys Gln Val Gln Pro Gln Val Gln Pro Gln Ala His Ser
 370                     375                 380

Gln Gly Pro Arg Gln Val Gln Leu Gln Gln Glu Ala Glu Pro Leu Lys
385                 390                 395                 400

Gln Val Gln Pro Gln Val Gln Pro Gln Ala His Ser Gln Pro Pro Arg
                405                 410                 415

Gln Val Gln Leu Gln Leu Gln Lys Gln Val Gln Thr Gln Thr Tyr Pro
            420                 425                 430
```

```
Gln Val His Thr Gln Ala Gln Pro Ser Val Gln Pro Glu His Pro
            435                 440                 445
Pro Ala Gln Val Ser Val Gln Pro Pro Glu Gln Thr His Glu Gln Pro
    450                 455                 460
His Thr Gln Pro Gln Val Ser Leu Leu Ala Pro Glu Gln Thr Pro Val
465                 470                 475                 480
Val Val His Val Cys Gly Leu Glu Met Pro Pro Asp Ala Val Glu Ala
                485                 490                 495
Gly Gly Gly Met Glu Lys Thr Leu Pro Glu Pro Val Gly Thr Gln Val
            500                 505                 510
Ser Met Glu Glu Ile Gln Asn Glu Ser Ala Cys Gly Leu Asp Val Gly
        515                 520                 525
Glu Cys Glu Asn Arg Ala Arg Glu Met Pro Gly Val Trp Gly Ala Gly
    530                 535                 540
Gly Ser Leu Lys Val Thr Ile Leu Gln Ser Ser Asp Ser Arg Ala Phe
545                 550                 555                 560
Ser Thr Val Pro Leu Thr Pro Val Pro Arg Pro Ser Asp Ser Val Ser
                565                 570                 575
Ser Thr Pro Ala Ala Thr Ser Thr Pro Ser Lys Gln Ala Leu Gln Phe
            580                 585                 590
Phe Cys Tyr Ile Cys Lys Ala Ser Cys Ser Ser Gln Gln Glu Phe Gln
        595                 600                 605
Asp His Met Ser Glu Pro Gln His Gln Arg Leu Gly Glu Ile Gln
    610                 615                 620
His Met Ser Gln Ala Cys Leu Leu Ser Leu Leu Pro Val Pro Arg Asp
625                 630                 635                 640
Val Leu Glu Thr Glu Asp Glu Pro Pro Arg Arg Trp Cys Asn
                645                 650                 655
Thr Cys Gln Leu Tyr Tyr Met Gly Asp Leu Ile Gln His Arg Arg Thr
            660                 665                 670
Gln Asp His Lys Ile Ala Lys Gln Ser Leu Arg Pro Phe Cys Thr Val
        675                 680                 685
Cys Asn Arg Tyr Phe Lys Thr Pro Arg Lys Phe Val Glu His Val Lys
    690                 695                 700
Ser Gln Gly His Lys Asp Lys Ala Lys Glu Leu Lys Ser Leu Glu Lys
705                 710                 715                 720
Glu Ile Ala Gly Gln Asp Glu Asp His Phe Ile Thr Val Asp Ala Val
                725                 730                 735
Gly Cys Phe Glu Gly Asp Glu Glu Glu Asp Asp Glu Asp Glu
            740                 745                 750
Glu Glu Ile Glu Val Arg Ser Arg Asp Ile Ser Arg Glu Glu Trp Lys
        755                 760                 765
Gly Ser Glu Thr Tyr Ser Pro Asn Thr Ala Tyr Gly Val Asp Phe Leu
    770                 775                 780
Val Pro Val Met Gly Tyr Ile Cys Arg Ile Cys His Lys Phe Tyr His
785                 790                 795                 800
Ser Asn Ser Gly Ala Gln Leu Ser His Cys Lys Ser Leu Gly His Phe
                805                 810                 815
Glu Asn Leu Gln Lys Tyr Lys Ala Ala Lys Asn Pro Ser Pro Thr Thr
            820                 825                 830
Arg Pro Val Ser Arg Arg Cys Ala Ile Asn Ala Arg Asn Ala Leu Thr
        835                 840                 845
Ala Leu Phe Thr Ser Ser Gly Arg Pro Pro Ser Gln Pro Asn Thr Gln
```

```
                         850                 855                 860
Asp Lys Thr Pro Ser Lys Val Thr Ala Arg Pro Ser Gln Pro Pro Leu
865                 870                 875                 880

Pro Arg Arg Ser Thr Arg Leu Lys Thr
                885

<210> SEQ ID NO 65
<211> LENGTH: 873
<212> TYPE: PRT
<213> ORGANISM: Homo sapiens

<400> SEQUENCE: 65

Met Phe Ser Gln Gln Gln Gln Leu Gln Gln Gln Gln Gln Gln Gln Leu
1               5                   10                  15

Gln Gln Leu Gln Gln Gln Gln Leu Gln Gln Gln Leu Gln Gln Gln Gln
            20                  25                  30

Gln Leu Leu Gln Leu Gln Gln Leu Leu Gln Gln Ser Pro Pro Gln Ala
        35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Asn
                85                  90                  95

Leu Arg Gly Tyr Gly Met Ala Ser Pro Gly Leu Ala Ala Pro Ser Leu
            100                 105                 110

Thr Pro Pro Gln Leu Ala Thr Pro Asn Leu Gln Gln Phe Phe Pro Gln
        115                 120                 125

Ala Thr Arg Gln Ser Leu Leu Gly Pro Pro Val Gly Val Pro Met
    130                 135                 140

Asn Pro Ser Gln Phe Asn Leu Ser Gly Arg Asn Pro Gln Lys Gln Ala
145                 150                 155                 160

Arg Thr Ser Ser Ser Thr Thr Pro Asn Arg Lys Asp Ser Ser Ser Gln
                165                 170                 175

Thr Met Pro Val Glu Asp Lys Ser Asp Pro Pro Glu Gly Ser Glu Glu
            180                 185                 190

Ala Ala Glu Pro Arg Met Asp Thr Pro Glu Asp Gln Asp Leu Pro Pro
        195                 200                 205

Cys Pro Glu Asp Ile Ala Lys Glu Lys Arg Thr Pro Ala Pro Glu Pro
    210                 215                 220

Glu Pro Cys Glu Ala Ser Glu Leu Pro Ala Lys Arg Leu Arg Ser Ser
225                 230                 235                 240

Glu Glu Pro Thr Glu Lys Glu Pro Pro Gly Gln Leu Gln Val Lys Ala
                245                 250                 255

Gln Pro Gln Ala Arg Met Thr Val Pro Lys Gln Thr Gln Thr Pro Asp
            260                 265                 270

Leu Leu Pro Glu Ala Leu Glu Ala Gln Val Leu Pro Arg Phe Gln Pro
        275                 280                 285

Arg Val Leu Gln Val Gln Ala Gln Val Gln Ser Gln Thr Gln Pro Arg
    290                 295                 300

Ile Pro Ser Thr Asp Thr Gln Val Gln Pro Lys Leu Gln Lys Gln Ala
305                 310                 315                 320

Gln Thr Gln Thr Ser Pro Glu His Leu Val Leu Gln Gln Lys Gln Val
                325                 330                 335
```

-continued

```
Gln Pro Gln Leu Gln Gln Glu Ala Glu Pro Gln Lys Gln Val Gln Pro
                340                 345                 350
Gln Val Gln Pro Gln Ala His Ser Gln Gly Pro Arg Gln Val Gln Leu
            355                 360                 365
Gln Gln Glu Ala Glu Pro Leu Lys Gln Val Gln Pro Gln Val Gln Pro
        370                 375                 380
Gln Ala His Ser Gln Pro Pro Arg Gln Val Gln Leu Gln Leu Gln Lys
385                 390                 395                 400
Gln Val Gln Thr Gln Thr Tyr Pro Gln Val His Thr Gln Ala Gln Pro
                405                 410                 415
Ser Val Gln Pro Gln Glu His Pro Pro Ala Gln Val Ser Val Gln Pro
            420                 425                 430
Pro Glu Gln Thr His Glu Gln Pro His Thr Gln Pro Gln Val Ser Leu
        435                 440                 445
Leu Ala Pro Glu Gln Thr Pro Val Val His Val Cys Gly Leu Glu
450                 455                 460
Met Pro Pro Asp Ala Val Glu Ala Gly Gly Met Glu Lys Thr Leu
465                 470                 475                 480
Pro Glu Pro Val Gly Thr Gln Val Ser Met Glu Glu Ile Gln Asn Glu
                485                 490                 495
Ser Ala Cys Gly Leu Asp Val Gly Glu Cys Glu Asn Arg Ala Arg Glu
            500                 505                 510
Met Pro Gly Val Trp Gly Ala Gly Ser Leu Lys Val Thr Ile Leu
        515                 520                 525
Gln Ser Ser Asp Ser Arg Ala Phe Ser Thr Val Pro Leu Thr Pro Val
530                 535                 540
Pro Arg Pro Ser Asp Ser Val Ser Ser Thr Pro Ala Ala Thr Ser Thr
545                 550                 555                 560
Pro Ser Lys Gln Ala Leu Gln Phe Phe Cys Tyr Ile Cys Lys Ala Ser
                565                 570                 575
Cys Ser Ser Gln Gln Glu Phe Gln Asp His Met Ser Glu Pro Gln His
            580                 585                 590
Gln Gln Arg Leu Gly Glu Ile Gln His Met Ser Gln Ala Cys Leu Leu
        595                 600                 605
Ser Leu Leu Pro Val Pro Arg Asp Val Leu Glu Thr Glu Asp Glu Glu
610                 615                 620
Pro Pro Pro Arg Arg Trp Cys Asn Thr Cys Gln Leu Tyr Tyr Met Gly
625                 630                 635                 640
Asp Leu Ile Gln His Arg Arg Thr Gln Asp His Lys Ile Ala Lys Gln
                645                 650                 655
Ser Leu Arg Pro Phe Cys Thr Val Cys Asn Arg Tyr Phe Lys Thr Pro
            660                 665                 670
Arg Lys Phe Val Glu His Val Lys Ser Gln Gly His Lys Asp Lys Ala
        675                 680                 685
Lys Glu Leu Lys Ser Leu Glu Lys Glu Ile Ala Gly Gln Asp Glu Asp
690                 695                 700
His Phe Ile Thr Val Asp Ala Val Gly Cys Phe Glu Gly Asp Glu Glu
705                 710                 715                 720
Glu Glu Glu Asp Asp Glu Asp Glu Glu Ile Glu Val Glu Glu Glu
                725                 730                 735
Leu Cys Lys Gln Val Arg Ser Arg Asp Ile Ser Arg Glu Glu Trp Lys
            740                 745                 750
Gly Ser Glu Thr Tyr Ser Pro Asn Thr Ala Tyr Gly Val Asp Phe Leu
```

```
                755                 760                 765
Val Pro Val Met Gly Tyr Ile Cys Arg Ile Cys His Lys Phe Tyr His
    770                 775                 780

Ser Asn Ser Gly Ala Gln Leu Ser His Cys Lys Ser Leu Gly His Phe
785                 790                 795                 800

Glu Asn Leu Gln Lys Tyr Lys Ala Ala Lys Asn Pro Ser Pro Thr Thr
                805                 810                 815

Arg Pro Val Ser Arg Arg Cys Ala Ile Asn Ala Arg Asn Ala Leu Thr
            820                 825                 830

Ala Leu Phe Thr Ser Ser Gly Arg Pro Pro Ser Gln Pro Asn Thr Gln
        835                 840                 845

Asp Lys Thr Pro Ser Lys Val Thr Ala Arg Pro Ser Gln Pro Pro Leu
    850                 855                 860

Pro Arg Arg Ser Thr Arg Leu Lys Thr
865                 870

<210> SEQ ID NO 66
<211> LENGTH: 2821
<212> TYPE: DNA
<213> ORGANISM: Homo sapiens

<400> SEQUENCE: 66
tgggggctgc gggccggcc  catccgtggg ggcgacttga gcgttgaggg cgcgcgggga    60
ggcgagccac catgttcagc cagcagcagc agcagctcca gcaacagcag ggccccgttg   120
cccatggctg tcagccgggg gctcccccg  cagcagccac agcagccgct tctgaatctc   180
cagggcacca actcagcctc cctcctcaac ggctccatgc tgcagagagc tttgctttta   240
cagcagttgc aaggactgga ccagtttgca atgccaccag ccacgtatga cactgccggt   300
ctcaccatgc ccacagcaac actgggtaac ctccgaggct atggcatggc atccccaggc   360
ctcgcagccc ccagcctcac accccacaa  ctggccactc caaatttgca acagttcttt   420
ccccaggcca ctcgccagtc cttgctggga cctcctcctg ttggggtccc catgaaccct   480
tcccagttca ccttcagg   acggaacccc cagaaacagg cccggacctc ctcctctacc   540
acccccaatc gaaaggattc ttcttctcag acaatgcctg tggaagacaa gtcagacccc   600 ccagagggt  ctgaggaagc cgcagagccc cggatggaca caccagaaga ccaagattta   660
ccgccctgcc cagaggacat cgccaaggaa aaacgcactc cagcacctga gcctgagcct   720
tgtgaggcgt ccgagctgcc agcaaagaga ttgaggagct cagaagagcc cacagagaag   780
gaacctccag ggcagttaca ggtgaaggcc cagccgcagg cccggatgac agtaccgaaa   840
cagacacaga caccagacct gctgcctgag gccctggaag cccaagtgct gccacgattc   900
cagccacggg tcctgcaggt ccaggcccag gtgcagtcac agactcagcc gcggatacca   960
tccacagaca cccaggtgca gccaaagctg cagaagcagg cgcaaacaca gacctctcca  1020
gagcacttag tgctgcaaca gaagcaggtg cagccacagc tgcagcagga ggcagagcca  1080
cagaagcagg tgcagccaca ggtacagcca caggcacatt cacagggccc aaggcaggtg  1140
cagctgcagc aggaggcaga gccgctgaag caggtgcagc acaggtgca  gccccaggca  1200 cattcacagc cccaaggca  ggtgcagctg cagctgcaga agcaggtcca gacacagaca  1260
tatccacagg tccacacaca ggcacagcca agcgtccagc acaggagca  tcctccagcg  1320 caggtgtcag tacagccacc agagcagacc catgagcagc tcacacccca gccgcaggtg  1380
tcgttgctgg ctccagagca aacaccagtt gtggttcatg tctgcgggct ggagatgcca  1440
```

| | |
|---|---:|
| cctgatgcag tagaagctgg tggaggcatg gaaaagacct tgccagagcc tgtgggcacc | 1500 |
| caagtcagca tggaagagat tcagaatgag tcggcctgtg ccctagatgt gggagaatgt | 1560 |
| gaaaacagag cgagagagat gccaggggta tggggcgccg ggggctccct gaaggtcacc | 1620 |
| attctgcaga gcagtgacag ccgggccttt agcactgtac ccctgacacc tgtccccgc | 1680 |
| cccagtgact ccgtctcctc caccctgcg gctaccagca ctccctctaa gcaggccctc | 1740 |
| cagttcttct gctacatctg caaggccagc tgctccagcc agcaggagtt ccaggaccac | 1800 |
| atgtcggagc tcagcaccca gcagcggcta ggggagatcc agcacatgag ccaagcctgc | 1860 |
| ctcctgtccc tgctgcccgt gccccgggac gtcctggaga cagaggatga ggagcctcca | 1920 |
| ccaaggcgct ggtgcaacac ctgccagctc tactacatgg gggacctgat ccaacaccgc | 1980 |
| aggacacagg accacaagat tgccaaacaa tccttgcgac ccttctgcac cgtttgcaac | 2040 |
| cgctacttca aaacccctcg caagtttgtg gagcacgtga agtcccaggg gcataaggac | 2100 |
| aaagccaagg agctgaagtc gcttgagaaa gaaattgctg ccaagatga ggaccacttc | 2160 |
| attacagtgg acgctgtggg ttgcttcgag ggtgatgaag aagaggaaga ggatgatgag | 2220 |
| gatgaagaag agatcgaggt tgaggaggaa ctctgcaagc aggtgaggtc cagagatata | 2280 |
| tccagagagg agtggaaggg ctcggagacc tacagcccca atactgcata tggtgtggac | 2340 |
| ttcctggtgc ccgtgatggg ctatatctgc cgcatctgcc acaagttcta tcacagcaac | 2400 |
| tcaggggcac agctctccca ctgcaagtcc ctgggccact ttgagaacct gcagaaatac | 2460 |
| aaggcggcca gaaccccag ccccaccacc cgacctgtga ccgccggtg cgcaatcaac | 2520 |
| gcccggaacg ctttgacagc cctgttcacc tccagcggcc gcccaccctc ccagcccaac | 2580 |
| acccaggaca aaacacccag caaggtgacg gctcgaccct cccagccccc actacctcgg | 2640 |
| cgctcaaccc gcctcaaaac ctgatagagg gacctccctg tccctggcct gcctgggtcc | 2700 |
| agatctgcta atgcttttta ggagtctgcc tggaaacttt gacatggttc atgtttttac | 2760 |
| tcaaaatcca ataaacaag gtagtttggc tgtgcaaaaa aaaaaaaaa aaaaaaaaa | 2820 |
| a | 2821 |

<210> SEQ ID NO 67
<211> LENGTH: 2850
<212> TYPE: DNA
<213> ORGANISM: Homo sapiens

<400> SEQUENCE: 67

| | |
|---|---:|
| tgggggctgc ggggccggcc catccgtggg ggcgacttga gcgttgaggg cgcgcgggga | 60 |
| ggcgagccac catgttcagc cagcagcagc agcagctcca gcaacagcag cagcagctcc | 120 |
| agcagttaca gcagcagcag ctccagcagc agcaattgca gcagcagcag ttactgcagc | 180 |
| tccagcagct gctccagcag tccccaccac aggccccgtt gcccatggct gtcagccggg | 240 |
| ggctcccccc gcagcagcca cagcagccgc ttctgaatct ccagggcacc aactcagcct | 300 |
| ccctcctcaa cggctccatg ctgcagagag cttttgctttt acagcagttg caaggtaacc | 360 |
| tccgaggcta tggcatggca tccccaggcc tcgcagcccc agcctcaca cccccacaac | 420 |
| tggccactcc aaatttgcaa cagttctttc cccaggccac tcgccagtcc ttgctgggac | 480 |
| ctcctcctgt tggggtcccc atgaaccctt cccagttcaa cctttcagga cggaaccccc | 540 |
| agaaacaggc ccggacctcc tcctctacca cccccaatcg aaaggattct tcttctcaga | 600 |
| caatgcctgt ggaagacaag tcagaccccc cagggggtc tgaggaagcc gcagagcccc | 660 |
| ggatggacac accagaagac caagatttac cgccctgccc agaggacatc gccaaggaaa | 720 |

```
aacgcactcc agcacctgag cctgagcctt gtgaggcgtc cgagctgcca gcaaagagat    780
tgaggagctc agaagagccc acagagaagg aacctccagg gcagttacag gtgaaggccc    840
agccgcaggc ccggatgaca gtaccgaaac agacacagac accagacctg ctgcctgagg    900
ccctggaagc ccaagtgctg ccacgattcc agccacgggc cctgcaggtc caggcccagg    960
tgcagtcaca gactcagccg cggataccat ccacagacac ccaggtgcag ccaaagctgc   1020
agaagcaggc gcaaacacag acctctccag agcacttagt gctgcaacag aagcaggtgc   1080
agccacagct gcagcaggag gcagagccac agaagcaggt gcagccacag gtacagccac   1140
aggcacattc acagggccca aggcaggtgc agctgcagca ggaggcagag ccgctgaagc   1200
aggtgcagcc acaggtgcag ccccaggcac attcacagcc cccaaggcag gtgcagctgc   1260
agctgcagaa gcaggtccag acacagacat atccacaggt ccacacacag gcacagccaa   1320
gcgtccagcc acaggagcat cctccagcgc aggtgtcagt acagccacca gagcagaccc   1380 atgagcagc tcacacccag ccgcaggtgt cgttgctggc tccagagcaa acaccagttg   1440
tggttcatgt ctgcgggctg gagatgccac ctgatgcagt agaagctggt ggaggcatgg   1500
aaaagacctt gccagagcct gtgggcaccc aagtcagcat ggaagagatt cagaatgagt   1560
cggcctgtgg cctagatgtg ggagaatgtg aaaacagagc gagagagatg ccaggggtat   1620
ggggcgccgg gggctccctg aaggtcacca ttctgcagag cagtgacagc cgggccttta   1680
gcactgtacc cctgacacct gtccccgcc ccagtgactc cgtctcctcc acccctgcgg    1740
ctaccagcac tccctctaag caggccctcc agttcttctg ctacatctgc aaggccagct   1800
gctccagcca gcaggagttc caggaccaca tgtcggagcc tcagcaccag cagcggctag   1860
gggagatcca gcacatgagc caagcctgcc tcctgtccct gctgcccgtg ccccgggacg   1920
tcctggagac agaggatgag gagcctccac caaggcgctg gtgcaacacc tgccagctct   1980
actacatggg ggacctgatc caacaccgca ggacacagga ccacaagatt gccaaacaat   2040
ccttgcgacc cttctgcacc gtttgcaacc gctacttcaa aaccccctcgc aagtttgtgg   2100 agcacgtgaa gtcccagggg cataaggaca agccaaggga gctgaagtcg cttgagaaag   2160
aaattgctgg ccaagatgag gaccacttca ttacagtgga cgctgtgggt tgcttcgagg   2220
gtgatgaaga agaggaagag gatgatgagg atgaagaaga gatcgaggtt gaggaggaac   2280
tctgcaagca ggtgaggtcc agagatatat ccagagagga gtggaagggc tcggagacct   2340
acagccccaa tactgcatat ggtgtggact tcctggtgcc cgtgatgggc tatatctgcc   2400
gcatctgcca caagttctat cacagcaact caggggcaca gctctcccac tgcaagtccc   2460
tgggccactt tgagaacctg cagaaataca aggcggccaa gaaccccagc cccaccaccc   2520
gacctgtgag ccgccggtgc gcaatcaacg cccggaacgc tttgacagcc ctgttcacct   2580
ccagcggccg cccaccctcc cagcccaaca cccaggacaa acacccagc aaggtgacgg    2640 ctcgaccctc ccagccccca ctacctcggc gctcaacccg cctcaaaacc tgatagaggg   2700
acctccctgt ccctggcctg cctgggtcca gatctgctaa tgcttttttag gagtctgcct   2760 ggaaactttg acatggttca tgttttttact caaaatccaa taaaacaagg tagtttggct   2820
gtgcaaaaaa aaaaaaaaaa aaaaaaaaaa                                     2850

<210> SEQ ID NO 68
<211> LENGTH: 2907
<212> TYPE: DNA
<213> ORGANISM: Homo sapiens
```

```
<400> SEQUENCE: 68
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggccccgtt gcccatggct gtcagccggg     240
ggctcccccc gcagcagcca cagcagccgc ttctgaatct ccagggcacc aactcagcct     300
ccctcctcaa cggctccatg ctgcagagag ctttgctttt acagcagttg caaggactgg     360
accagtttgc aatgccacca gccacgtatg acactgccgg tctcaccatg cccacagcaa     420
cactgggtaa cctccgaggc tatggcatgg catccccagg cctcgcagcc cccagcctca     480
caccccaca actggccact ccaaatttgc aacagttctt tccccaggcc actcgccagt     540
ccttgctggg acctcctcct gttggggtcc ccatgaaccc ttcccagttc aacctttcag     600
gacggaaccc ccagaaacag gcccggacct cctcctctac cacccccaat cgaaagacaa     660
tgcctgtgga agacaagtca gacccccag aggggtctga ggaagccgca gagccccgga     720
tggacacacc agaagaccaa gatttaccgc cctgcccaga ggacatcgcc aaggaaaaac     780
gcactccagc acctgagcct gagccttgtg aggcgtccga gctgccagca aagagattga     840
ggagctcaga gagcccaca gagaaggaac ctccagggca gttacaggtg aaggcccagc     900
cgcaggcccg gatgacagta ccgaaacaga cacagacacc agacctgctg cctgaggccc     960
tggaagccca agtgctgcca cgattccagc cacgggtcct gcaggtccag gcccaggtgc    1020
agtcacagac tcagccgcgg ataccatcca cagacaccca ggtgcagcca aagctgcaga    1080
agcaggcgca aacacagacc tctccagagc acttagtgct gcaacagaag caggtgcagc    1140
cacagctgca gcaggaggca gagccacaga agcaggtgca gccacaggta cagccacagg    1200
cacattcaca gggcccaagg caggtgcagc tgcagcagga ggcagagccg ctgaagcagg    1260
tgcagccaca ggtgcagccc caggcacatt cacagccccc aaggcaggtg cagctgcagc    1320
tgcagaagca ggtccagaca cagacatatc cacaggtcca cacacaggca cagccaagcg    1380
tccagccaca ggagcatcct ccagcgcagg tgtcagtaca gccaccagag cagacccatg    1440
agcagcctca cacccagccg caggtgtcgt tgctggctcc agagcaaaca ccagttgtgg    1500
ttcatgtctg cgggctggag atgccacctg atgcagtaga agctggtgga ggcatggaaa    1560
agaccttgcc agagcctgtg ggcacccaag tcagcatgga agagattcag aatgagtcgg    1620
cctgtggcct agatgtggga gaatgtgaaa acagagcgag agagatgcca ggggtatggg    1680
gcgccggggg ctccctgaag gtcaccattc tgcagagcag tgacagccgg gccttttagca   1740
ctgtaccccct gacacctgtc cccgcccca gtgactccgt ctcctccacc cctgcggcta    1800
ccagcactcc ctctaagcag gccctccagt tcttctgcta catctgcaag gccagctgct    1860
ccagccagca ggagttccag gaccacatgt cggagcctca gcaccagcag cggctagggg    1920
agatccagca catgagccaa gcctgcctcc tgtccctgct gcccgtgccc cgggacgtcc    1980
tggagacaga ggatgaggag cctccaccaa ggcgctggtg caacacctgc cagctctact    2040
acatggggga cctgatccaa caccgcagga cacaggacca caagattgcc aaacaatcct    2100
tgcgaccctt ctgcaccgtt tgcaaccgct acttcaaaac ccctcgcaag tttgtggagc    2160
acgtgaagtc ccagggcat aaggacaaag ccaaggagct gaagtcgctt gagaagaaa      2220
ttgctggcca agatgaggac cacttcatta cagtggacgc tgtgggttgc ttcgagggtg    2280
atgaagaaga ggaagaggat gatgaggatg aagaagagat cgaggttgag gaggaactct    2340
```

```
gcaagcaggt gaggtccaga gatatatcca gagaggagtg gaagggctcg gagacctaca    2400
gccccaatac tgcatatggt gtggacttcc tggtgcccgt gatgggctat atctgccgca    2460
tctgccacaa gttctatcac agcaactcag gggcacagct ctcccactgc aagtccctgg    2520
gccactttga gaacctgcag aaatacaagg cggccaagaa ccccagcccc accacccgac    2580
ctgtgagccg ccggtgcgca atcaacgccc ggaacgcttt gacagccctg ttcacctcca    2640
gcggccgccc accctcccag cccaacaccc aggacaaaac cccagcaag gtgacggctc     2700 gaccctccca gccccacta cctcggcgct caacccgcct caaaacctga tagagggacc     2760
tccctgtccc tggcctgcct gggtccagat ctgctaatgc ttttaggag tctgcctgga    2820 aactttgaca tggttcatgt ttttactcaa aatccaataa aacaaggtag tttggctgtg    2880
caaaaaaaaa aaaaaaaaaa aaaaaaa                                        2907

<210> SEQ ID NO 69
<211> LENGTH: 2836
<212> TYPE: DNA
<213> ORGANISM: Homo sapiens

<400> SEQUENCE: 69
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggcccccgtt gcccatggct gtcagccggg    240
ggctcccccc gcagcagcca cagcagccgc ttctgaatct ccagggcacc aactcagcct    300
ccctcctcaa cggctccatg ctgcagagag ctttgctttt acagcagttg caaggactgg    360
accagtttgc aatgccacca gccacgtatg acactgccgg tctcaccatg cccacagcaa    420
cactgggtaa cctccgaggc tatggcatgg catcccagg cctcgcagcc cccagcctca    480
cacccccaca actggccact ccaaatttgc aacagttctt tccccaggcc actcgccagt    540
ccttgctggg acctcctcct gttggggtcc ccatgaaccc ttcccagttc aacctttcag    600
gacggaaccc ccagaaacag gcccggacct cctcctctac caccccaat cgaaaggatt    660 cttcttctca gacaatgcct gtggaagaca gtcagaccc cccagagggg tctgaggaag    720
ccgcagagcc ccgatggac acaccagaag accaagattt accgccctgc ccagaggaca    780
tcgccaagga aaaacgcact ccagcacctg agcctgagcc ttgtgaggcg tccgagctgc    840
cagcaaagag attgaggagc tcagaagagc ccacagagaa ggaacctcca gggcagttac    900
aggtgaaggc ccagccgcag gcccggatga cagtaccgaa acagacacag acaccagacc    960
tgctgcctga ggcctggaa gcccaagtgc tgccacgatt ccagccacgg gtcctgcagg    1020
tccaggccca ggtgcagtca cagactcagc cgcggatacc atccacagac acccaggtgc    1080
agccaaagct gcagaagcag gcgcaaaacac agacctctcc agagcactta gtgctgcaac    1140
agaagcaggt gcagccacag ctgcagcagg aggcagagcc acagaagcag gtgcagccac    1200
aggtacagcc acaggcacat tcacagggcc caaggcaggt gcagctgcag caggaggcag    1260
agccgctgaa gcaggtgcag acaggtccac acacaggcac agccaagcgt ccagccacag    1320
gagcatcctc cagcgcaggt gtcagtacag ccaccagagc agacccatga gcagcctcac    1380
acccagccgc aggtgtcgtt gctggctcca gagcaaacac cagttgtggt tcatgtctgc    1440
gggctggaga tgccacctga tgcagtagaa gctggtggag gcatggaaaa gaccttgcca    1500
```

```
gagcctgtgg gcacccaagt cagcatggaa gagattcaga atgagtcggc ctgtggccta      1560
gatgtgggag aatgtgaaaa cagagcgaga gagatgccag gggtatgggg cgccgggggc      1620
tccctgaagg tcaccattct gcagagcagt gacagccggg cctttagcac tgtacccctg      1680
acacctgtcc cccgcccag tgactccgtc tcctccaccc ctgcggctac cagcactccc       1740
tctaagcagg ccctccagtt cttctgctac atctgcaagg ccagctgctc cagccagcag      1800
gagttccagg accacatgtc ggagcctcag caccagcagc ggctagggga gatccagcac      1860
atgagccaag cctgcctcct gtccctgctg cccgtgcccc gggacgtcct ggagacagag      1920
gatgaggagc ctccaccaag cgctggtgc aacacctgcc agctctacta catgggggac       1980
ctgatccaac accgcaggac acaggaccac aagattgcca acaatccttg cgacccttc       2040 tgcaccgttt gcaaccgcta cttcaaaacc cctcgcaagt tgtggagca cgtgaagtcc       2100 caggggcata aggacaaagc caaggagctg aagtcgcttg agaaagaaat tgctggccaa      2160
gatgaggacc acttcattac agtggacgct gtgggttgct tcgagggtga tgaagaagag      2220
gaagaggatg atgaggatga agaagagatc gaggttgagg aggaactctg caagcaggtg      2280
aggtccagag atatatccag agaggagtgg aagggctcgg agacctacag ccccaatact      2340
gcatatggtg tggacttcct ggtgcccgtg atgggctata tctgccgcat ctgccacaag      2400
ttctatcaca gcaactcagg ggcacagctc tcccactgca gtccctggg ccactttgag      2460 aacctgcaga atacaaggc ggccaagaac cccagcccca ccaccgacc tgtgagccgc       2520 cggtgcgcaa tcaacgcccg gaacgctttg acagccctgt tcacctccag cggccgccca      2580
ccctcccagc ccaacaccca ggacaaaaca cccagcaagg tgacggctcg accctcccag      2640
cccccactac ctcggcgctc aacccgcctc aaaacctgat agagggacct ccctgtccct      2700
ggcctgcctg gtccagatc tgctaatgct ttttaggagt ctgcctggaa actttgacat      2760
ggttcatgtt tttactcaaa atccaataaa acaaggtagt ttggctgtgc aaaaaaaaaa      2820
aaaaaaaaaa aaaaaa                                                      2836

<210> SEQ ID NO 70
<211> LENGTH: 2754
<212> TYPE: DNA
<213> ORGANISM: Homo sapiens

<400> SEQUENCE: 70
tgggggctgc ggggccggcc catccgtggg ggcgacttga gcgttgaggg cgcgcgggga        60
ggcgagccac catgttcagc cagcagcagc agcagctcca gcaacagcag cagcagctcc       120
agcagttaca gcagcagcag ctccagcagc agcaattgca gcagcagcag ttactgcagc       180
tccagcagct gctccagcag tccccaccac aggcccccgtt gcccatggct gtcagccggg      240
ggctcccccc gcagcagcca cagcagccgc ttctgaatct ccagggcacc aactcagcct       300
ccctcctcaa cggctccatg ctgcagagag ctttgctttt acagcagttg caaggactgg       360
accagtttgc aatgccacca gccacgtatg acactgccgg tctcaccatg cccacagcaa       420
cactgggtaa cctccgaggc tatggcatgg catcccagg cctcgcagcc ccagcctca        480 cacccccaca actggccact ccaaatttgc aacgttctt tccccaggcc actcgccagt       540
ccttgctggg acctcctcct gttggggtcc ccatgaaccc ttcccagttc aacctttcag      600
gacggaaccc ccagaaacag gccggacct cctcctctac caccccaat cgaaaggatt       660 cttcttctca gacaatgcct gtggaagaca agtcagaccc cccagagggg tctgaggaag      720
ccgcagagcc ccggatggac acaccagaag accaagattt accgccctgc ccagaggaca      780
```

```
tcgccaagga aaaacgcact ccagcacctg agcctgagcc ttgtgaggcg tccgagctgc      840
cagcaaagag attgaggagc tcagaagagc ccacagagaa ggaacctcca gggcagttac      900
aggtgaaggc ccagccgcag gcccggatga cagtaccgaa acagacacag acaccagacc      960
tgctgcctga ggccctggaa gcccaagtgc tgccacgatt ccagccacgg gtcctgcagg     1020
tccaggccca ggtgcagtca cagactcagc cgcggatacc atccacagac acccaggtgc     1080
agccaaagct gcagaagcag gcgcaaacac agacctctcc agagcactta gtgctgcaac     1140
agaagcaggt gcagccacag ctgcagcagg aggcagagcc acagaagcag gtgcagccac     1200
aggtccacac acaggcacag ccaagcgtcc agcacagga gcatcctcca gcgcaggtgt       1260
cagtacagcc accagagcag acccatgagc agcctcacac ccagccgcag gtgtcgttgc     1320
tggctccaga gcaaacacca gttgtggttc atgtctgcgg gctggagatg ccacctgatg     1380
cagtagaagc tggtggaggc atggaaaaga ccttgccaga gcctgtgggc acccaagtca     1440
gcatggaaga gattcagaat gagtcggcct gtggcctaga tgtgggagaa tgtgaaaaca     1500
gagcgagaga gatgccaggg gtatggggcg ccgggggctc cctgaaggtc accattctgc     1560
agagcagtga cagccgggcc tttagcactg taccccctgac acctgtcccc cgccccagtg    1620
actccgtctc ctccaccct gcggctacca gcactccctc taagcaggcc ctccagttct      1680
tctgctacat ctgcaaggcc agctgctcca gccagcagga gttccaggac acatgtcgg     1740 agcctcagca ccagcagcgg ctaggggaga tccagcacat gagccaagcc tgcctcctgt     1800
ccctgctgcc cgtgccccgg gacgtcctgg agacagagga tgaggagcct ccaccaaggc     1860
gctggtgcaa cacctgccag ctctactaca tgggggacct gatccaacac cgcaggacac     1920
aggaccacaa gattgccaaa caatccttgc gaccccttctg caccgtttgc aaccgctact    1980
tcaaaacccc tcgcaagttt gtggagcacg tgaagtccca ggggcataag acaaagcca     2040 aggagctgaa gtcgcttgag aaagaaattg ctggccaaga tgaggaccac ttcattacag     2100
tggacgctgt gggttgcttc gagggtgatg aagaagagga agaggatgat gaggatgaag     2160
aagagatcga ggttgaggag gaactctgca agcaggtgag gtccagagat atatccagag     2220
aggagtggaa gggctcggag acctacagcc ccaatactgc atatggtgtg gacttcctgg     2280
tgcccgtgat gggctatatc tgccgcatct gccacaagtt ctatcacagc aactcagggg     2340
cacagctctc ccactgcaag tccctgggcc actttgagaa cctgcagaaa tacaaggcgg     2400
ccaagaaccc cagccccacc acccgacctg tgagccgccg gtgcgcaatc aacgcccgga     2460
acgctttgac agccctgttc acctccagcg gccgcccacc ctcccagccc aacacccagg     2520
acaaaacacc cagcaaggtg acggctcgac cctcccagcc cccactacct cggcgctcaa     2580
cccgcctcaa aacctgatag agggacctcc ctgtccctgg cctgcctggg tccagatctg     2640
ctaatgcttt ttaggagtct gcctggaaac tttgacatgg ttcatgtttt tactcaaaat     2700
ccaataaaac aaggtagttt ggctgtgcaa aaaaaaaaa aaaaaaaaaa aaaa            2754
```

<210> SEQ ID NO 71
<211> LENGTH: 2587
<212> TYPE: DNA
<213> ORGANISM: Homo sapiens

<400> SEQUENCE: 71

```
tgggggctgc ggggccggcc catccgtggg ggcgacttga gcgttgaggg cgcgcgggga       60
ggcgagccac catgttcagc cagcagcagc agcagctcca gcaacagcag cagcagctcc      120
```

```
agcagttaca gcagcagcag ctccagcagc agcaattgca gcagcagcag ttactgcagc      180
tccagcagct gctccagcag tccccaccac aggccccgtt gcccatggct gtcagccggg      240 ggctccccccc gcagcagcca cagcagccgc ttctgaatct ccagggcacc aactcagcct     300
ccctcctcaa cggctccatg ctgcagagag ctttgctttt acagcagttg caaggactgg      360
accagtttgc aatgccacca gccacgtatg acactgccgg tctcaccatg cccacagcaa      420
cactgggtaa cctccgaggc tatggcatgg catccccagg cctcgcagcc cccagcctca      480
cacccccaca actggccact ccaaatttgc aacagttctt tccccaggcc actcgccagt      540
ccttgctggg acctcctcct gttggggtcc ccatgaaccc ttcccagttc aacctttcag      600
gacggaaccc ccagaaacag gcccggacct cctcctctac caccccccaat cgaaaggatt     660 cttcttctca gacaatgcct gtggaagaca agtcagaccc cccagagggg tctgaggaag      720
ccgcagagcc ccggatggac acaccagaag accaagattt accgccctgc cagaggaca      780 tcgccaagga aaaacgcact ccagcacctg agcctgagcc ttgtgaggcg tccgagctgc      840
cagcaaagag attgaggagc tcagaagagc ccacagagaa ggaacctcca gggcagttac      900
aggtgaaggc ccagccgcag gcccggatga cagtaccgaa acagacacag acaccagacc      960
tgctgcctga ggccctggaa gcccaagtgc tgccacgatt ccagcacgg gtcctgcagg     1020 tccaggcctc cacaggtcca cacacaggca cagccaagcg tccagccaca ggagcatcct     1080
ccagcgcagg tgtcagtaca gccaccagag cagacccatg agcagcctca cacccagccg     1140
caggtgtcgt tgctggctcc agagcaaaca ccagttgtgg ttcatgtctg cgggctggag     1200
atgccacctg atgcagtaga agctggtgga ggcatggaaa agaccttgcc agagcctgtg     1260
ggcacccaag tcagcatgga agagattcag aatgagtcgg cctgtggcct agatgtggga     1320
gaatgtgaaa acagagcgag agagatgcca ggggtatggg gcgccggggg ctccctgaag     1380
gtcaccattc tgcagagcag tgacagccgg gcctttagca ctgtacccct gacacctgtc     1440 cccccgcccca gtgactccgt ctcctccacc cctgcggcta ccagcactcc ctctaagcag    1500
gccctccagt tcttctgcta catctgcaag gccagctgct ccagccagca ggagttccag     1560
gaccacatgt cggagcctca gcaccagcag cggctagggg agatccagca catgagccaa     1620
gcctgcctcc tgtccctgct gcccgtgccc cgggacgtcc tggagacaga ggatgaggag     1680
cctccaccaa ggcgctggtg caacacctgc cagctctact acatggggga cctgatccaa     1740
caccgcagga cacaggacca caagattgcc aaacaatcct tgcgaccctt ctgcaccgtt     1800
tgcaaccgct acttcaaaac ccctcgcaag tttgtggagc acgtgaagtc ccaggggcat     1860
aaggacaaag ccaaggagct gaagtcgctt gagaaagaaa ttgctggcca agatgaggac     1920
cacttcatta cagtggacgc tgtgggttgc ttcgagggtg atgaagaaga ggaagaggat     1980
gatgaggatg aagaagagat cgaggttgag gaggaactct gcaagcaggt gaggtccaga     2040
gatatatcca gagaggagtg aaagggctcg gagacctaca gccccaatac tgcatatggt     2100
gtggacttcc tggtgcccgt gatgggctat atctgccgca tctgccacaa gttctatcac     2160
agcaactcag gggcacagct ctcccactgc aagtccctgg ccactttgaa gaacctgcag     2220
aaatacaagg cggccaagaa ccccagcccc accaccgac ctgtgagccg ccggtgcgca     2280
atcaacgccc ggaacgcttt gacagccctg ttcacctcca gcggccgccc accctcccag     2340
cccaacaccc aggacaaaac acccagcaag gtgacggctc gaccctccca gcccccacta     2400
cctcggcgct caaccccgcct caaaacctga tagagggacc tccctgtccc tggcctgcct     2460
gggtccagat ctgctaatgc ttttaggag tctgcctgga aactttgaca tggttcatgt     2520
```

-continued

| | |
|---|---|
| ttttactcaa aatccaataa aacaaggtag tttggctgtg caaaaaaaaa aaaaaaaaaa | 2580 |
| aaaaaaa | 2587 |

<210> SEQ ID NO 72
<211> LENGTH: 2898
<212> TYPE: DNA
<213> ORGANISM: Homo sapiens

<400> SEQUENCE: 72

| | |
|---|---|
| tgggggctgc ggggccggcc catccgtggg ggcgacttga gcgttgaggg cgcgcgggga | 60 |
| ggcgagccac catgttcagc cagcagcagc agcagctcca gcaacagcag cagcagctcc | 120 |
| agcagttaca gcagcagcag ctccagcagc agcaattgca gcagcagcag ttactgcagc | 180 |
| tccagcagct gctccagcag tccccaccac aggccccgtt gcccatggct gtcagccggg | 240 |
| ggctccccccc gcagcagcca cagcagccgc ttctgaatct ccagggcacc aactcagcct | 300 |
| ccctcctcaa cggctccatg ctgcagagag ctttgctttt acagcagttg caaggactgg | 360 |
| accagtttgc aatgccacca gccacgtatg acactgccgg tctcaccatg cccacagcaa | 420 |
| cactgggtaa cctccgaggc tatggcatgg catccccagg cctcgcagcc cccagcctca | 480 |
| cacccccaca actggccact ccaaatttgc aacagttctt tccccaggcc actcgccagt | 540 |
| ccttgctggg acctcctcct gttggggtcc ccatgaaccc ttcccagttc aacctttcag | 600 |
| gacggaaccc ccagaaacag gcccggacct cctcctctac caccccaat cgaaaggatt | 660 |
| cttcttctca gacaatgcct gtggaagaca agtcagaccc cccagagggg tctgaggaag | 720 |
| ccgcagagcc ccggatggac acaccagaag accaagattt accgccctgc cagaggaca | 780 |
| tcgccaagga aaaacgcact ccagcacctg agcctgagcc ttgtgaggcg tccgagctgc | 840 |
| cagcaaagag attgaggagc tcagaagagc ccacagagaa ggaacctcca gggcagttac | 900 |
| aggtgaaggc ccagccgcag gcccggatga cagtaccgaa acagacacag acaccagacc | 960 |
| tgctgcctga ggccctggaa gcccaagtgc tgccacgatt ccagccacgg gtcctgcagg | 1020 |
| tccaggccca ggtgcagtca cagactcagc cgcggatacc atccacagac acccaggtgc | 1080 |
| agccaaagct gcagaagcag gcgcaaacac agacctctcc agagcactta gtgctgcaac | 1140 |
| agaagcaggt gcagccacag ctgcagcagg aggcagagcc acagaagcag gtgcagccac | 1200 |
| aggtacagcc acaggcacat tcacagggcc caaggcaggt gcagctgcag caggaggcag | 1260 |
| agccgctgaa gcaggtgcag ccacaggtgc agccccaggc acattcacag ccccaaggc | 1320 |
| aggtgcagct gcagctgcag aagcaggtcc agacacagac atatccacag gtccacacac | 1380 |
| aggcacagcc aagcgtccag ccacaggagc atcctccagc gcaggtgtca gtacagccac | 1440 |
| cagagcagac ccatgagcag cctcacaccc agccgcaggt gtcgttgctg gctccagagc | 1500 |
| aaacaccagt tgtggttcat gtctgcgggc tggagatgcc acctgatgca gtagaagctg | 1560 |
| gtggaggcat ggaaaagacc ttgccagagc ctgtgggcac ccaagtcagc atggaagaga | 1620 |
| ttcagaatga gtcggcctgt ggcctagatg tgggagaatg tgaaacaga gcgagagaga | 1680 |
| tgccaggggt atgggcgcc gggggctccc tgaaggtcac cattctgcag agcagtgaca | 1740 |
| gccgggcctt tagcactgta cccctgacac ctgtccccg cccagtgac tccgtctcct | 1800 |
| ccaccccctgc ggctaccagc actccctcta gcaggccct ccagttcttc tgctacatct | 1860 |
| gcaaggccag ctgctccagc cagcaggagt tccaggacca catgtcggag cctcagcacc | 1920 |
| agcagcggct aggggagatc cagcacatga gccaagcctg cctcctgtcc ctgctgcccg | 1980 |

| | |
|---|---|
| tgccccggga cgtcctggag acagaggatg aggagcctcc accaaggcgc tggtgcaaca | 2040 |
| cctgccagct ctactacatg ggggacctga tccaacaccg caggacacag gaccacaaga | 2100 |
| ttgccaaaca atccttgcga cccttctgca ccgtttgcaa ccgctacttc aaaacccctc | 2160 |
| gcaagtttgt ggagcacgtg aagtcccagg gcataagga caaagccaag gagctgaagt | 2220 |
| cgcttgagaa agaaattgct ggccaagatg aggaccactt cattacagtg gacgctgtgg | 2280 |
| gttgcttcga gggtgatgaa gaagaggaag gaggatgatga ggatgaagaa gagatcgagg | 2340 |
| tgaggtccag agatatatcc agagaggagt ggaagggctc ggagacctac agccccaata | 2400 |
| ctgcatatgg tgtggacttc ctggtgcccg tgatgggcta tatctgccgc atctgccaca | 2460 |
| agttctatca cagcaactca ggggcacagc tctcccactg caagtccctg ggccactttg | 2520 |
| agaacctgca gaaatacaag gcggccaaga accccagccc caccaccga cctgtgagcc | 2580 |
| gccggtgcgc aatcaacgcc cggaacgctt tgacagccct gttcacctcc agcggccgcc | 2640 |
| caccctccca gcccaacacc caggacaaaa cacccagcaa ggtgacggct cgaccctccc | 2700 |
| agcccccact acctcggcgc tcaacccgcc tcaaaacctg atagagggac ctccctgtcc | 2760 |
| ctggcctgcc tgggtccaga tctgctaatg cttttaggga gtctgcctgg aaactttgac | 2820 |
| atggttcatg tttttactca aaatccaata aaacaaggta gtttggctgt gcaaaaaaaa | 2880 |
| aaaaaaaaaa aaaaaaaa | 2898 |

<210> SEQ ID NO 73
<211> LENGTH: 2883
<212> TYPE: DNA
<213> ORGANISM: Homo sapiens

<400> SEQUENCE: 73

| | |
|---|---|
| tgggggctgc ggggccggcc catccgtggg ggcgacttga gcgttgaggg cgcgcgggga | 60 |
| ggcgagccac catgttcagc cagcagcagc agcagctcca gcaacagcag cagcagctcc | 120 |
| agcagttaca gcagcagcag ctccagcagc agcaattgca gcagcagcag ttactgcagc | 180 |
| tccagcagct gctccagcag tccccaccac aggccccgtt gcccatggct gtcagccggg | 240 |
| ggctcccccc gcagcagcca cagcagccgc ttctgaatct ccagggcacc aactcagcct | 300 |
| ccctcctcaa cggctccatg ctgcagagag ctttgctttt acagcagttg caaggactgg | 360 |
| accagtttgc aatgccacca gccacgtatg acactgccgg tctcaccatg cccacagcaa | 420 |
| cactgggtaa cctccgaggc tatggcatgg catccccagg cctcgcagcc cccagcctca | 480 |
| caccccacac actggccact ccaaatttgc aacagttctt tccccaggcc actcgccagt | 540 |
| ccttgctggg acctcctcct gttggggtcc ccatgaaccc ttcccagttc aacctttcag | 600 |
| gacggaaccc ccagaaacag gcccggacct cctcctctac cacccccaat cgaaagacaa | 660 |
| tgcctgtgga agacaagtca gacccccag aggggtctga ggaagccgca gagccccgga | 720 |
| tggacacacc agaagaccaa gatttaccgc cctgcccaga ggacatcgcc aaggaaaaac | 780 |
| gcactccagc acctgagcct gagccttgtg aggcgtccga gctgccagca aagagattga | 840 |
| ggagctcaga agagcccaca gagaaggaac ctccagggca gttacaggtg aaggcccagc | 900 |
| cgcaggcccg gatgacagta ccgaaacaga cacagacacc agacctgctg cctgaggccc | 960 |
| tggaagccca agtgctgcca cgattccagc cacgggtcct gcaggtccag gcccaggtgc | 1020 |
| agtcacagac tcagccgcgg ataccatcca gacacccca ggtgcagcca agctgcagaa | 1080 |
| agcaggcgca aacacagacc tctccagagc acttagtgct gcaacagaag caggtgcagc | 1140 |
| cacagctgca gcaggaggca gagccacaga agcaggtgca gccacaggta cagccacagg | 1200 |

-continued

```
cacattcaca gggcccaagg caggtgcagc tgcagcagga ggcagagccg ctgaagcagg    1260
tgcagccaca ggtgcagccc caggcacatt cacagccccc aaggcaggtg cagctgcagc    1320
tgcagaagca ggtccagaca cagacatatc cacaggtcca cacacaggca cagccaagcg    1380
tccagccaca ggagcatcct ccagcgcagg tgtcagtaca gccaccagag cagacccatg    1440
agcagcctca cacccagccg caggtgtcgt tgctggctcc agagcaaaca ccagttgtgg    1500
ttcatgtctg cgggctggag atgccacctg atgcagtaga agctggtgga ggcatggaaa    1560
agaccttgcc agagcctgtg ggcacccaag tcagcatgga agagattcag aatgagtcgg    1620
cctgtggcct agatgtggga gaatgtgaaa acagagcgag agagatgcca ggggtatggg    1680
gcgccggggg ctccctgaag gtcaccattc tgcagagcag tgacagccgg gcctttagca    1740
ctgtacccct gacacctgtc ccccgcccca gtgactccgt ctcctccacc cctgcggcta    1800
ccagcactcc ctctaagcag gccctccagt tcttctgcta catctgcaag gccagctgct    1860
ccagccagca ggagttccag gaccacatgt cggagcctca gcaccagcag cggctagggg    1920
agatccagca catgagccaa gcctgcctcc tgtccctgct gcccgtgccc cgggacgtcc    1980
tggagacaga ggatgaggag cctccaccaa ggcgctggtg caacacctgc cagctctact    2040
acatggggga cctgatccaa caccgcagga cacaggacca caagattgcc aaacaatcct    2100
tgcgacccct ctgcaccgtt tgcaaccgct acttcaaaac ccctcgcaag tttgtgggagc    2160 acgtgaagtc ccaggggcat aaggacaaag ccaaggagct gaagtcgctt gagaaagaaa    2220
ttgctggcca agatgaggac cacttcatta cagtggacgc tgtgggttgc ttcgagggtg    2280
atgaagaaga ggaagaggat gatgaggatg aagaagagat cgaggtgagg tccagagata    2340
tatccagaga ggagtggaag ggctcggaga cctacagccc caatactgca tatggtgtgg    2400
acttcctggt gcccgtgatg ggctatatct gccgcatctg ccacaagttc tatcacagca    2460
actcaggggc acagctctcc cactgcaagt ccctgggcca ctttgagaac ctgcagaaat    2520
acaaggcggc caagaacccc agccccacca cccgacctgt gagccgccgg tgcgcaatca    2580
acgcccggaa cgctttgaca gccctgttca cctccagcgg ccgccacccc tcccagccca    2640
acacccagga caaaacaccc agcaaggtga cggctcgacc ctcccagccc ccactacctc    2700
ggcgctcaac ccgcctcaaa acctgataga gggacctccc tgtccctggc ctgcctgggt    2760
ccagatctgc taatgctttt taggagtctg cctggaaact ttgacatggt tcatgttttt    2820
actcaaaatc caataaaaca aggtagtttg gctgtgcaaa aaaaaaaaaa aaaaaaaaa    2880 aaa    2883
```

<210> SEQ ID NO 74
<211> LENGTH: 33
<212> TYPE: PRT
<213> ORGANISM: Homo sapiens

<400> SEQUENCE: 74

Gln Gln Leu Gln Gln Leu Gln Gln Gln Gln Leu Gln Gln Gln Gln Leu
1               5                   10                  15

Gln Gln Gln Gln Leu Leu Gln Leu Gln Gln Leu Leu Gln Gln Ser Pro
            20                  25                  30

Pro

REPLICATION PROTEIN

REFERENCE TO RELATED APPLICATIONS

This application is a continuation of U.S. patent application Ser. No. 12/888,238, filed Sep. 22, 2010, which was a continuation of U.S. patent application Ser. No. 10/537,228, filed Jan. 13, 2006, now U.S. Pat. No. 7,833,702, which claims the benefit under 35 U.S.C. §371 of PCT Application Serial No. PCT/GB2003/005334, filed Dec. 5, 2003, which claims the benefit of Great Britain Application Serial No. 0228337.2, filed Dec. 5, 2002 and U.S. Provisional Application Ser. No. 60/433,925, filed Dec. 17, 2002, the disclosures of which are incorporated by reference herein in their entireties.

FIELD OF THE INVENTION

This invention relates to a screening method for the identification of agents which modulate the activity of a DNA replication protein as a target for intervention in cancer therapy and includes agents which modulate said activity. The invention also relates to the use of the DNA replication protein, and its RNA transcripts in the prognosis and diagnosis of proliferative disease e.g., cancer.

BACKGROUND

Initiation of DNA replication is a major control point in the mammalian cell cycle, and the point of action of many gene products that are mis-regulated in cancer (Hanahan and Weinberg, 2000). The initiation process involves assembly of pre-replication complex proteins, which include the origin recognition complex (ORC), Cdc6, Cdt1 and Mcm proteins, at replication origins during G1 phase of the cell cycle. This is followed by the action of a second group of proteins, which facilitate loading of DNA polymerases and their accessory factors including PCNA, and the transition to S phase. The initiation process is regulated by cyclin-dependent protein kinase 2 (Cdk2), Cdc7-dbf4 and the Cdt1 inhibitor geminin (for review see Bell and Dutta, 2002). In the nucleus of S phase cells, replication forks cluster together to form hundreds of replication 'foci' or factories (Cook, 1999). Replication factories appear to be linked to a structural framework within the nucleus, however the nature of the molecules that form the link and their role in replication fork activity remains unclear.

Identification of proteins involved in eukaryotic DNA replication and analysis of the basic pathways that regulate their activity during the cell cycle has been driven largely by yeast genetics. These proteins and pathways are generally conserved from yeast to man. However, in multi-cellular organisms that differentiate down diverse developmental pathways, additional layers of complexity are being uncovered. For example, in vertebrates several proteins involved in neuronal differentiation also regulate the G1-S phase transition (Ohnuma et al., 2001). These include the cdk inhibitor p21$^{CIP1/WAF1/SDI1}$ which has been implicated in oligodendrocyte differentiation following growth arrest (Zezula et al., 2001), and in the terminal differentiation of other cell types (Parker et al., 1995).

Initiation of DNA replication can be reconstituted in vitro with isolated nuclei and cytosolic extracts from mammalian cells (Krude, 2000; Krude et al., 1997; Laman et al., 2001; Stoeber et al., 1998). Furthermore, using recombinant Cdk2 complexed with either cyclins E or A, replication complex assembly and activation of DNA synthesis can be reconstituted independently (Coverley et al., 2002). We have studied the activation step, catalyzed in vitro by cyclin A-cdk2, and shown that a relatively unstudied protein, p21-Cip1 interacting zinc-finger protein (Ciz1) functions during this stage of the initiation process. Human Ciz1 was previously identified using a modified yeast two-hybrid screen with cyclin E-p21, and biochemical analysis supported an interaction with p21 (Mitsui et al., 1999). A potential role in transcription was proposed but not demonstrated, and no other function was assigned to Ciz1. More recently the Ciz1 gene was isolated from a human medulloblastoma derived cDNA library using an in vivo tumorigenesis model (Warder and Keherly, 2003). Our analysis shows for the first time that Ciz1 plays a positive role in initiation of DNA replication.

A number of changes to chromatin bound proteins occur when DNA synthesis is activated in vitro by recombinant cyclin A-cdk2. The present invention relates to the finding that a cdc6-related antigen, p85, correlates with the initiation of DNA replication and is regulated by cyclin A-cdk2. The protein was cloned from a mouse embryo library and identified as mouse Ciz1.

In vitro analysis has shown that Ciz1 protein positively regulates initiation of DNA replication and that its activity is modulated by cdk phosphorylation at threonine 191/2, linking it to the cdk-dependent pathways that control initiation. The embryonic form mouse Ciz1 is alternately spliced, compared to predicted and somatic forms. Human Ciz1 is also alternately spliced, with variability in the same exons as mouse Ciz1. It has been found that recombinant embryonic form Ciz1 promotes initiation of mammalian DNA replication and that pediatric cancers express 'embryonic-like' forms of Ciz1. Without wishing to be held to one theory, the inventors propose that Ciz1 mis-splicing produces embryonic-like forms of Ciz1 at inappropriate times in development. This promotes inappropriately regulated DNA replication and contributes to formation or progression of cancer cell lineages.

A number of techniques have been developed in recent years which purport to specifically ablate genes and/or gene products. For example, the use of anti-sense nucleic acid molecules to bind to and thereby block or inactivate target mRNA molecules is an effective means to inhibit the production of gene products.

A much more recent technique to specifically ablate gene function is through the introduction of double stranded RNA, also referred to as inhibitory RNA (RNAi), into a cell which results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from the exonic or coding sequence of the gene which is to be ablated.

Nucleic acids and proteins have both a linear sequence structure, as defined by their base or amino acid sequence, and also a three dimensional structure which in part is determined by the linear sequence and also the environment in which these molecules are located. Conventional therapeutic molecules are small molecules, for example, peptides, polypeptides, or antibodies, which bind target molecules to produce an agonistic or antagonistic effect. It has become apparent that nucleic acid molecules also have potential with respect to providing agents with the requisite binding properties which may have therapeutic utility. These nucleic acid molecules are typically referred to as aptamers.

Aptamers are small, usually stabilized, nucleic acid molecules which comprise a binding domain for a target molecule.

Aptamers may comprise at least one modified nucleotide base. The term "modified nucleotide base" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include by example and not by way of limitation; alkylated purines and/or pyrimidines; acylated purines and/or pyrimidines; or other heterocycles.

These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyladenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; 3-D-mannosylqueosine; 5-methoxycarbonylmethyluracil; 5-methoxyuracil; 2 methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester, uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpseudouracil; 1-methylguanine; 1-methylcytosine;

Aptamers may be synthesized using conventional phosphodiester linked nucleotides using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R'; P(O) OR6; CO; or CONR'2 wherein R is H (or a salt) or alkyl (1-12C) and R6 is alkyl (1-9C) is joined to adjacent nucleotides through —O— or —S—.

Other techniques which purport to specifically ablate genes and/or gene products focus on modulating the function or interfering with the activity of protein molecules. Proteins can be targeted by chemical inhibitors drawn, for example, from existing small molecule libraries.

Antibodies, preferably monoclonal, can be raised for example in mice or rats against different protein isoforms. Antibodies, also known as immunoglobulins, are protein molecules which have specificity for foreign molecules (antigens). Immunoglobulins (Ig) are a class of structurally related proteins consisting of two pairs of polypeptide chains, one pair of light (L) (low molecular weight) chain (κ or λ), and one pair of heavy (H) chains (γ, α, μ, δ and ε), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from one L chain to anther and contributes to the binding site of the antibody. Because of its variability, it is referred to as the "variable" (V) region.

The H chains of Ig molecules are of several classes, α, μ, σ, α and γ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

Chimeric antibodies are recombinant antibodies in which all of the V-regions of a mouse or rat antibody are combined with human antibody C-regions. Humanized antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanized antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanized antibodies are designed to have less "foreign" antibody regions and are therefore thought to be less immunogenic than chimeric antibodies.

Other techniques for targeting at the protein level include the use of randomly generated peptides that specifically bind to proteins, and any other molecules which bind to proteins or protein variants and modify the function thereof.

Understanding the DNA replication process is of prime concern in the field of cancer therapy. It is known that cancer cells can become resistant to chemotherapeutic agents and can evade detection by the immune system. There is an on going need to identify targets for cancer therapy so that new agents can be identified. The DNA replication process represents a prime target for drug intervention in cancer therapy. There is a need to identify gene products which modulate DNA replication and which contribute to formation or progression of cancer cell lineages, and to develop agents that affect their function.

SUMMARY OF THE INVENTION

According to one aspect of the present invention there is provided the use of a Ciz1 nucleotide or polypeptide sequence, or any fragment or variant thereof, as a target for the identification of agents which modulate DNA replication.

As used herein the term 'fragment' or 'variant' is used to refer to any nucleic or amino acid sequence which is derived from the full length nucleotide or amino acid sequence of Ciz1 or derived from a splice variant thereof. In one embodiment of the invention the fragment is of sufficient length and/or of sufficient homology to full length Ciz1 to retain the DNA replication activity of Ciz1. In an alternative embodiment inactive Ciz1 fragments are used. The term 'fragment' or 'variant' also relates to the Ciz1 RNA transcripts described herein and protein isoforms (or parts thereof).

As used herein the term 'modulate' is used to refer to either increasing or decreasing DNA replication, above and below the levels which would normally be observed in the absence of the specific agent (i.e., any alterations in DNA replication activity which are either directly or indirectly linked to the use of the agent). The term 'modulate' also includes reference to a change of spacial or temporal organization of DNA replication.

According to an alternative aspect of the invention there is provided a screening method for the identification of agents which modulate DNA replication wherein the screening method comprises the use of Ciz1 nucleotide or polypeptide sequence or fragments or variants thereof.

Preferably the screening method comprises detecting or measuring the effect of an agent on a nucleic acid molecule selected from the groups consisting of:
  a) a nucleic acid molecule comprising a nucleic acid sequence represented in any of FIG. 14, 15, or 21 (SEQ ID NO: 45, 46, 66, 67, 68, 69, 70, 71, 72 or 73);
  b) a nucleic acid molecule which hybridizes to the nucleic acid sequence in (a) and which has Ciz1 activity or activity of a variant thereof;
  c) a nucleic acid molecule which has a nucleic acid sequence which is degenerate because of the genetic code to the sequences in a) and b); and
  d) a nucleic acid molecule derived from the genomic sequence at the Ciz1 locus or a nucleic acid molecule that hybridizes to the genomic sequence.

In one embodiment of the invention, the nucleic acid molecule is modified by deletion, substitution or addition of at least one nucleic acid residue of the nucleic acid sequence.

Alternatively the screening method comprises the steps of:
(i) forming a preparation comprising a polypeptide molecule, or an active fragment thereof, encoded by a nucleic acid molecule selected from the group consisting of:
  a) a nucleic acid molecule comprising a nucleic acid sequence represented in FIG. 14, 15 or 21 (SEQ ID NO: 45, 46, 66, 67, 68, 69, 70, 71, 72 or 73);
  b) a nucleic acid molecule which hybridizes to the nucleic acid sequence in (a) and which has Ciz1 activity or activity of a variant thereof;
  c) a nucleic acid molecule which has a nucleic acid sequence which is degenerate because of the genetic code to the sequences in a) and b) and a candidate agent to be tested;
  d) a nucleic acid molecule derived from the genomic sequence at the Ciz1 locus or a nucleic acid molecule that hybridizes to the genomic sequence; and
ii) detecting or measuring the effect of the agent on the activity of said polypeptide.

Assays for the detection of DNA replication are known in the art. Activity residing in Ciz1, or derived peptide fragments, and the effect of potential therapeutic agents on that activity would be assayed in vitro or in vivo.

In vitro assays for Ciz1 protein activity would comprise synchronized isolated G1 phase nuclei and either S phase extract or G1 phase extract supplemented with cyclin-dependent kinases. Inclusion of Ciz1 or derived peptide fragments stimulates initiation of DNA replication in these circumstances and can be monitored visually (by scoring nuclei that have incorporated fluorescent nucleotides during in vitro reactions) or by measuring incorporation of radioactive nucleotides. The assay for therapeutic reagents that interfere with Ciz1 protein function would involve looking for inhibition of DNA replication in these assays. The effect of agents on Ciz1 nuclear localization, chromatin binding, stability, modification and protein-protein interactions could also be monitored in these assays.

In vivo assays will include creation of cell and mouse models that over-express or under-express Ciz1, or derived fragments, resulting in altered cell proliferation. The preparation of transgenic animals is generally known in the art and within the ambit of the skilled person. The assay for therapeutic reagents would involve analysis of cell-cycle time, initiation of DNA replication and cancer incidence in the presence and absence of drugs that either impinge on Ciz1 protein activity, or interfere with Ciz1 production by targeting Ciz1 and its variants at the RNA level.

In a preferred method of the invention said hybridization conditions are stringent.

Stringent hybridization/washing conditions are well known in the art. For example, nucleic acid hybrids that are stable after washing in 0.1×SSC, 0.1% SDS at 60° C. It is well known in the art that optimal hybridization conditions can be calculated if the sequence of the nucleic acid is known. Typically, hybridization conditions use 4-6×SSPE (20×SSPE contains 175.3 g NaCl, 88.2 g $NaH_2PO_4H_2O$ and 7.4 g EDTA dissolved to 1 liter and the pH adjusted to 7.4); 5-10×Denhardts solution (50×Denhardts solution contains 5 g Ficoll (Type 400, Pharmacia), 5 g polyvinylpyrrolidone and 5 g bovine serum albumen; 100 μg-1.0 mg/ml sonicated salmon/herring DNA; 0.1-1.0% sodium dodecyl sulphate; optionally 40-60% deionised formamide. The hybridization temperature will vary depending on the GC content of the nucleic acid target sequence but will typically be between 42°-65° C.

In a preferred method of the invention said polypeptide is modified by deletion, substitution or addition of at least one amino acid residue of the polypeptide sequence.

A modified or variant, i.e. a fragment polypeptide and reference polypeptide, may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Preferred are variants which retain the same biological function and activity as the reference polypeptide from which it varies. Alternatively, variants include those with an altered biological function, for example variants which act as antagonists, so called "dominant negative" variants.

Alternatively or in addition, non-conservative substitutions may give the desired biological activity see Cain S A, Williams D M, Harris V, Monk P N. Selection of novel ligands from a whole-molecule randomly mutated C5a library. Protein Eng. 2001 March; 14(3):189-93, which is incorporated by reference.

A functionally equivalent polypeptide sequence according to the invention is a variant wherein one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features nucleotide or polypeptide sequences having at least 50% identity with the nucleotide or polypeptide sequences as herein disclosed, or fragments and functionally equivalent polypeptides thereof. In one embodiment, the nucleotide or polypeptide sequences have at least 75% to 85% identity, more preferably at least 90% identity, even more preferably at least 95% identity, still more preferably at least 97% identity, and most preferably at least 99% identity with the nucleotide and amino acid sequences illustrated herein.

In a preferred method of the invention said nucleic acid molecule comprises the nucleic acid sequence encoding the amino acid sequence Ciz1 in FIG. 16 (SEQ ID NO: 26) or FIG. 17 (SEQ ID NO: 47) or any variants thereof, including those described in FIGS. 20A (SEQ ID NO: 58-61) and 20B (SEQ ID NO: 62-65). In a further preferred method of the invention said nucleic acid molecule consists of the nucleic acid sequence which encodes the amino acid sequence Ciz1 in FIG. 16 (SEQ ID NO: 26) or FIG. 17 (SEQ ID NO: 47) or variants thereof, including those described in FIGS. 20A (SEQ ID NO: 58-61) and 20B (SEQ ID NO: 62-65).

In a further preferred method of the invention said polypeptide molecule comprises the amino acid sequence Ciz1 in FIG. 16 (SEQ ID NO: 26) or 17 (SEQ ID NO: 47) or variants thereof, including those described in FIGS. 20A (SEQ ID NO: 58-61) and 20B (SEQ ID NO: 62-65). In a further preferred method of the invention said polypeptide molecule consists of the amino acid sequence Ciz1 in FIG. 16 (SEQ ID NO: 26) or 17 (SEQ ID NO:47) or variants thereof, including those described in FIGS. 20A (SEQ ID NO: 58-61) and 20B (SEQ ID NO: 62-65).

In a further preferred method of the invention said polypeptide is expressed by a cell, preferably a mammalian cell, or animal and said screening method is a cell-based screening method.

Preferably said cell naturally expresses the Ciz1 polypeptide. Alternatively said cell is transfected with a nucleic acid molecule encoding a Ciz1 polypeptide (or a variant molecule thereof, found, for example in cancer cell lineages).

According to a further aspect of the invention there is provided an agent obtainable by the method according to the invention. Preferably said agent is an antagonist of Ciz1 mediated DNA replication. Alternatively said agent is an agonist of Ciz1 mediated DNA replication.

In a further preferred method of the invention said agent is selected from the group consisting of: polypeptide; peptide; aptamer; chemical; antibody; nucleic acid; or polypeptide or nucleotide probe.

Preferably the agent comprises a sequence that is complimentary or of sufficient homology to give specific binding to the target and can be used to detect the level of nucleic acid or protein for diagnostic purposes.

Alternatively the agent identified by the method of the invention is a therapeutic agent and can be used for the treatment of disease.

In one embodiment of the invention the agent is an antibody molecule and binds to any of the sequences represented by FIGS. 16 (SEQ ID NO: 26), 17 (SEQ ID NO: 47) or 20 (SEQ ID NO: 58-65).

Preferably said antibody is a monoclonal antibody.

Alternatively said agent is an anti-sense nucleic acid molecule which binds to and thereby blocks or inactivates the mRNA encoded by any of the nucleic acid sequences described above.

In an alternative embodiment, said agent is an RNAi molecule and comprises two complementary strands of RNA (a sense strand and an antisense strand) annealed to each other to form a double stranded RNA molecule. Preferably the RNAi molecule is derived from the exonic sequence of the Ciz1 gene or from another over-lapping gene.

In one embodiment unspliced mRNA is targeted with RNAi to inhibit production of the spliced variant. In another the spliced variant mRNA is ablated without affecting the non-variant mRNA.

In a preferred method of the invention said peptide is an oligopeptide. Preferably, said oligopeptide is at least 10 amino acids long. Preferably said oligopeptide is at least 20, 30, 40, 50 amino acids in length.

In a further preferred method of the invention said peptide is a modified peptide.

It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, ornithine. Other modifications include amino acids with a $C_2$, $C_3$ or $C_4$ alkyl R group optionally substituted by 1, 2 or 3 substituents selected from halo (eg F, Br, I), hydroxy or $C_1$-$C_4$ alkoxy.

Alternatively said peptide is modified by acetylation and/or amidation.

In a preferred method of the invention the polypeptides or peptides are modified by cyclisation. Cyclisation is known in the art, (see Scott et al Chem Biol (2001), 8:801-815; Gellerman et al J. Peptide Res (2001), 57: 277-291; Dutta et al J. Peptide Res (2000), 8: 398-412; Ngoka and Gross J. Amer Soc Mass Spec (1999), 10:360-363).

According to a further aspect of the invention there is provided a vector as a delivery means for, for example, an antisense or an RNAi molecule which inhibits Ciz1 or variants thereof and thereby allows the targeting of cells expressing the protein to be targeted.

In one embodiment of the invention a viral vector is used as delivery means.

Preferably the vector includes an expression cassette comprising the nucleotide sequence selected from the group consisting of;
  a) the nucleic acid sequence which encodes Ciz1 amino acid sequence as shown in FIGS. 14, 15 and 21 (SEQ ID NO: 45, 46, 66, 67, 68, 69, 70, 71, 72 or 73);
  b) a nucleic acid molecule which hybridizes to the nucleic acid sequence of (a);
  c) a nucleic acid molecule which has a nucleic acid sequence which is degenerate because of the genetic code to the sequences in a) and b) and any sequence which is complimentary to any of the above sequences;

d) a nucleic acid sequence that encodes Ciz1 pre-mRNA (i.e., the genomic sequence), wherein the expression cassette is transcriptionally linked to a promoter sequence.

Preferably the vectors including the expression cassette is adapted for eukaryotic gene expression. Typically said adaptation includes, by example and not by way of limitation, the provision of transcription control sequences (promoter sequences) which mediate cell/tissue specific expression. These promoter sequences may be cell/tissue specific, inducible or constitutive.

Promoter elements typically also include so called TATA box and RNA polymerase initiation selection sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors. Further adaptations which facilitate the expression of vector encoded genes include the provision of transcription termination sequences.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbor Laboratory, Cold Spring Harbor, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

According to the present invention there is provided a diagnostic method for the identification of proliferative disorders comprising detecting the presence or expression of the Ciz1 gene, Ciz1 splice variants and mutations in the genomic or protein sequence thereof.

Preferably said diagnostic method comprises one of more of the following steps:
(i) contacting a sample isolated from a subject to be tested with an agent which specifically binds a polypeptide with Ciz1 activity or a nucleic acid molecule encoding a polypeptide with Ciz1 activity; and
(ii) detecting or measuring the binding of the agent on said polypeptide or nucleic acid in said sample;
(iii) use of reverse-transcribed PCR or real-time PCR to monitor Ciz1 isoform expression and to measure expression levels.
(iv) measuring the presence of nucleic acid or amino-acid mutations based on altered conformational properties of the molecule.

In one embodiment, the diagnostic method of the present invention is carried out in-vivo. In an alternative embodiment, the diagnostic method of the present invention is carried out ex-vivo or in-vitro.

Preferably the diagnostic method provides for a quantitative measure of Ciz1 RNA or protein variants in a sample.

In one embodiment of the invention there is provided the use of an agent which modulates Ciz1 RNA or protein, or variants thereof, as a pharmaceutical.

Preferably said pharmaceutical comprises an agent identified by the screening method of the present invention in combination or association with a pharmaceutically acceptable carrier, excipient or diluent.

Preferably said pharmaceutical is for oral or topical administration or for administration by injection. In alternative embodiment of the invention the pharmaceutical is administered as an aerosol.

In a further preferred embodiment of the invention there is provided the use of an agent according to the invention for the manufacture of a medicament for use in the treatment of proliferative disease. Preferably said proliferative disease is cancer.

Preferably said cancer is a pediatric cancer and is selected from the group consisting of; retinoblastoma, neuroblastoma, Burkitt lymphoma, medulloblastoma, and Ewings Sarcoma family tumors (ESFTs).

In an alternative embodiment the cancer is a carcinoma, adenocarcinoma, lymphoma or leukemia.

In an alternate embodiment the disease is liver, lung or skin cancer or metastasis.

According to a further aspect of the invention there is provided a method to treat a proliferative disease comprising administering to an animal, preferably a human, an agent obtainable by the method according to the invention.

According to an alternate aspect of the invention, there is provided the use of an agent according to the invention for the manufacture of a medicament to slow cell division or growth.

The invention also includes the use of the Ciz1 amino acid sequence and protein structure in rational drug design and the use of Ciz1 nucleotide and amino acid sequences thereof or variants thereof for screening chemical libraries for agents that specifically bind to Ciz1.

The invention also includes a kit comprising a diagnostic, prognostic or therapeutic agent identified by the method of the invention.

In an alternative embodiment of the invention, an array based sequencing chip is used for the detection of altered Ciz1.

BRIEF DESCRIPTION OF THE FIGURES

An embodiment of the invention is described below by example only and with reference to the following figures:

FIG. 1A-1D illustrate the effect of cyclin A-cdk2 on late G1 nuclei. FIG. 1A shows that anti-Cdc6 antibody V1 detects mouse Cdc6 and a second antigen in western blots of 3T3 whole cell extract, which migrates with approximate Mr of 100 kDa (based on the mobility of the Mcm3 protein this was previously estimated at nearer 85 kDa so the antigen was named p85—we have kept the same name here for clarity). P85 is present in both the soluble fraction and insoluble nuclear fraction (prepared under in vitro replication conditions). FIG. 1B shows initiation of DNA synthesis in 'replication competent' late G1 phase nuclei by G1 phase extract supplemented with recombinant cyclin A-cdk2. Control bar shows the proportion of nuclei already in S phase (unshaded), and those that initiated replication in extract from S phase cells (shaded). FIG. 1C shows that after 15 minutes under cell-free replication conditions nuclei were washed and the chromatin fraction was re-isolated and separated by SDS-Page and blotted for Mcm2 and Mcm3. FIG. 1D shows the same nuclei blotted with antibody V1. p85 antigen is more abundant in nuclei exposed to initiation-inducing concentrations of cyclin A-cdk2. Antibody V1 was used to clone the gene for p85 from a mouse embryo expression library which was identified as Ciz1.

FIG. 2C shows sequence features and putative domains in ECiz1. Predicted nuclear localization sequence (NLS), putative cyclin-dependent kinase phosphorylation sites, C2H2 type zinc-fingers and a C terminal domain with homology to the nuclear matrix protein matrin 3 (Nakayasu and Berezney, 1991) are shown. The positions of sequences absent from ECiz1 are indicated by triangles. FIG. 2D shows ECiz1 and derived truncations and point mutants used in cell-free DNA replication experiments. Numbers in parentheses relate to amino-acid positions in the full-length form of mouse Ciz1, shown in FIG. 2A. Stars indicate putative phosphorylation sites ablated by site-directed mutagenesis.

FIG. 3A shows that recombinant ECiz1 stimulates initiation of DNA replication in 'replication competent' late G1 phase nuclei, during incubation in S phase extract. Histogram shows the average number of nuclei that incorporated biotinylated nucleotides in vitro (black), in the presence or absence of ectopic ECiz1, with standard deviations calculated from four independent experiments. The 17% of nuclei that were already in S phase when the nuclear preparation was made are shown in white. Images show nuclei replicating in vitro, with or without 1 nM ECiz1. Total nuclei are counterstained with propidium iodide (red). FIG. 3B shows that the response to recombinant ECiz1 is concentration dependent with a sharp optimum in the nM range. In this experiment, and all those shown in FIG. 3B-3I, results are expressed as % initiation rather than % replication. This is calculated from the number of nuclei that initiate in vitro and the number of nuclei that are 'competent' to initiate in vitro (see methods). FIG. 3C shows that threonines 191/2 are involved in regulating Ciz1 DNA replication activity as ECiz1 cdk site mutant T(191/2)A escapes suppression at high concentrations. FIG. 3D shows that Cdk site mutant T(293)A stimulates initiation with a similar profile to ECiz1 but at lower concentrations. FIG. 3E shows that truncated ECiz1 (Nterm 442) lacks C-terminal sequences, but stimulates in vitro initiation to a similar extent as ECiz1. FIG. 3F shows that Cterm 274 retains no DNA replication activity in this assay. FIGS. 3G, 3H, and 3I show that in further deletion analysis in the N-terminal two thirds of the ECiz1 protein, a short region 3' of exon 8 is required for Ciz1 function when assayed in vitro.

FIG. 4A-4C show characterization of anti-Ciz1 polyclonal antibodies and identification of 125 kDa Ciz1-related bands. FIG. 4A shows a Coomassie stained SDS-polyacrylamide gel showing purified recombinant ECiz1 fragment Nterm442, and western blots of recombinant Nterm442 using anti-Cdc6 antibody V1, and anti-Ciz1 antibodies 1793 and 1794. FIG. 4B shows Western blots of 3T3 whole cell extract. Of the two bands detected by anti-Ciz1 antibody 1793 one has the same mobility as p85-Ciz1 (100 kDa) recognized by antibody V1 and the other has an apparent Mr of 125 kDa. Anti-Ciz1 antibody 1794 recognizes only the 125 kDa form of Ciz1 (and a second antigen of around 80 kDa). FIG. 4C shows immuno-precipitation from 3T3 nuclear extract, using antibody V1 or anti-Ciz1 1793. Both antibodies precipitate p85, which is recognized by the reciprocal antibody in western blots. P125 is precipitated by antibody 1793, and to a lesser extent by antibody V1 and these are recognized by 1793 in western blots. Mcm3 is shown as a control.

FIG. 5A shows endogenous Ciz1 (red) in 3T3 cells fixed before (untreated) or after (detergent treated) exposure to TritonX100, detected with anti-Ciz1 antibody 1793. Nuclei are counterstained with Hoescht 33258 (blue). Cdc6 (green), detected with a Cdc6-specific monoclonal antibody is shown for comparison. FIG. 5B shows that inclusion of recombinant Ciz1 blocks reactivity of antibody 1793 with detergent treated nuclei. FIG. 5C shows that detergent-resistant Ciz1 (red) is present in all nuclei in cycling populations, while detergent-resistant PCNA (green) persists only in S phase nuclei. FIG. 5D shows high-magnification confocal sections of detergent-resistant Ciz1 and PCNA, and merged image showing co-localizing foci (yellow). FIG. 5E shows lined plots of red and green fluorescence across the merged image in FIG. 5D, at the positions indicated (i and ii). FIG. 5F shows a cross-correlation plot (Rubbi and Milner, 2000; van Steensel et al., 1996) for green foci compared to red over the whole merged image in FIG. 5D, and (inset) for the marked section after thresh-holding fluorescence at the levels shown in Eii. The red line in the inset to FIG. 5F shows loss of correlation when the Ciz1 image is rotated 90° with respect to PCNA. Bar is 10 µM.

FIG. 6A shows siRNAs that target Ciz1 transcripts at four sites (see FIG. 2A) were individually applied to cycling 3T3 cells as a single 3 nM dose and cell number was monitored at the indicated times. Images of cell populations at 16 and 40 hours after transfection with siRNA 8 (red outline) or mock treated cells (blue outline) are shown. FIG. 6B shows Ciz1 protein detected with anti-Ciz1 1793 (green) 48 hours after exposure to Ciz1 siRNAs (4 and 8), or control GAPDH siRNA. FIG. 6C shows Ciz1, GAPDH and β-actin transcript levels in cells exposed to Ciz1 siRNAs (4 and 8), or control GAPDH siRNA for 24 hours. Numbers in parentheses reflect band intensity in arbitrary units, and the overall reduction in Ciz1 and GAPDH transcripts (normalized against β-actin) is expressed as a percentage. FIG. 6D shows that the proportion of cells that incorporated BrdU into DNA (green) is significantly decreased in Ciz1 depleted cells, 48 hours after treatment with Ciz1 siRNA. Histogram shows average results from four independent experiments. FIG. 6E shows that the number of nuclei with detergent-resistant Mcm3 (green) increases in populations treated with Ciz1 siRNA. FIG. 6F shows that the proportion of nuclei with detergent-resistant PCNA (green) also increases under these conditions. All nuclei are counterstained and shown in pseudo-color (red).

FIG. 8C shows high-magnification images of live 3T3 cell nuclei 24 hours after transfection showing the subnuclear organization of EGFP tagged Ciz1 and ECiz1 and derived fragments with the C-terminal fragment (equivalent to Cterm274) removed. In the absence of C-terminal domains GFP-ECiz1 is diffusely localized in the nucleus 24 hours after transfection, while GFP-Ciz1 aggregates to form one or two large blobs within the nucleus. FIG. 8D shows that the C terminal 274 domain alone is cytoplasmic until after cells have passed through mitosis (most likely due to lack of nuclear localization sequences and passive entry to the nucleus), but once inside binds to nuclear structures and condenses with chromosomes. FIG. 8E shows representative images of GFP-Ciz1 (green), BrdU (red) and total nuclei (blue) in a population labelled with BrdU for the first 12 hours after transfection. Histograms show the proportion of transfected (green) cells that incorporated BrdU compared to the number of untransfected (grey) cells for three separate labelling windows. During 0-22 hours after transfection rapidly cycling cells registered a consistent increase in the BrdU labelled fraction when transfected with either Ciz1 or ECiz1. Similar results were obtained with dense cultures in which most cells had exited the cell cycle and entered quiescence. However, when rapidly cycling cells were exposed to BrdU for a short (20 minute) pulse 22 hours after transfection the number of cells engaged in DNA synthesis was reduced in the Ciz1 and ECiz1 transfected populations, compared to untransfected controls and cells transfected with GFP alone. This indicates that by 22 hours DNA synthesis had ceased in Ciz1 expressing cells.

FIG. 11A shows translated ESTs from pediatric cancers and adult neural cancers.

FIG. 11B shows translated ESTs from various non-cancer cells and tissues.

FIG. 11C shows translated ESTs from leukemias, lymphomas, and from normal haematopoetic and lymphocytic cells.

FIG. 11D shows translated ESTs from carcinomas.

FIG. 11E shows translated ESTs from a range of other cancers.

FIG. 11F shows a summary of alternatively spliced regions (SEQ ID NO: 37-44) in human Ciz1 showing conditionally included sequences.

FIGS. 12A and 12B show Ciz1 splice variant expression in Ewings sarcoma family tumor cell lines (ESFT) and neuroblastoma cell lines. FIG. 12A shows whole RNA samples from six independent ESFT cell lines, two neuroblastomas and a control cell line (HEK293 cells), subject to RT-PCR analysis using 4 different primer sets. ESFT cell lines are 1) A673, 2) RDES, 3) SKES1, 4) SKNMC, 5) TC3, 6) TTC466. Neuroblastoma cell lines are 1) IMR32, 2) SKNSH. FIG. 12B shows analysis of Ciz1 Exons 3/4/5 PCR products in ESFTs and neuroblastoma. The products of primers h3 and h4 (spanning potentially variable exons 4 and 6) were analyzed in more detail. PCR fragments were purified from agarose gels by standard procedures, subcloned and sequenced to identify the source of fragment size variations. Between one and eleven individual clones for each of the seven cell lines were sequenced and the results are summarized in tabular form. Ciz1 from ESFT cell lines lacks exon 4 in 31% of transcripts overall, and for some ESFT lines this is nearer 50%. DSSSQ (SEQ ID NO:1) is more commonly absent in the two neuroblastoma cell lines tested here.

FIG. 13A shows that both prostate cancer cell lines contain an excess of the largest p125 Ciz1 protein variant in the nuclear fraction, compared to the non-cancer cell line. FIG. 13B shows models for the production of p85 (100) from p125 variants by protein processing during initiation of DNA replication.

FIG. 14 illustrates the full length mouse mRNA sequence (SEQ ID NO: 45).

Figure 15:
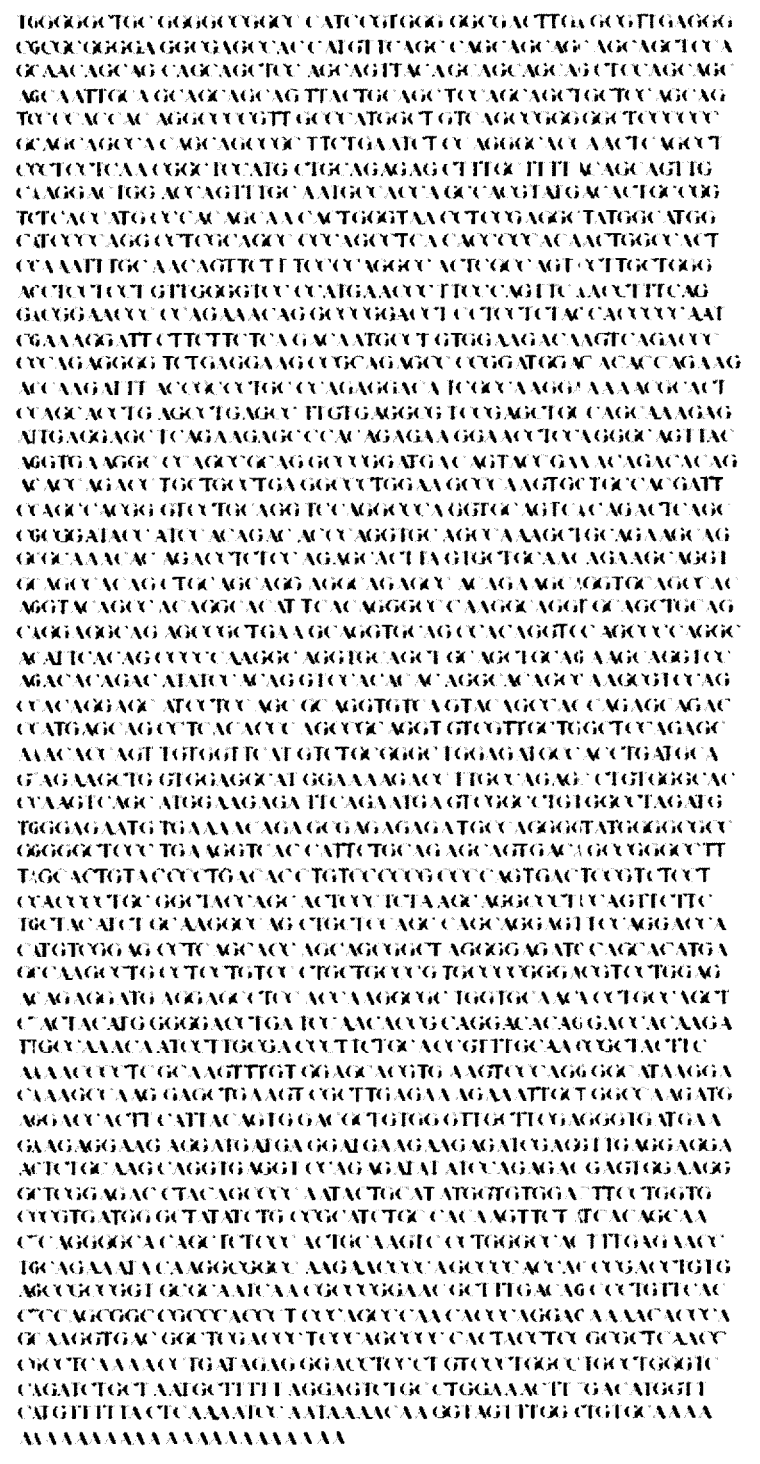

FIG. 15 illustrates the full length human mRNA sequence (SEQ ID NO: 46).

FIG. 16 illustrates the full length mouse protein sequence (SEQ ID NO: 26).

FIG. 17 illustrates the full length human protein sequence (SEQ ID NO: 47).

FIG. 18 illustrates human alternatively spliced protein sequences (SEQ ID NO: 48, 74, 41, 1, 43, 42, 44, 3 and 40, respectively). Sequences shown are absent in the spliced protein sequences.

FIG. 19 illustrates human alternatively spliced mRNA sequences (SEQ ID NO: 49-57, respectively). Sequences shown are absent in the spliced protein sequences.

FIGS. 20A and 20B illustrate unique junction sequences created in human Ciz1 proteins by missing exons (SEQ ID NO: 58-61 and 62-65, respectively). Junction sequences represent prime sites of target for therapeutic agents identified by the method of the invention.

Figure 21A:
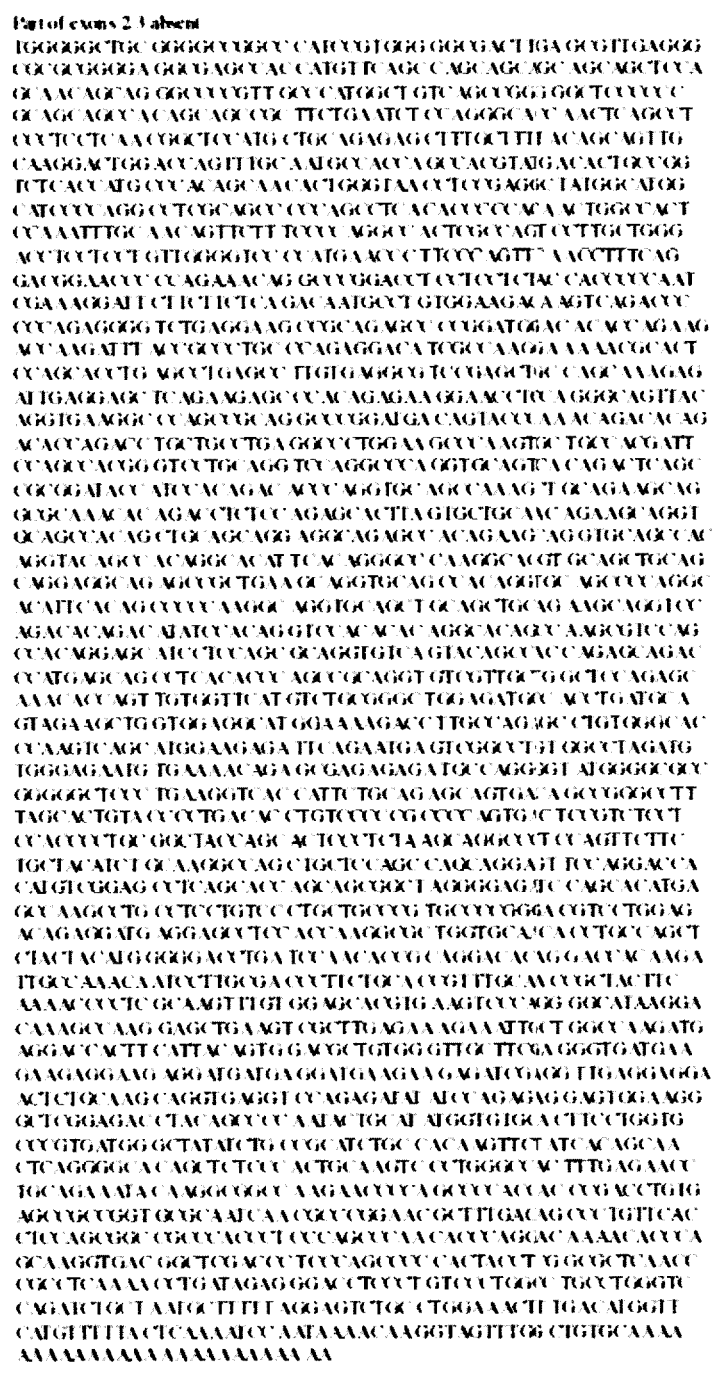

FIG. 21A-21H illustrate junction sequences created in human Ciz1 mRNA (SEQ ID NO: 66-73, respectively).

DETAILED DESCRIPTION

Identification of Ciz1

We have exploited a polyclonal antibody (antibody V1) that was raised against recombinant human Cdc6 (Coverley et al., 2000; Stoeber et al., 1998; Williams et al., 1998) to identify and study an unknown antigen whose behavior correlates with initiation of DNA replication in vitro. The antigen has an apparent Mr of 100 kDa (called p85) and is readily detectable in extracts from 3T3 cells (FIG. 1A).

DNA synthesis can be activated in cell-free replication experiments using 'replication competent' late G1 phase nuclei, G1 extracts, and recombinant cyclin A-cdk2. Under these conditions nuclei will incorporate labelled nucleotides into nascent DNA, in a manner strictly dependent on the concentration of active protein kinase (FIG. 1B). Above and below the optimum concentration no initiation of DNA replication takes place. However, other events occur which inversely correlate with initiation (Coverley et al., 2002). Here we use activation of DNA synthesis (FIG. 1B), and Mcm2 phosphorylation (which results in increased mobility, FIG. 1C), to calibrate the effects of recombinant cyclin A-cdk2 in cell-free replication experiments, and correlate the behavior of p85 with activation of DNA synthesis.

In G1 nuclei that are re-isolated from reactions containing initiation-inducing concentrations of cyclin A-cdk2, p85 antigen is more prevalent compared to nuclei exposed to lower or higher concentrations of kinase (FIG. 1D). This suggests that p85 is regulated at some level by cyclin A-cdk2, in a manner that is co-incident with activation of DNA synthesis. No other antigens correlate so closely with this stage in the cell-free initiation process, therefore we used antibody V1 to clone the gene for mouse p85.

When applied to a cDNA expression library derived from 11-day mouse embryos antibody V1 picked out two clones that survived multiple rounds of screening (see methods). One encoded mouse Cdc6, while the other encoded 716 amino acids of the murine homologue of human Ciz1 (Mitsui et al., 1999). Full-length human and mouse Ciz1 have approximately 70% overall homology at the amino-acid level, with greatest (>80%) homology in the N and C terminal regions. Ciz1 is conserved among vertebrates as homologues exist in rat and fugu, but no proteins with a high degree of homology or similar domain structure could be identified in lower eukaryotes, raising the possibility that Ciz1 evolved to perform a specialized role in vertebrate development.

A previous publication on human Ciz1 (Mitsui et al 1999) demonstrated interaction with the cell-cycle protein p21-CIP1, leading to investigation of a proposed role as a transcription factor, not a DNA replication factor. A second paper (Warder and Keherly 2003) published after the priority date of this patent application suggests a role for Ciz1 in tumorigenesis, but does not demonstrate a role in DNA replication or recognize the importance of Ciz1 splice variant expression.

Multiple Ciz1 Isoforms

Figure 2A:
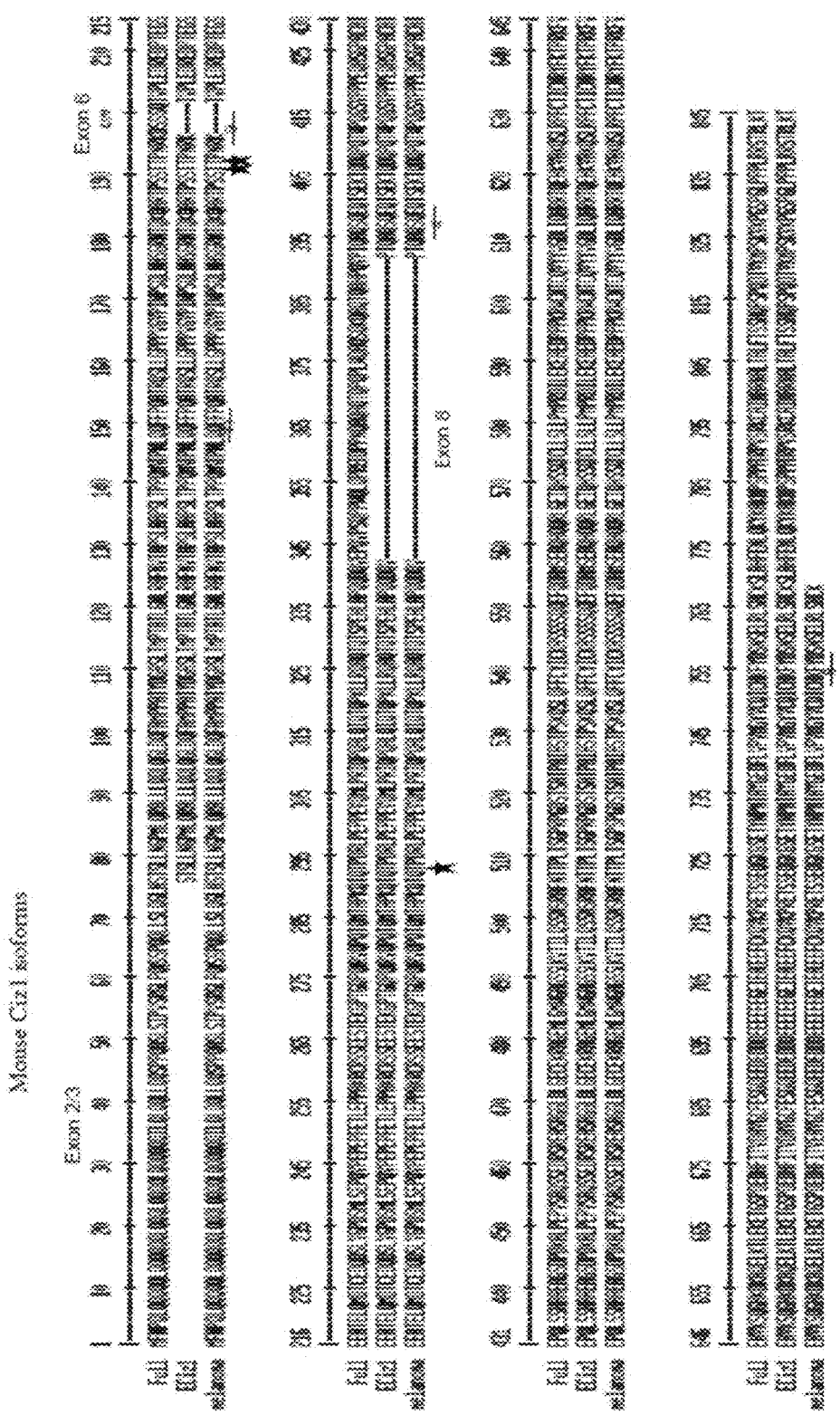
FIG. 2A shows an alignment of mouse Ciz1 variants. The predicted full-length Ciz1 amino-acid sequence ('Full'; SEQ ID NO: 26) is identical to a mouse mammary tumor cDNA clone (BC018483), while embryonic Ciz1 ('ECiz1', AJ575057; SEQ ID NO: 27), and a melanoma-derived clone (AK089986; SEQ ID NO: 28) lack two discrete internal sequences. In addition, the first available methionine in ECiz1 is in the middle of exon 3 (Met84), which excludes a polyglutamine rich region from the N-terminus. Melanoma derived AK089986 may be incomplete as it ends 77 codons before the C-terminus of all other mouse and human clones. Stars indicate amino-acids changed by site-directed mutagenesis in the constructs shown in FIG. 2D. Amino-acids that correspond to codons targeted by siRNAs are underlined.
Figure 2B:
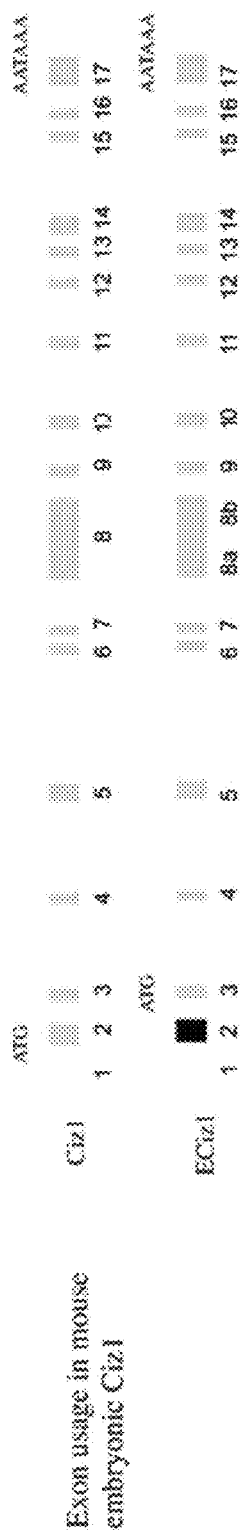
FIG. 2B shows that mouse Ciz1 is encoded by at least 17 exons. Coding exons are shown in grey, alternatively spliced regions are black, untranslated regions are white. Two alternative exon 1 sequences are included in some Ciz1 transcripts (not shown) but an alternative translational start site upstream of the two depicted here has not yet been found.
Figure 7:
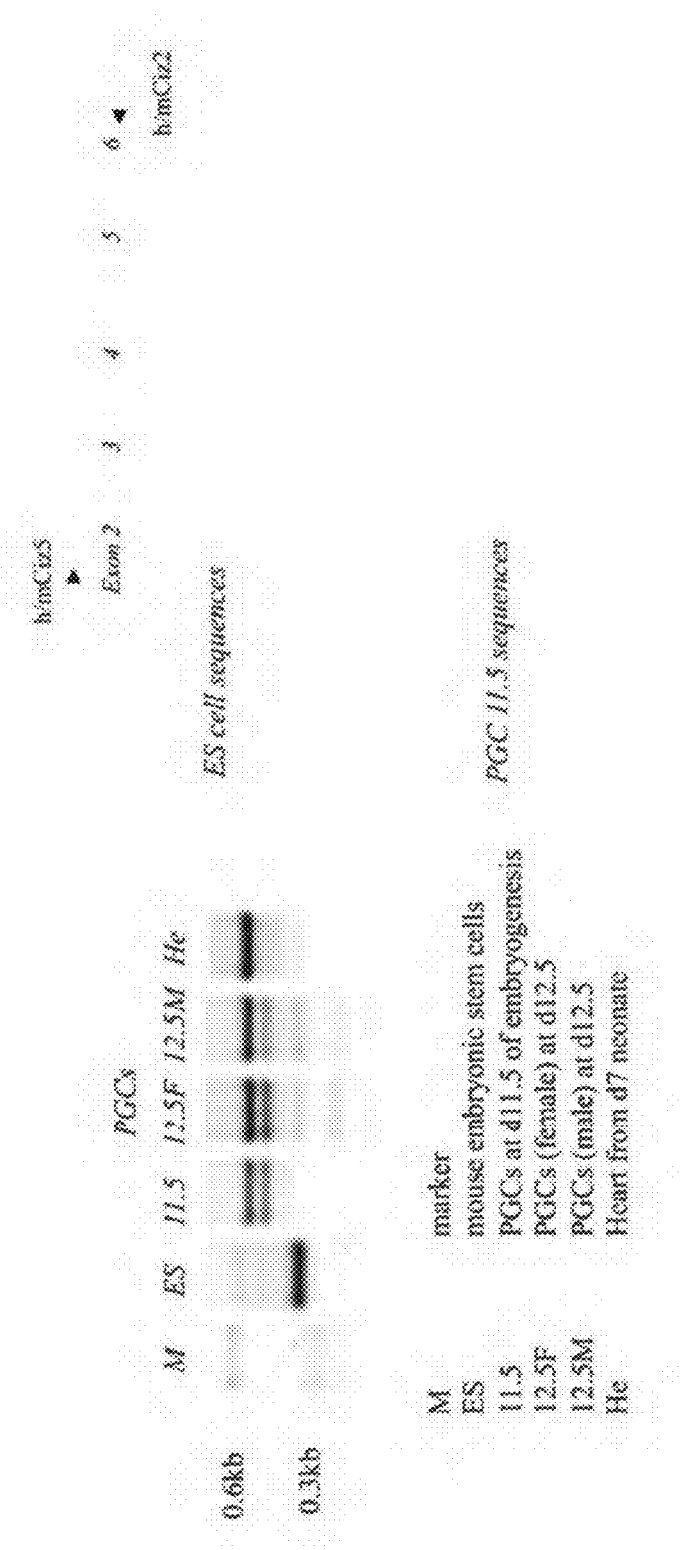
FIG. 7 shows RT-PCR analysis of Ciz1 exons 3/4 splice variant expression in mouse primordial germ cells and embryonic stem cells. Exons 3 and/or 4 are alternatively spliced in these cell types, but not in neonatal heart. These data are consistent with the hypothesis that full-length Ciz1 is the pre-dominant form in neonatal somatic tissue, and that variants occur with more frequency earlier in development, and in germ line tissues.

The predicted mouse Ciz1 open reading frame and a cDNA derived from a mouse mammary tumor library (BC018483) contain three regions that are not present in our embryonic clone (AJ575057), hereafter referred to as ECiz1 (FIG. 2A; SEQ ID NO: 27). The three variable regions in ECiz1 appear to be the result of alternative splicing of exons 2/3, 6 and 8 (FIG. 2B). Mouse melanoma clone AK089986 lacks two of the same three regions as ECiz1 (FIG. 2A), while the third encodes an N-terminal polyglutamine stretch that is also absent from human medulloblastoma derived clones. A fourth sequence block derived from exons 3/4 is absent from Ciz1 transcripts derived from mouse ES cells, and from exon 4 in mouse primordial germ cells (FIG. 7). Human Ciz1 is also alternatively spliced at the RNA level to yield transcripts that exclude combinations of the same four sequence blocks as mouse Ciz1 (see below). In fact, all known variations in mouse Ciz1 cDNAs have close human parallels, some of which are identical at the amino-acid level. This suggests that the different Ciz1 isoforms have functional significance. A fifth variable region (not yet observed in the mouse) is alternatively spliced in human Ciz1 transcripts derived mainly from carcinomas.

The data suggest that shorter forms of Ciz1 (lacking the alternatively spliced exons) are most prevalent early in development and in cell lineages that give rise to the germ line. In the analysis shown in FIG. 7, only Ciz1 from fully developed neonatal heart shows no alternative splicing, while all embryonic cell types contain alternatively spliced forms. Furthermore, the only complete Ciz1 cDNAs in public databases (human or mouse) are derived from non-embryonic cell types, and the only ones derived from embryonic sources are alternatively spliced. Therefore, Ciz1 splice variant expression appears to occur preferentially in cell types that are not yet fully differentiated.

Notably, Ciz1 cDNAs from pediatric cancers are also alternatively spliced (see below). This lead us to the hypothesis that failure to express the appropriate Ciz1 isoform at the right point in development leads to inappropriately regulated Ciz1 activity. This could contribute to unscheduled proliferation and cellular transformation.

ECiz1 Stimulates DNA Replication In Vitro

Figure 3A:
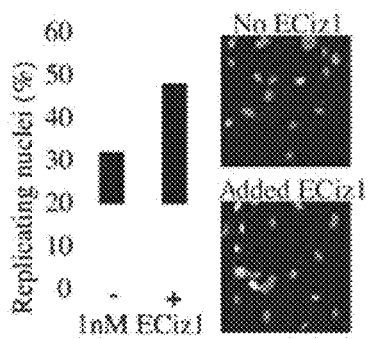
FIG. 3A-3I show the effect of Ciz1 protein and derived fragments in cell-free DNA replication experiments and illustrate that ECiz1 promotes initiation of mammalian DNA replication.

Upon exposure to cytosolic extract from S phase cells, late G1 phase nuclei initiate DNA replication and begin synthesizing nascent DNA (Krude et al., 1997). We used this cell-free assay to test the effect of ECiz1, and derived recombinant fragments, on DNA synthesis (FIG. 3). Full-length ECiz1 protein consistently increased the number of nuclei that replicated in vitro, from 30% (+/−0.9%) to 46% (+/−5.5%), which suggests that Ciz1 is limiting for initiation in S phase extracts (FIG. 3A). Only two other classes of protein (cyclin-dependent kinases, Coverley et al., 2002; Krude et al., 1997; Laman et al., 2001, and the Cdc6 protein, Coverley et al., 2002; Stoeber et al., 1998) have been previously found to stimulate cell-free initiation. Thus, ECiz1 is the first protein to have this property that was not already known to be involved in the replication process. The positive effect of recombinant ECiz1 on cell-free initiation argues that endogenous Ciz1 plays a positive role in DNA replication in mammalian cells.

Figure 3B:
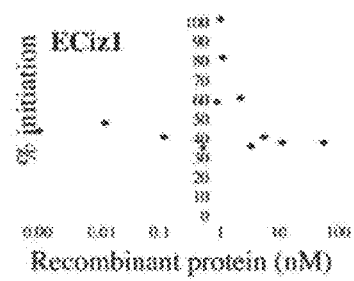

Stimulation of cell-free initiation is concentration-dependent with peak activity in S phase extract at around 1 nM ECiz1 (FIG. 3B). This echoes previous cell-free analyses with other recombinant proteins (Coverley et al., 2002; Krude et al., 1997), where stimulation of initiation typically peaks and then falls back to the un-stimulated level at high concentrations. For ECiz1, the reason for the drop in activity at high concentrations is not yet clear. However, mutagenesis studies (see below) suggest that the restraining mechanism is likely to be active and specific rather than due to a general imbalance in the composition of higher order protein complexes.

Figure 3C:
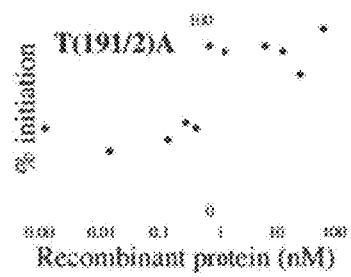
Figure 3D:
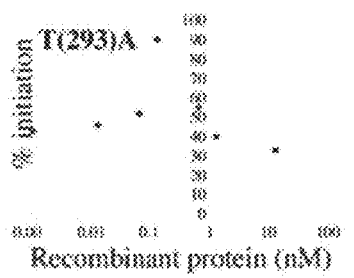

Down regulation of ECiz1 involves threonines 191/192 Ciz1 is likely to be a phospho-protein in vivo since it contains numerous putative phosphorylation sites, and it displays altered mobility when 3T3 cell extracts are treated with lambda phosphatase (not shown). Murine Ciz1 contains two RXL cyclin binding motifs and five putative cdk-phosphorylation sites, which are present in all known variants. Four of these are located in the N-terminal fragment of ECiz1 that contains in vitro replication activity (see below), and one is adjacent to the site at which exon 6 is alternatively spliced to exclude a short DSSSQ (SEQ ID NO: 1) sequence motif (FIG. 2A, C). As this motif is 100% identical and alternatively spliced in both mouse and man we reasoned that conditional inclusion might serve to regulate Ciz1 activity, identifying this region of the protein as potentially important. We therefore chose to focus on the cdk site that is four residues upstream and which is also conserved in mouse and man, by combining a genetic approach with cell-free replication assays. Starting with ECiz1, two threonines at 191 and 192 were changed to two alanines, generating ECiz1T(191/2)A (FIG. 2D). When tested in vitro for DNA replication activity, ECiz1 T(191/2)A stimulated initiation in late G1 nuclei to a similar extent as ECiz1 (FIG. 3C). However unlike ECiz1, stimulation of initiation was maintained over a broad range of concentrations that extended over at least three orders of magnitude. Therefore, a mechanism to restrict the activity of excess ECiz1 exists and operates in a cell-free environment. In a separate construct, the threonine at position 293 was also changed to alanine generating ECiz1 T(293)A (FIG. 2D), but this alteration had little effect on ECiz1 activity assayed in vitro (FIG. 3D).

These results demonstrate that down-regulation of ECiz1 activity involves threonine 191/2, and is probably caused by cyclin-dependent kinase mediated phosphorylation at this site. This links Ciz1 activity to the cdk-dependent pathways that control all major cell-cycle events, including initiation of DNA replication.

Most pre-replication complex proteins and many replication fork proteins are phosphorylated in vivo, often by cyclin-dependent kinases (Bell and Dutta, 2002; Fujita, 1999). Our data suggests that nuclear accumulation of p85-Ciz1 antigen is regulated (directly or indirectly) by cyclin A-cdk2, and it shows that a specific consensus cdk phosphorylation site at threonine 191/192 is involved in controlling Ciz1 activity. When this site is made unphosphorylatable Ciz1 activity is maintained over a broader range of concentrations in cell-free assays. Therefore, Ciz1 activity is normally down regulated by modification at this site. The functions of the other conserved cdk phosphorylation sites, and the effect of conditional inclusion of an RXL cyclin-binding motif in the alternatively spliced N-terminal portion of Ciz1, remain to be determined. Thus, the simple negative relationship between Ciz1 activity and cdk-dependent phosphorylation that has been uncovered here, is unlikely to be the whole story. However, our analysis so far links Ciz1 with the cdk-dependent pathways that control all major cell-cycle transitions, and is therefore consistent with our main conclusion that Ciz1 is involved in initiation of DNA replication.

In Vitro Replication Activity Resides in the N-Terminus

Figure 3E:
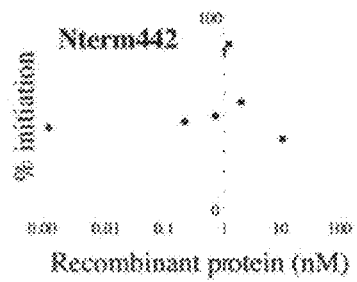
Figure 3F:
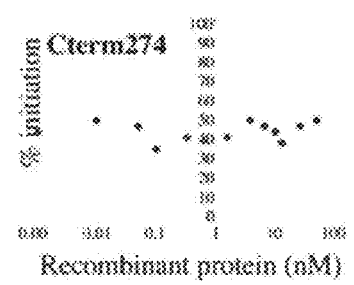
Figure 3G:
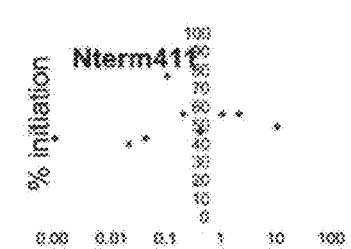
Figure 3H:
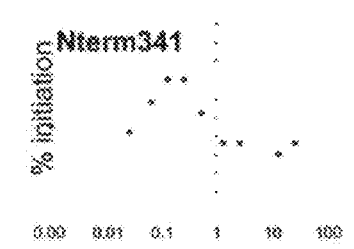
Figure 3I:
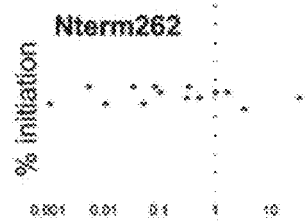

Ciz1 possesses several C-terminal features that may anchor the protein within the nucleus. The matrin 3 domain suggests interaction with the nuclear matrix and the three zinc-fingers imply interaction with nucleic acids. Indeed, recent evidence suggests that human Ciz1 binds DNA in a weakly sequence specific manner (Warder and Keherley, 2003). To determine whether C-terminal domains are important for ECiz1 replication activity we divided the protein into two fragments (FIG. 2D). Nterm442 (which contains the NLS, two conserved cdk sites, one zinc finger and all known sites where variable splicing has been observed) stimulates initiation to a similar extent and at the same concentration as ECiz1 (FIG. 3E). In contrast, the C-terminal portion (Cterm274) contains no residual replication activity (FIG. 3F). Therefore, the matrin 3 domain, one of the cyclin-dependent kinase phosphorylation sites and two of the zinc-fingers are not required for the DNA replication activity of ECiz1, when assayed in vitro. It should be noted however that this analysis measures ECiz1 activity in trans under conditions where the consequences of mis-localisation are unlikely to be detected. Therefore, it remains possible that the matrin 3 domain and zinc fingers act in vivo to direct Ciz1 activity to specific sites in the nucleus and thus limit the scope of Ciz1 activity.

Endogenous Ciz1 antibody V1 recognizes Cdc6 as well as p85-Ciz1 (FIG. 1A), so it is not suitable for immunofluorescence experiments aimed at visualizing the sub-cellular localization of endogenous Ciz1. We therefore generated two new rabbit polyclonal anti-sera against recombinant ECiz1 fragment Nterm442, designated anti-Ciz1 1793 and 1794. As expected, purified Nterm442 is recognized by anti-Ciz1 antibodies 1793 and 1794 in western blots, but it is also recognized by antibody V1 (FIG. 4A), supporting the conclusion that p85(p100) is indeed Ciz1.

When applied to protein extracts derived from growing 3T3 cells, anti-Ciz1 1793 recognized two antigens, with Mr of 125 and 100 kDa (FIG. 4B), whose relative proportions vary from preparation to preparation. The 100 kDa band co-migrates with the cyclin-A responsive antigen that is recognized by antibody V1 (FIGS. 1 and 4B), which suggests that both antibodies recognize the same protein in vivo. We confirmed that the p100-Ciz1 bands recognized by antibody V1 and 1793 are the same protein by immuno-precipitation (FIG. 4C). Antibody V1 precipitated a 100 kDa band that was recognized in western blots by 1793, and vice versa. Furthermore, in the same experiment 1793, and to a lesser extent antibody V1, precipitated a 125 kDa antigen, that was recognized in western blots by 1793. Taken together our observations show that the 100 kDa band is indeed Ciz1 (previously known as p85), and they suggest that Ciz1 protein exists in at least two forms in cycling cells.

In addition to the immuno-precipitation evidence described above, several other observations lead to the conclusion that p125 is also a form of Ciz1. First, both of our anti-Ciz1 antibodies (1793 and 1794) have this band in common. Both antibodies produce the same pattern of nuclear staining in immuno-fluorescence experiments, and this is disrupted in cells treated with Ciz1 siRNA (see below). Second, the relative proportions of p100 and p125 vary from preparation to preparation, and could therefore be the result of proteolytic cleavage. Thirdly, our results are strikingly similar to those of Mitsui et al (1999) whose anti-human Ciz1 monoclonal antibody detected two antigens with apparent Mr of 120 and 95 kDa in HEK293 cells. They proposed that the 120 kDa form of human Ciz1 protein is processed to produce the 95 kDa form and our results are consistent with this proposal.

The 125 kDa band recognized by antibody 1793 in mouse and human cells resolves into three Ciz1-related bands during high-resolution electrophoresis of material derived from non-transformed human cells (Wi38-see later), and mouse cells (NIH3T3—not shown). This may be the result of post-translational modification of the Ciz1 protein or of alternative splicing of the Ciz1 transcript.

Sub-cellular distribution of Ciz1 Anti-Ciz1 1793 was used to visualize the sub-cellular distribution of Ciz1 protein (p85 and p125) in 3T3 cells (FIG. 5A), and in HeLa cells (not shown). In both cell types 1793 reacted with a nuclear-specific antigen, and this was blocked by inclusion of recombinant Nterm442 fragment (FIG. 5B). Unlike Cdc6, which is shown for comparison (FIG. 5A), Ciz1 is clearly detectable in all 3T3 cells in this cycling population. Therefore Ciz1 is present in the nucleus throughout interphase, although minor variations in quantity, or isoform would not be detected by this method. After detergent treatment overall nuclear Ciz1 staining was reduced in all nuclei, which suggests that Ciz1 is present in the nucleus as both a soluble fraction and also bound to insoluble nuclear structures.

Figure 5A:
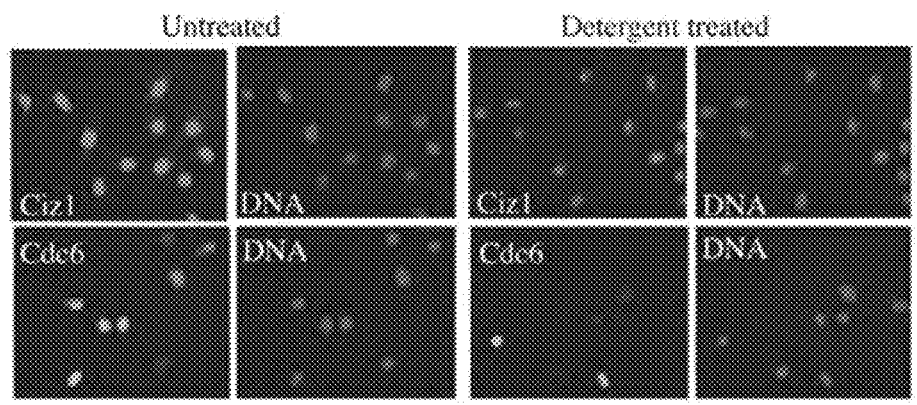
FIG. 5A-5F show immunofluorescence analysis of endogenous Ciz1. Ciz1 resides in sub-nuclear foci that overlap with sites of DNA replication.
Figure 5B:
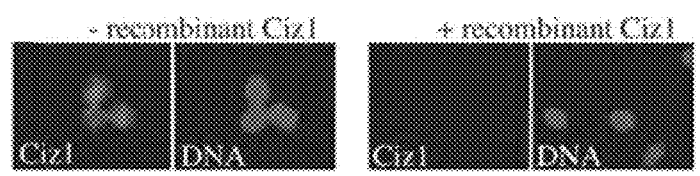
Figure 5C:
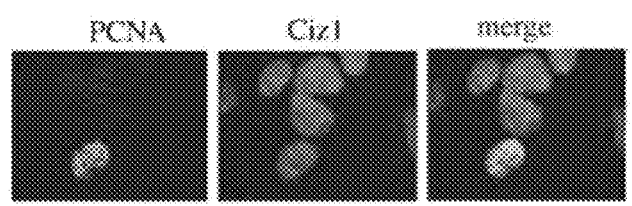
Figure 5D:
Figure 5E:
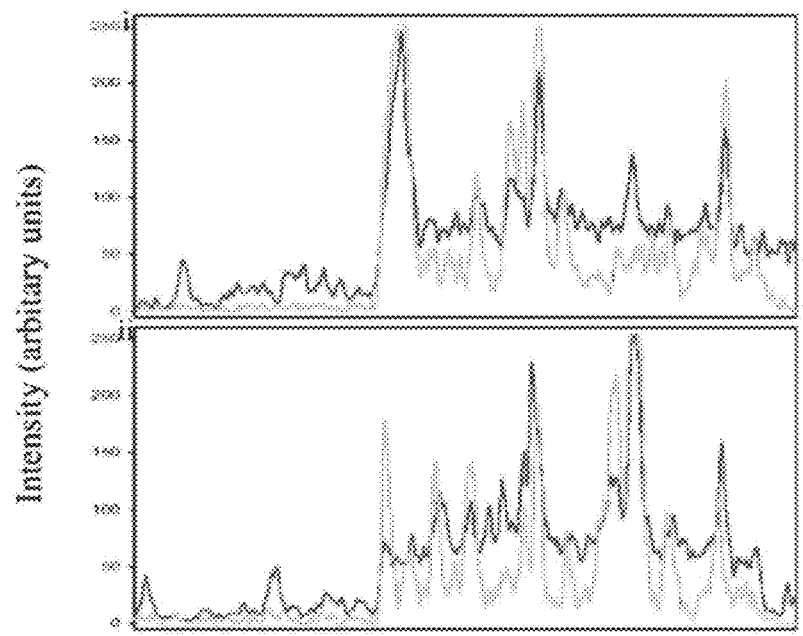
Figure 5F:
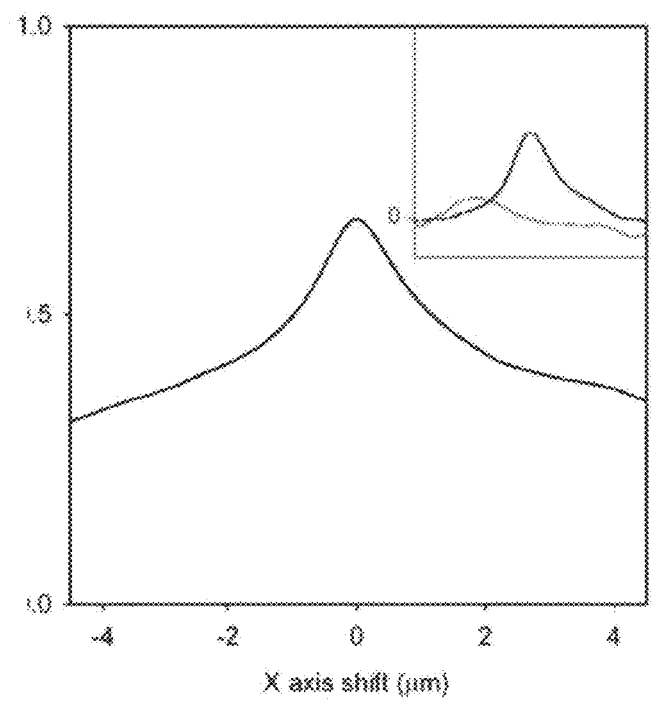

When soluble protein is washed away, the insoluble, immobilized antigen resolves into a punctate sub-nuclear speckled pattern at high magnification (FIG. 5C, D). Ciz1 speckles show a similar size range and distribution as replication 'foci' or 'factories', the sites at which DNA synthesis takes place in S phase. To ask whether Ciz1 is coincident with sites of replication factories, we compared the position of Ciz1 speckles to the position of PCNA, a component of replication complexes in S phase cells (FIG. 5C). In confocal section, PCNA foci are less abundant than Ciz1 foci, but they are almost all co-incident with Ciz1 (FIG. 5D, E, F). This is particularly striking for foci in the medium size range. In merged images, overlap between the positions of PCNA and Ciz1 foci results in yellow spots, while the remaining Ciz1 foci that are not co-incident with PCNA are red. Green (PCNA alone) foci are virtually absent, which suggests that Ciz1 is present at all sites where DNA replication factories have formed.

Ciz1 is also present at sites that don't contain PCNA (FIG. 5D), and unlike PCNA, Ciz1 foci persist throughout interphase (FIG. 5A). One interpretation of these observations is that Ciz1 marks the positions in the nucleus at which PCNA-containing replication factories are able to form in S phase, but that not all of these sites are used at the same time. It remains to be determined whether different Ciz1 foci become active sites of DNA replication at different times in S phase, or whether other nuclear activities also occur at sites where Ciz1 is bound. Indeed, at this stage it also remains possible that the 100 kDa form and the 125 kDa variants of Ciz1 have different activities, and that they reside at nuclear sites with different functions.

Ciz1 is Essential for Cell Proliferation

Figure 6A:
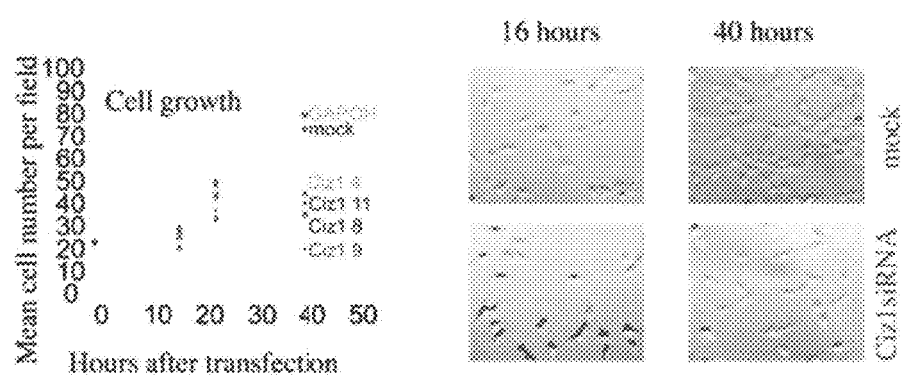
FIG. 6A-6F show RNA interference results. Ciz1 depletion inhibits S phase.
Figure 6B:
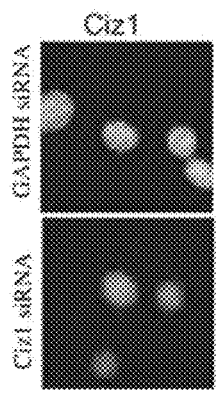
Figure 6C:
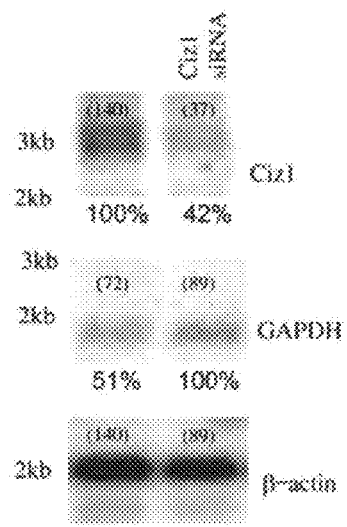

So far we have shown that the behavior of p85 (p100)-Ciz1 correlates with initiation of DNA replication in cell-free assays, that recombinant Ciz1 stimulates the frequency of initiation, and that Ciz1 resides at the same nuclear sites as the DNA replication machinery. However, these data do not show that Ciz1 has an essential function in proliferating cells. In order to test this we used RNA interference (RNAi) to selectively reduce Ciz1 transcript levels in NIH3T3 cells. Four target sequences within Ciz1 were chosen (see FIG. 2A) and short interfering (si) RNA molecules were produced in vitro. When applied to cells, all four Ciz1 siRNA's restricted growth (FIG. 6A) and caused a visible reduction in the level of Ciz1 protein after 48 hours (FIG. 6B). The effect of Ciz1 depletion on proliferation becomes apparent between 23 and 40 hours post-transfection, which suggests that the first cell cycle without Ciz1 RNA is relatively unaffected. By 40 hours, controls and Ciz1 siRNA treated cells diverged significantly with no further proliferation in the Ciz1 depleted population. To verify the specificity of Ciz1 depletion, transcript levels were monitored at 24 hours, before proliferation is significantly inhibited (FIG. 6C). At this point Ciz1 transcripts were reduced to 42% of the level in control cells treated with GAPDH siRNA. These experiments show that Ciz1 is required for cell proliferation and are consistent with a primary function in DNA replication.

Figure 6D:
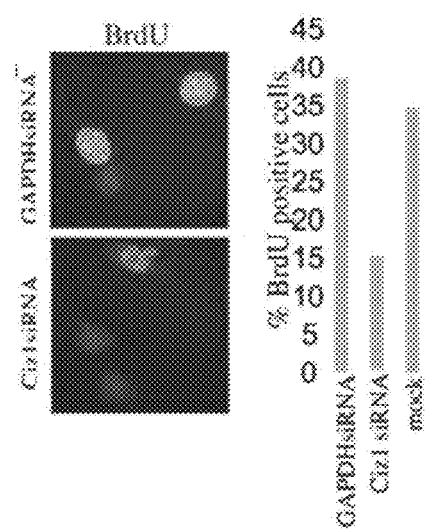

To test this further, cells were pulse-labelled with BrdU 48 hours after siRNA treatment to determine the fraction of cells engaged in DNA synthesis (FIG. 6D). When Ciz1 levels were reduced the BrdU labelled fraction was also reduced, suggesting that DNA synthesis is inhibited under these conditions. Furthermore, cells in the Ciz1 depleted population that did incorporate BrdU (approximately 15% of the population) were less intensely labelled. Therefore, in some Ciz1 siRNA treated cells S phase is slowed down rather than inhibited completely, possibly due to incomplete depletion.

Inhibition of DNA synthesis by Ciz1 siRNAs could be a secondary consequence of a general disruption of nuclear function. Therefore, we looked in more detail at a range of other replication proteins whose levels are regulated in a cell cycle dependant manner, to ask whether depleted cells arrest randomly, or accumulate at a particular point.

Figure 6E:
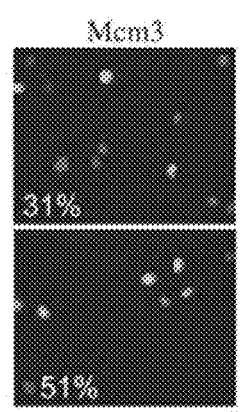
Figure 6F:
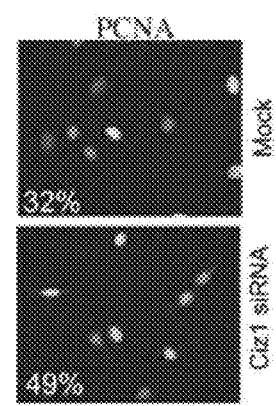

During initiation of eukaryotic DNA replication Mcm complex proteins assemble at replication origins in late G1, in a Cdc6-dependent manner. Sometime later, DNA polymerases and their accessory factors (including PCNA) become bound to chromatin and origins are activated. This is associated with nuclear export and proteolysis of the majority of Cdc6 and, as DNA synthesis proceeds, gradual displacement of the Mcm complex from chromatin (Bell and Dutta, 2002). In order to identify the point of action of Ciz1 we used immuno-fluorescence to monitor Mcm3 and PCNA. In Ciz1 depleted cells (FIG. 6E, F) both proteins were detectable within the nucleus bound to detergent resistant nuclear structures. Therefore, these factors are unlikely to bind directly to Ciz1, or to be dependent upon Ciz1 for their assembly. In fact, in four independent experiments the average number of cells with detergent-resistant chromatin-bound Mcm3 actually increased from 31% (+/−6%) to 51% (+/−5%) (FIG. 6E). Increased Mcm3 indicates that the Ciz1 dependent step occurs after pre-replication complex assembly (but before completion of S phase). In the same cell populations the PCNA positive fraction also increased, from 32% (+/−5%) to 49% (+/−6%) (FIG. 6F), narrowing the point of Ciz1 action to after PCNA assembly. Thus, Ciz1 most likely acts to facilitate DNA replication during a late stage in the initiation process, while failure to act inhibits progression through S phase, leaving Mcm3 and PCNA in place.

Taken together, our cell-free and cell-based investigations paint a consistent picture about the primary function of Ciz1. They suggest that Ciz1 is a novel component of DNA replication factories, and they show that Ciz1 plays a positive role in the mammalian cell-cycle, acting to promote initiation of DNA replication.

Three of our lines of investigation suggest that Ciz1 is required during a late stage in the initiation process after pre-replication complex formation. First, p85 (p100)-Ciz1 antigen accumulates in nuclei exposed to cyclin A-cdk2 concentrations that activate DNA synthesis, implying that Ciz1 functions during this step rather than during earlier replication complex assembly steps (Coverley et al., 2002). Second, functional studies with late G1 nuclei show that recombinant ECiz1 increases the number of nuclei that incorporate labeled nucleotides in vitro. Therefore, Ciz1 must be active in a step that converts nuclei that are poised to begin DNA synthesis into ones that are actively synthesizing DNA. Third, RNA interference studies point to a Ciz1-dependent step after Mcm complex formation and after PCNA has become assembled onto DNA, but before these proteins are displaced. These distinct lines of investigation lead to strikingly similar conclusions about the point of action of Ciz1 placing it in the later stages of initiation.

Anti-Ciz1 siRNA as a Therapeutic Strategy

Our analysis shows that Ciz1 is essential for cell proliferation, and that targeting Ciz1 is a viable strategy to restrain proliferation. The alternatively spliced forms of Ciz1 that we observe in various cancers (see below) means that Ciz1 could be targeted in a selective way to restrain proliferation in a subset of cells within a population.

By way of example, this could be done by targeting siRNA's to the junction sequence created in Ciz1 transcripts when the C-terminal sequence GTTGAGGAGGAACTCT-GCAAGCAG (SEQ ID NO:2) is missing, in small cell lung carcinoma cells, or by using Ciz1 protein lacking the corresponding VEEELCKQ (SEQ ID NO: 3) sequence to select specific chemical inhibitors.

Accordingly the present invention also provides for the use of junction sequences created in Ciz1 transcripts and proteins when alternatively spliced sequences are not present, as a diagnostic marker, prognostic indicator or therapeutic target.

Embryonic form Ciz1 is localized to the nucleus RT-PCR analysis across potentially variable exons suggest that 3T3 cells predominantly express full-length Ciz1, so our immuno-localization work on endogenous Ciz1 (FIG. 5) does not necessarily reflect the behavior of ECiz1, which lacks several sequence blocks and possibly therefore information that is used to localize the protein. To directly compare the localization of ECiz1 and full-length Ciz1, enhanced GFP tagged constructs were transfected into 3T3 cells (FIG. 8A), and microinjected into mouse pro-nuclei (FIG. 8B). In all cases tagged Ciz1 and ECiz1 were exclusively nuclear, while a control construct expressing GFP alone was present in the nucleus and the cytoplasm. GFP-Ciz1 and GFP-ECiz1 were both visible in live cells as sub-nuclear foci, similar to replication foci seen in fixed cells by immuno-fluorescence. Thus, the three sequence blocks that are absent from ECiz1 do not appear to contribute to the nuclear localization of Ciz1.

Over the three day period following transfection no cell division was observed in the GFP-Ciz1 and GFP-ECiz1 transfected cells. These data suggest that overexpression of functional Ciz1 has an inhibitory effect on the cell cycle (in cells that have their regulatory pathways intact).

Coalescence

Figure 8A:
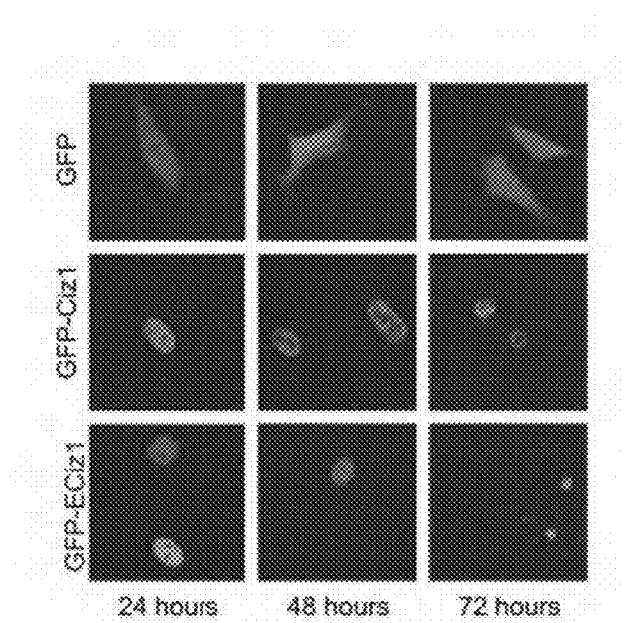
FIG. 8A-8E show transient transfection of mouse 3T3 cells. GFP-tagged Ciz1 constructs were transfected into NIH3T3 cells (FIG. 8A) or microinjected into the male pro-nucleus of fertilized mouse eggs at the one cell stage (FIG. 8B). By 24 hours Ciz1 and ECiz1 became localized to the nucleus forming a subnuclear spotty pattern, while GFP alone was present in both the nucleus and the cytoplasm.
Figure 8B:
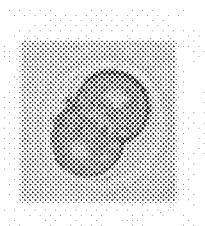
Figure 8C:
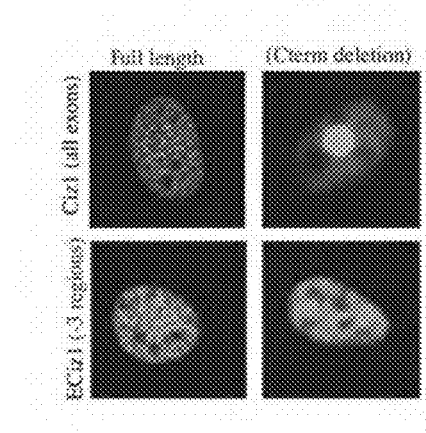

When GFP-tagged constructs in which the C-terminal one third of Ciz1 had been removed were transfected into 3T3 cells, differences between ECiz1 and full length Ciz1 were observed (FIG. 8C). By 48 hours FL Ciz1 N-term(442 equivalent) had coalesced into large intra-nuclear blobs which only became apparent in the ECiz1 N-term442 transfected population by day 3 or later. Before this time ECiz1 N-term442 was localized as a nuclear specific but diffuse pattern. Thus ability to coalesce is quantifiably different between Ciz1 and ECiz1, and is therefore affected by one of the three alternatively spliced exons (2/3, 6 or 8).

Like cells transfected with full length Ciz1 and ECiz1, cells transfected with constructs in which the C terminal one third was removed were not seen to multiply during the three day monitoring period.

C-Terminal Domains Anchor Ciz1 to Nuclear Structures

Figure 8D:
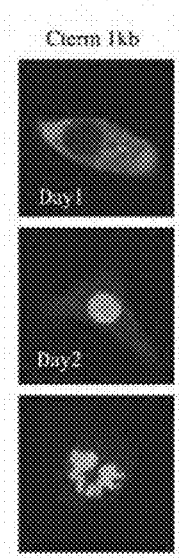

As described above, the difference between Ciz1 and ECiz1 N-term is masked when C-terminal domains are also present (FIG. 8A). Furthermore the C-terminal fragment alone directs GFP tag to chromatin, forming an irregular pattern that is not as spotty (focal) as Ciz1 or ECiz1, but which remains attached to chromosomes during mitosis (FIG. 8D). This suggests that C-terminal domains are involved in immobilizing Ciz1 on a structural framework in the nucleus. Notably, cells transiently transfected with C-terminal fragment continued to divide resulting in gradual dilution of green fluorescence.

Ectopic Ciz1 Promotes Premature Entry to S Phase

Figure 8E:
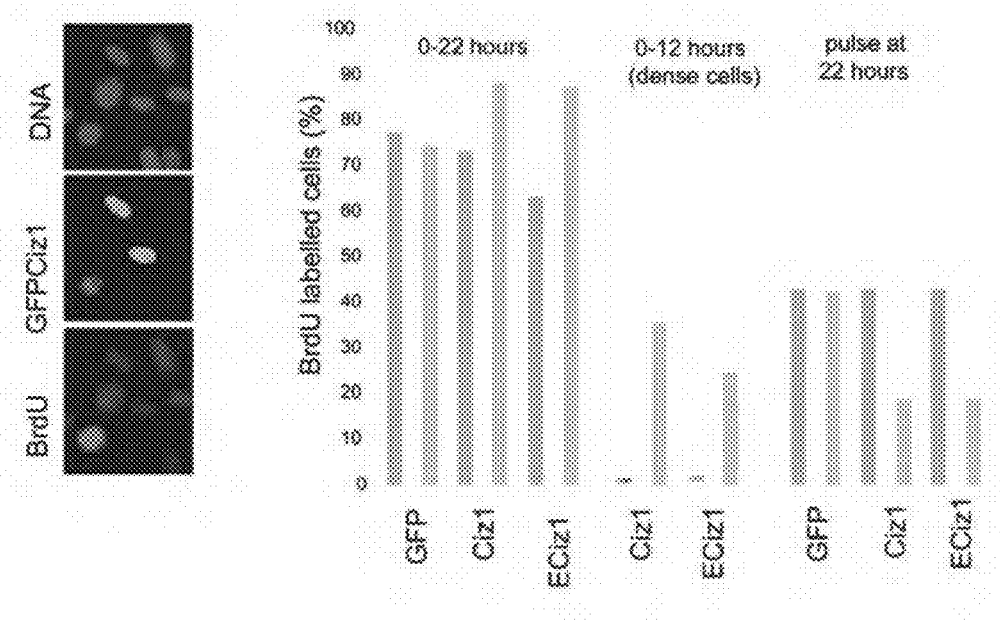

We looked at events occurring during the first day after transfection. The S phase fraction in transfected cells (green) was compared to the S phase fraction in untransfected cells, by labelling with BrdU at various intervals. During long labelling windows including 0-22 hours (FIG. 8E), 0-12 hours and 0-7 hours (not shown), consistently more of the Ciz1 and ECiz1 transfected cells were engaged in DNA synthesis, compared to untransfected cells. This suggests that Ciz1 and ECiz1 have a positive effect on the G1-S transition, promoting unscheduled entry to S phase. Similar results were obtained with 3T3 cell populations that were densely plated before transfection. This was done in order to minimize the fraction in the untransfected population that was engaged in S phase as part of the normal cell cycle. Under these conditions the difference between the transfected and untransfected population was maximized, clearly demonstrating the effect of ectopic Ciz1 on initiation of DNA replication.

Conversely, when cells were labelled with BrdU during a short pulse administered at 22 hours (FIG. 8E), or at 10 hours or 12 hours post-transfection (not shown), the labelled fraction was consistently reduced in the Ciz1 and ECiz1 transfected populations. This suggests that the S phase that is induced by ectopic Ciz1 or ECiz1 is abnormal, with slow or aborted DNA synthesis that is not sufficient to label cells during short windows of exposure to BrdU.

Therefore, ectopic Ciz1 and ECiz1 have two effects on S phase in cultured cells. They promote DNA replication, but this results in slow or aborted DNA synthesis.

Clones with Altered Proliferation Potential

Figure 9A:
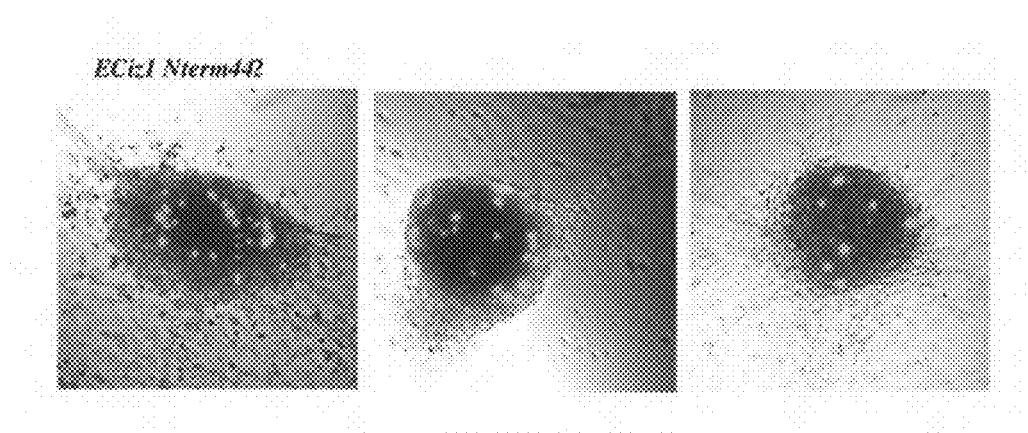
FIGS. 9A and 9B show altered proliferation potential and cell morphology in transfected populations. Cell clusters arise in transfected 3T3 cell populations. Cells were transfected with the N-terminal two thirds of Ciz1 (FIG. 9B) or ECiz1 (N-term442) (FIG. 9A) tagged with GFP, and maintained under selection with 50 µg/ml G418. After three weeks under selection, cell aggregates were visible with GFP positive cells within.
Figure 9B:
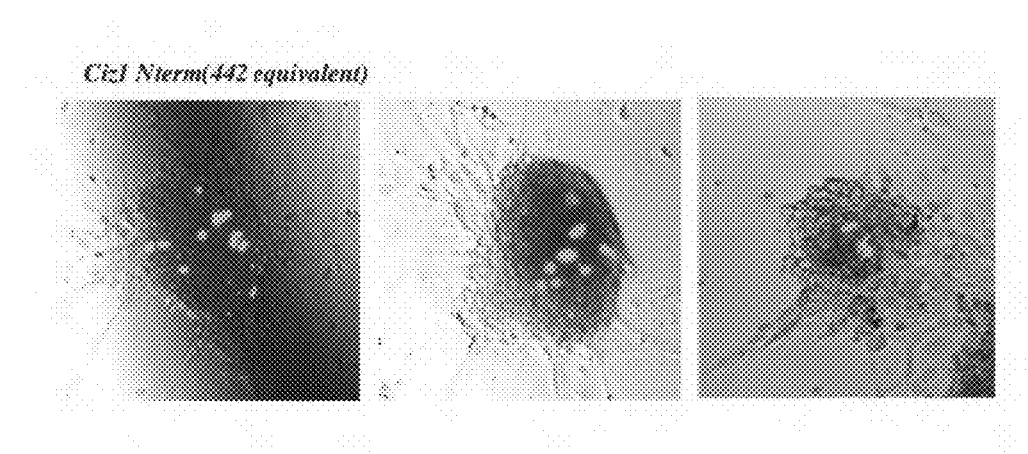

We also monitored transfected populations of 3T3 cells over a three week time period. In cells transfected with the GFP-Nterm442 or the non-alternatively spliced equivalent and maintained under selection with G418, large foci containing hundreds of cells were observed (FIG. 9A). These clusters contained large numbers of GFP expressing cells, demonstrating that over-expression of the N-terminal portion of ECiz1 (in which replication activity resides) is not lethal, and suggesting that over-expression leads to altered proliferation phenotype, compared to untransfected cells, including loss of contact inhibition and failure to form a monolayer. This Ciz1-dependent altered behavior could contribute to tumor formation. A similar truncated version of mouse Ciz1, lacking putative chromatin interaction domains was previously isolated from a mouse melanoma (FIG. 2).

Human Ciz1 and Cancer
Ciz1 cDNAs in Public Databases

Figure 10A:
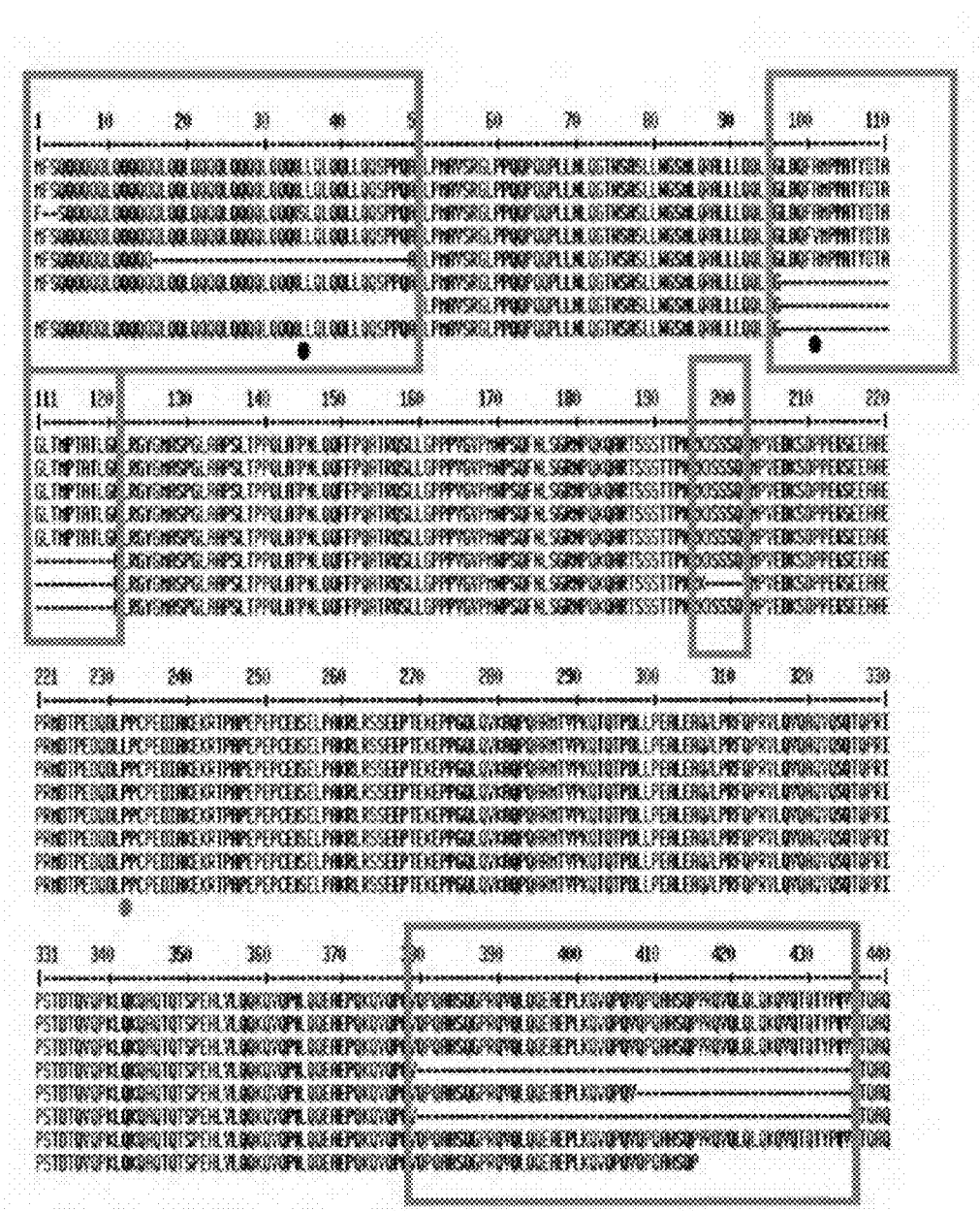
FIGS. 10A and 10B show human Ciz1 splice variants (SEQ ID NO: 29-36, respectively) in pediatric cancers. When joined at match line A-A, FIGS. 10A and 10B form one figure. There are seven human Ciz1 cDNAs in public databases, but only one is derived from normal adult tissue (B cells) and it contains all predicted exons. The other six are derived from embryonic cells or pediatric cancers. Five of these are alternatively spliced with variability in exons 2, 3, 6, and 8 (like mouse ECiz1), and also in exon 4 (like mouse ES cells, primordial germ cells and testis). The sixth (AF159025) lacks the first methionine and contains single-nucleotide polymorphisms that give rise to amino-acid substitutions. All differences from the predicted sequence (AB030835) are marked.
Figure 10B:
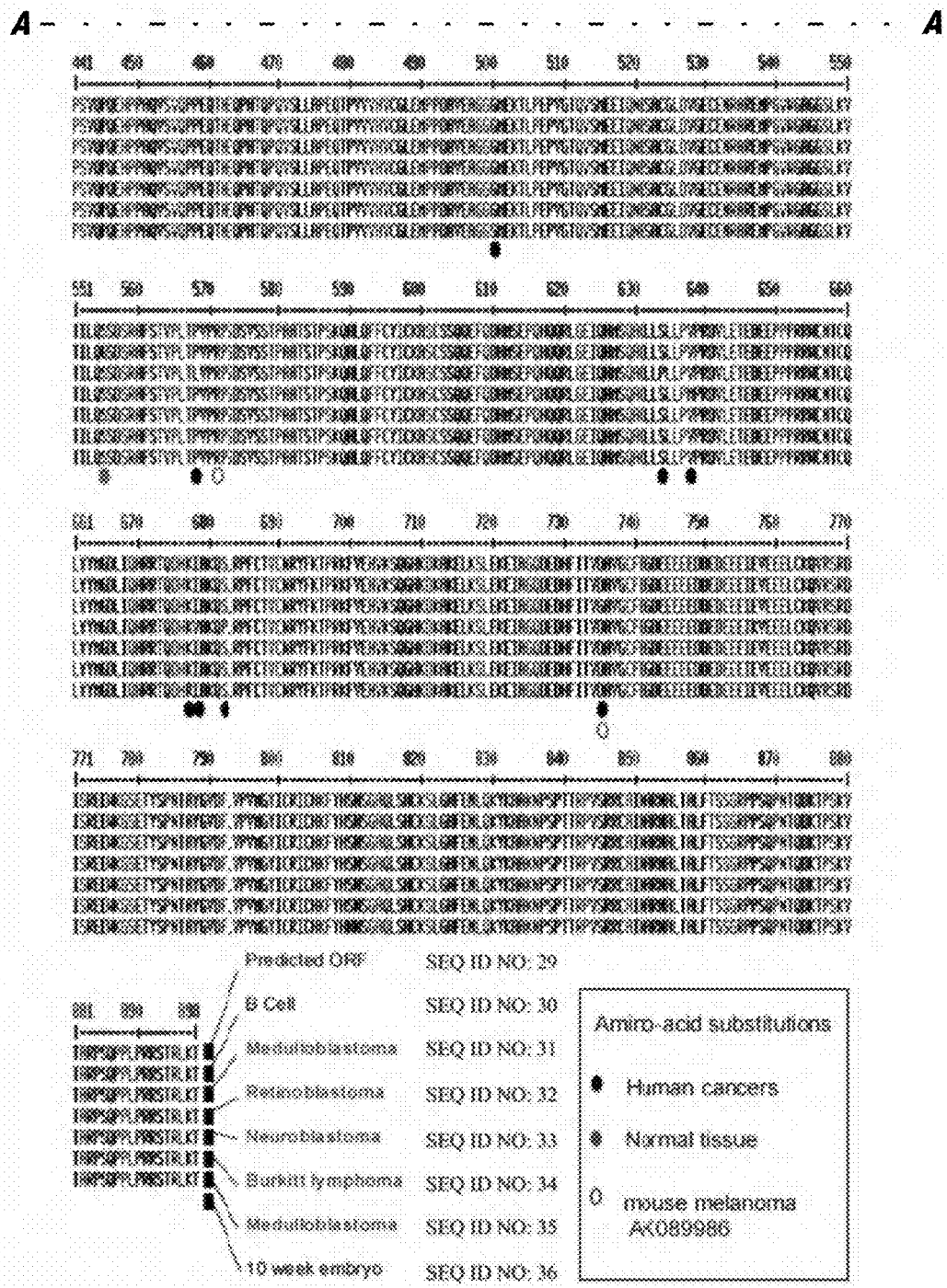
Figure 11A:
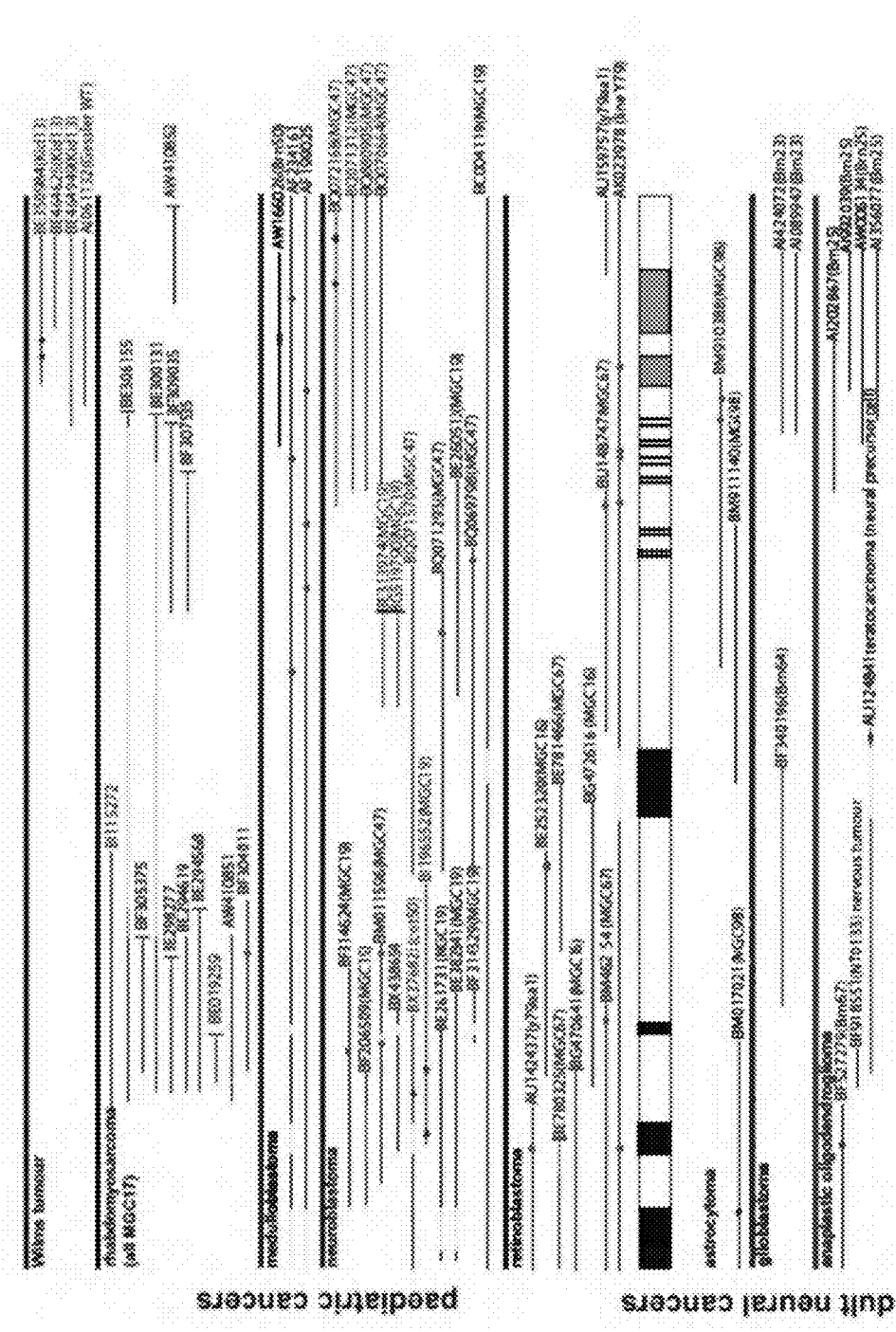
FIG. 11A-11F show EST sequence analysis. On each map a schematic representation of the Ciz1 protein is included for reference, showing the positions of alternatively spliced exons (black), putative chromatin interaction domains (grey) and predicted zinc fingers (black vertical lines). All EST sequences are accompanied by their Genbank accession number with the library from which they were derived indicted in parentheses. Sequences absent from Ciz1 ESTs due to alternative splicing are shown in yellow, frame-shifts in red and putative deletions in grey. Single nucleotide polymorphisms that give rise to amino-acid substitutions are indicated by black dots and some of these occur in a consensus cdk phosphorylation site which we have shown to be important for the regulation of Ciz1 activity (blue dots). Position of the inserted sequence in the carcinoma cell line MGC102 is indicated by a triangle.
Figure 11B:
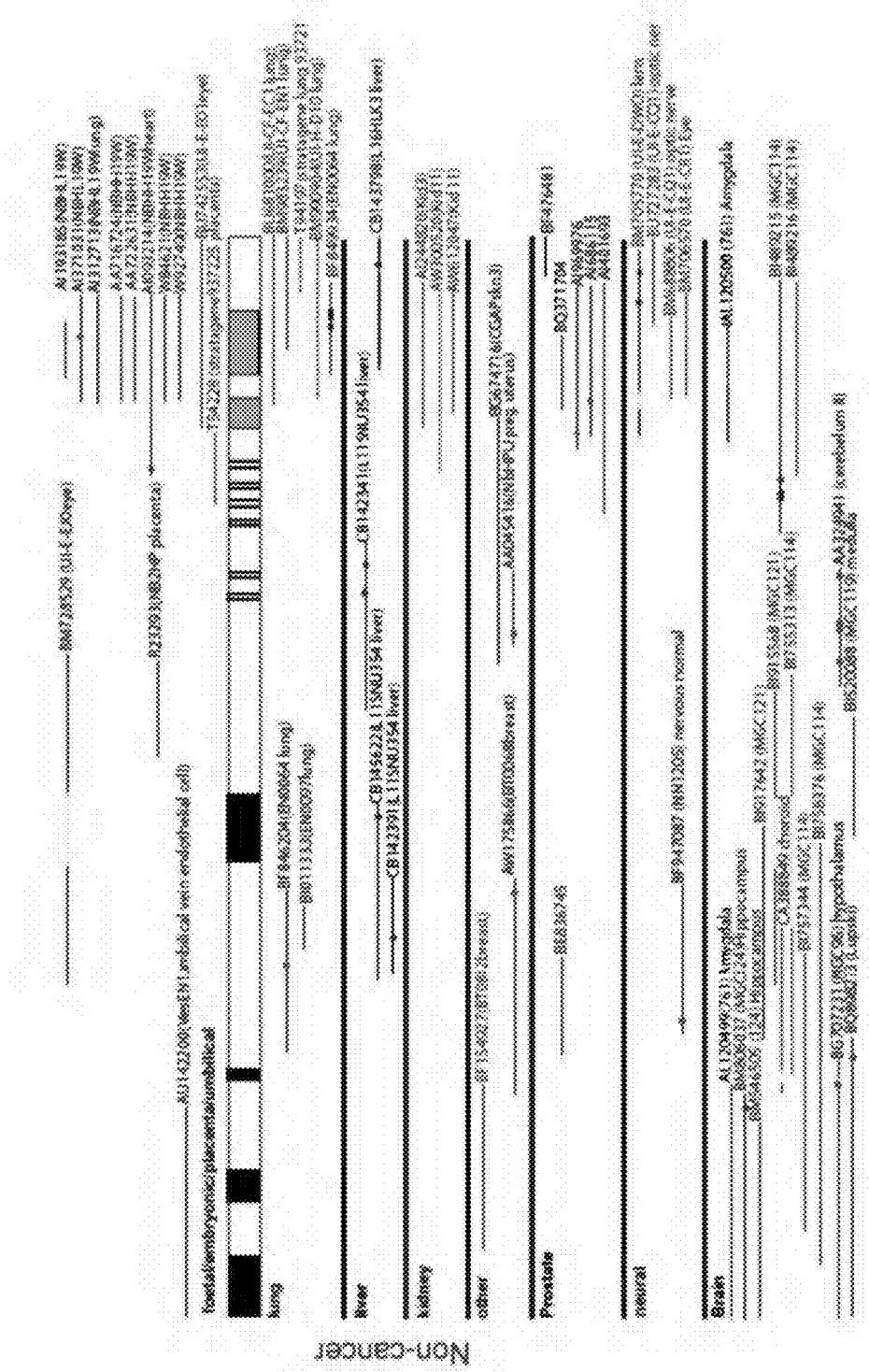
Figure 11C:
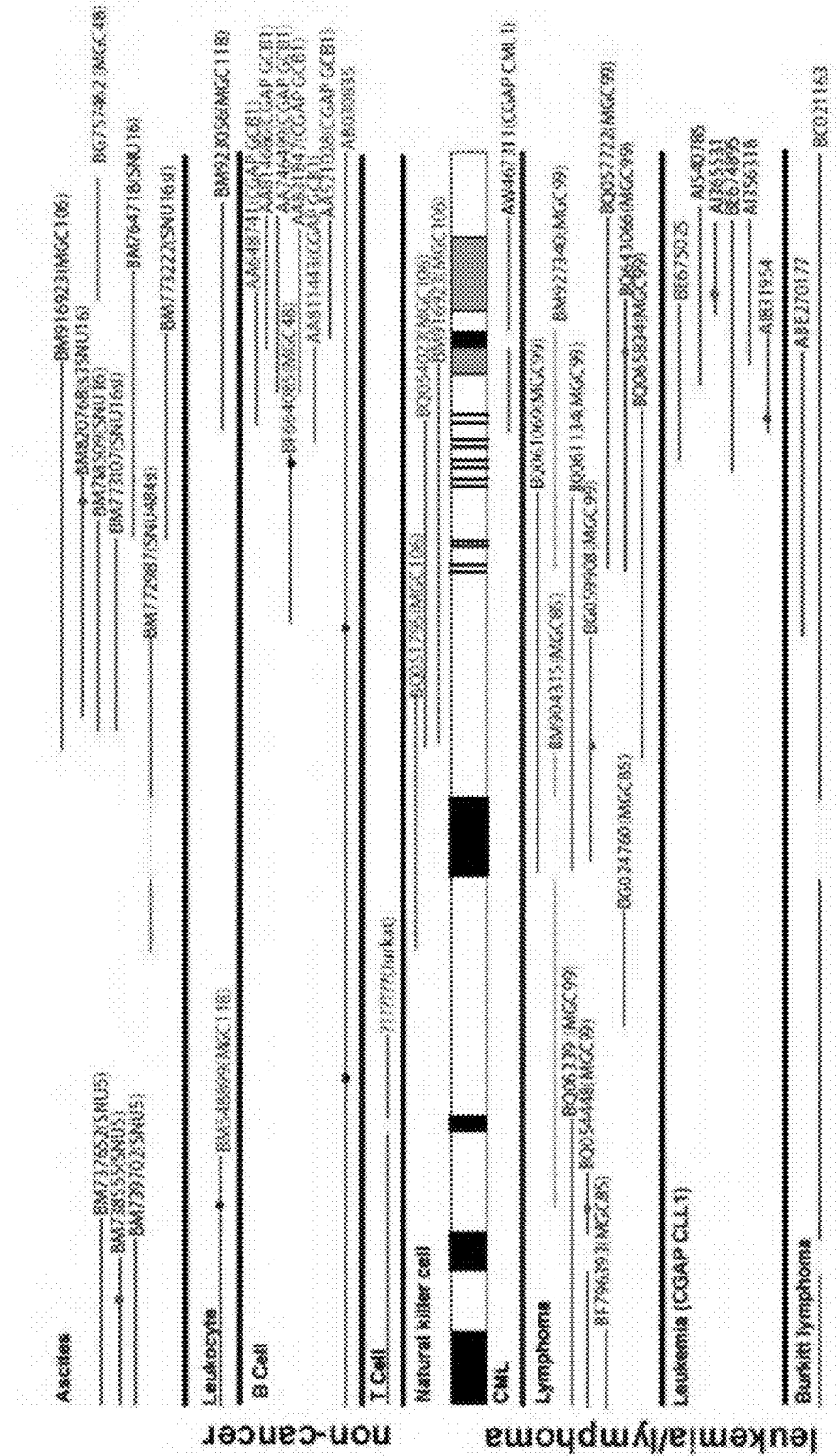
Figure 11D:
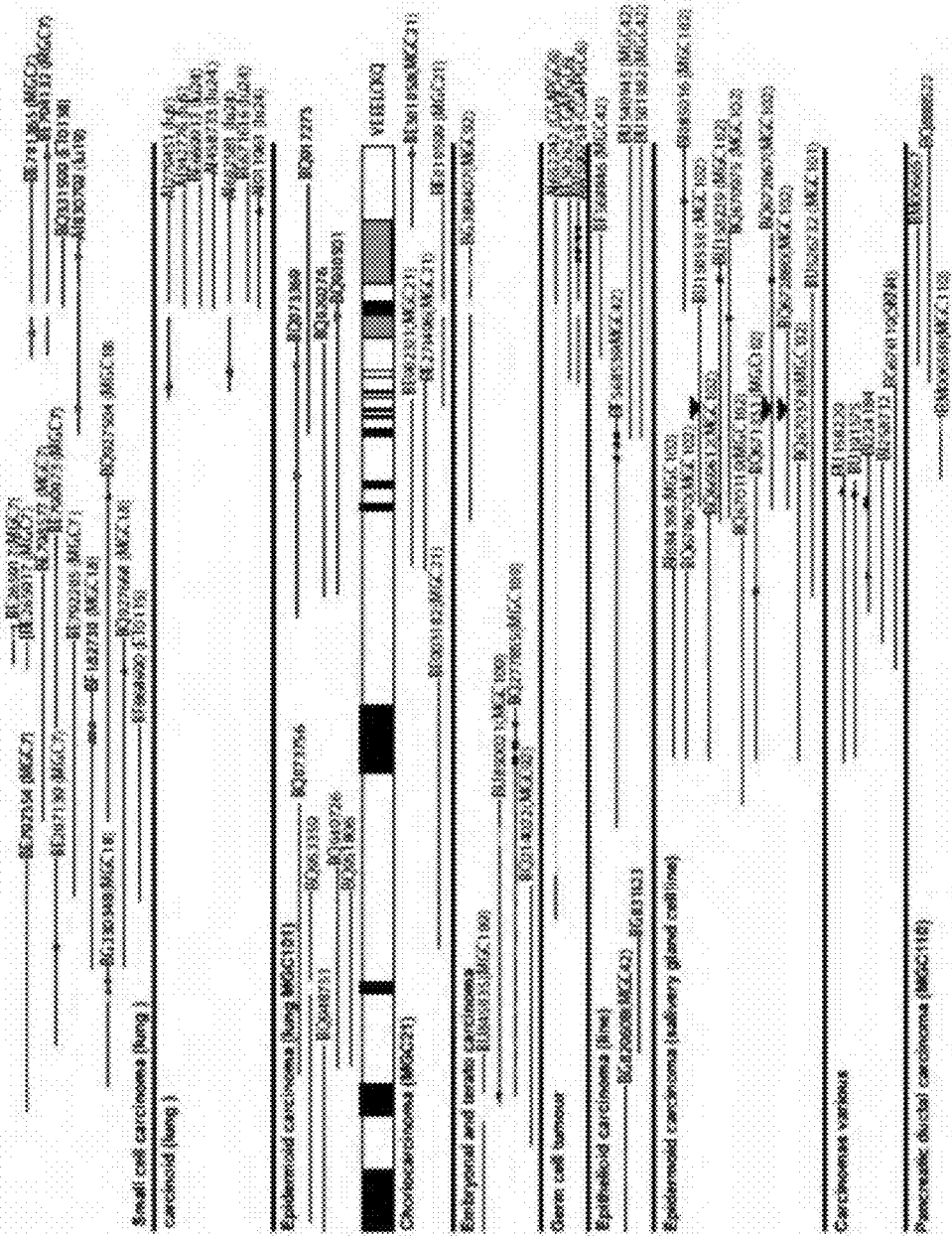
Figure 11E:
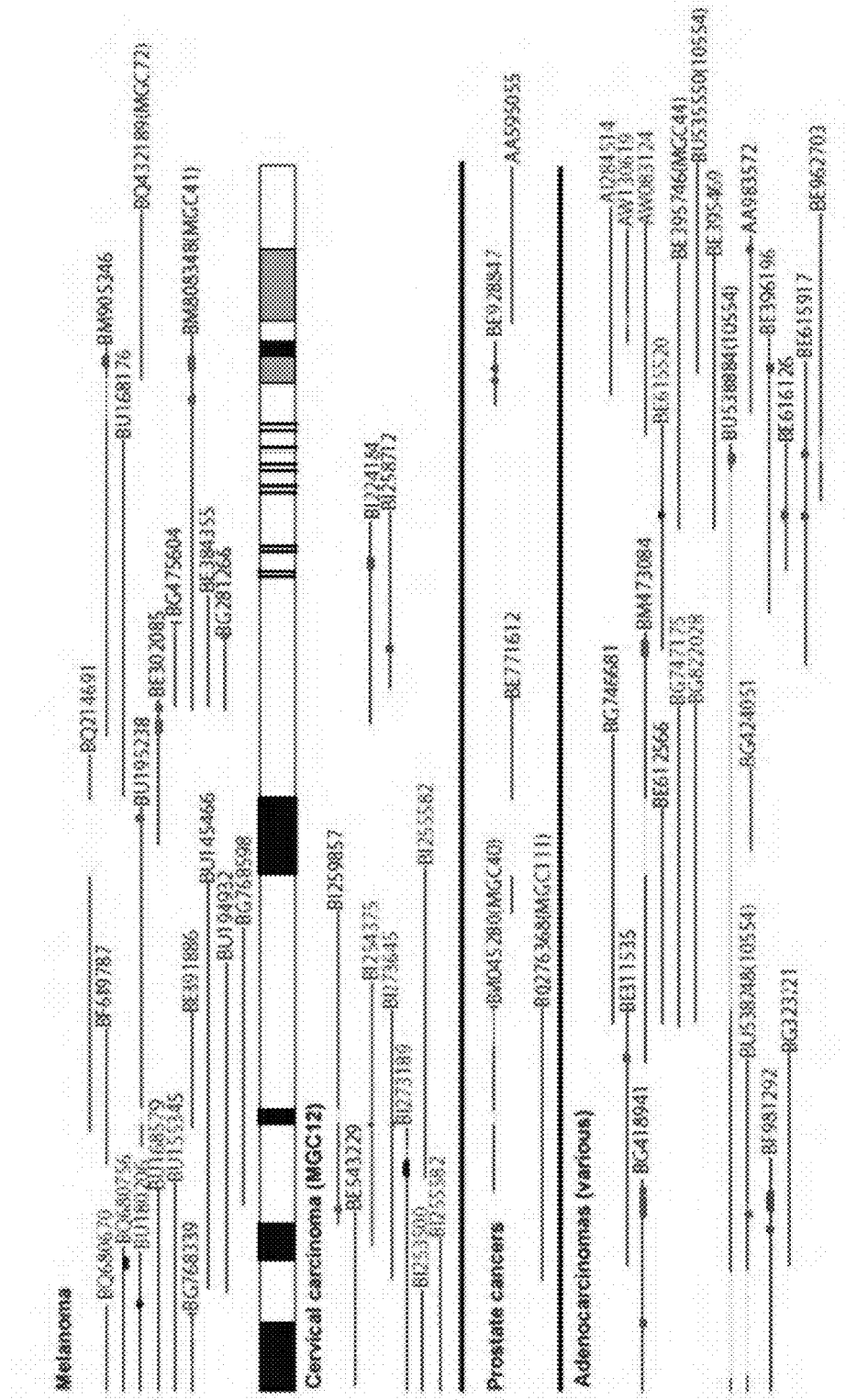
Figure 11F:
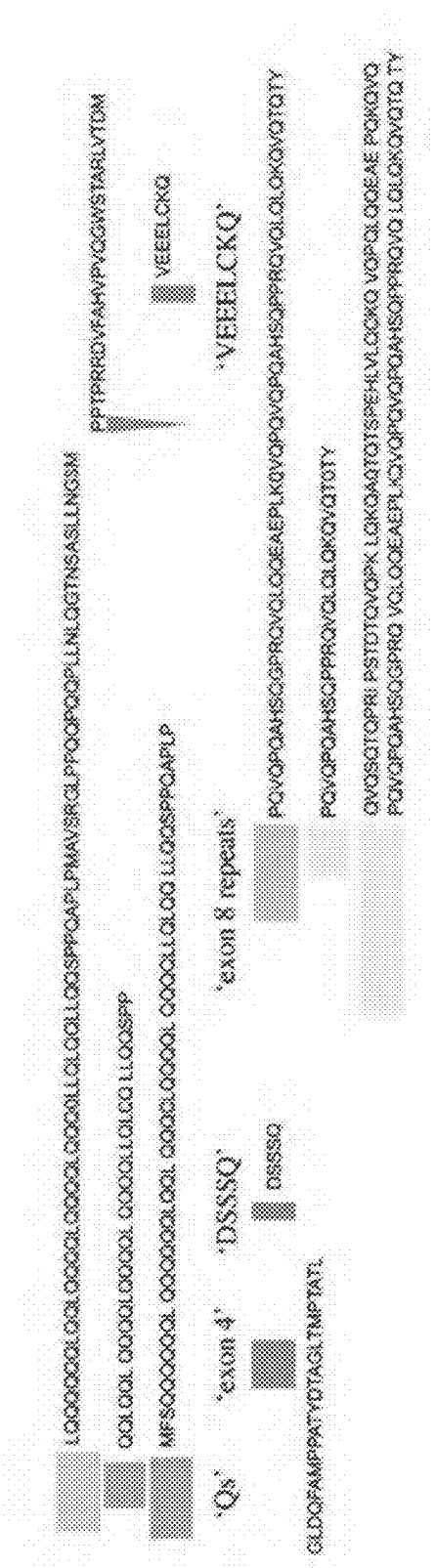

As mentioned above human Ciz1 is alternatively spliced at the RNA level to yield transcripts that lack three of the same exons as mouse embryonic Ciz1. Seven human Ciz1 cDNAs have been recorded in public databases (FIG. 10), submitted by Mitsui et al (1999), Warder and Keherly (2003) and large-scale genome analysis projects (NIH-MGC project, NEDO human cDNA sequencing project). Only one is derived from normal adult tissue, and this contains all predicted exons (AB030835). The rest are derived from embryonic cells (AK027287), or notably from four different types of pediatric cancer (medulloblastoma, AF159025, AF0234161, retinoblastoma, AK023978, neuroblastoma, BC004119 and Burkitt lymphoma, BC021163). The embryonic form and the cancer derived forms lack sequence blocks from the same three regions as our embryonic mouse clone, and from a fourth region which corresponds to exon 4. Therefore, the limited data suggests that alternatively spliced forms are more prevalent early in development. This correlation has not previously been noted in the scientific literature. The presence of alternatively spliced Ciz1 in pediatric cancers raises the possibility that Ciz1 mis-splicing might be linked to inappropriate cell proliferation.

For example, one of the variable exons encodes a short conserved DSSSQ (SEQ ID NO:1) sequence motif that is absent in mouse ECiz1 and in a human medulloblastoma. This is directly adjacent to the consensus cdk phosphorylation site that we have shown to be involved in regulation of ECiz1 function. Conditional inclusion of the DSSSQ (SEQ ID NO:1) sequence might make Ciz1 the subject of regulation by the ATM/ATR family of protein kinases, which phosphorylate proteins at SQ sequences, thereby restraining Ciz1 initiation function in response to DNA damage.

Analysis of Expressed Sequence Tags

The presence of alternatively spliced Ciz1 in pediatric cancers prompted a detailed analysis of Ciz1 ESTs. There are 567 expressed sequence tags (ESTs) included in NCBI unigene cluster Hs.23476 (human Ciz1). These are derived from a wide range of normal and diseased tissues and cell lines. Sequences have been translated and mapped against the predicted full-length amino-acid sequence of human Ciz1. Sequence alterations that give rise to amino-acid substitutions, deletions, frame-shifts and premature termination of translation have been recorded.

Alternatively spliced Ciz1 variants were also seen in this EST data set and are recorded here. The four sequence blocks that we previously reported to be alternatively spliced in human and mouse Ciz1 (FIG. 2) were observed in the EST sequences, as well as a previously undetected variant that lacks the exon 14 derived sequence VEEELCKQ (SEQ ID NO: 3). All of these recurrently variant sequence blocks are bounded by appropriate splice sites. A sixth variable sequence block was identified in one carcinoma derived library, caused by inclusion of GCCACCCACACCAC-GAAGAGATGTGTTGCCCACGTTCCAGTGCA-GGGGTGGAGCA CAGCCCGGCTTGTTACAGATAT (SEQ ID NO: 4).

ESTs are grouped according to the cell type from which they were derived with the primary divisions occurring between neoplastic cells of adult, childhood or embryonic origin. ESTs from normal tissue of embryonic or adult origin are included for comparison. EST-derived Ciz1 protein maps are shown in FIG. 11A-E and the alternatively spliced exons summarized in FIG. 11 F.

Three sequence blocks in the N-terminal end of human Ciz1 are absent in transcripts from medulloblastomas and neuroblastoma (FIG. 11A), and occasionally absent from Ciz1 transcripts from other cancers. We also found similar alternative splicing in a third pediatric cancer, Ewings sarcoma (see below). Pediatric cancer-associated alternatively spliced sequences are from exons 2/3 (at least two versions), exon 4 and exon 6.

Exon 8 variants in which one or more copies of a Q-rich degenerate repeat are absent have been noted in transcripts derived from normal cells (of embryonic or adult neural origin) and from various cancers. Alternative splicing in this region could produce Ciz1 with inappropriate activity, therefore exon 8 variant expression, or occurrence of point mutations which influence splicing in this region, might be useful as diagnostic or prognostic markers in cancer. The alternatively spliced degenerate repeats in exon 8 are detailed below and summarized in FIG. 11F.

In the C-terminal half of the human Ciz1 protein two sequence blocks are variably spliced. One of these is missing from transcripts derived from three out of five lung carcinoma and lung carcinoid libraries, and from three other carcinoma libraries (but very rarely from transcripts from other cell types).

The second variant sequence block is due to inappropriate inclusion of extra sequence in transcripts from the epidermoid carcinoma library (MGC102).

These sequences and the junction sequences formed in Ciz1 proteins, and Ciz1 transcripts when these segments are excluded or included, are potential targets for selective inhibition of cell proliferation in a wide range of different cancers. The remaining non-variant sequences are potential targets for non-selective inhibition of cell proliferation.

In addition to splicing variations, other non-typical Ciz1 transcripts were found to preferentially occur in some cancers. In Rhabdomyosarcomas Ciz1 is prematurely terminated leading to a predicted protein that lacks C-terminal nuclear binding domains. This could lead to inappropriate DNA replication and might therefore be a therapeutic target or marker in this type of cancer.

Several transcripts contain point mutations that lead to amino-acid substitutions in putative cyclin-dependent kinase (cdk) phosphorylation sites. In the cervical carcinoma library MGC12, this occurs twice. We have shown that two cdk phosphorylation sites are involved in restraining Ciz1 activity (FIGS. 3C and D), implicating these mutations in the deregulation of proliferation in cancer cells. One of these is the same as the carcinoma-derived mutant mentioned above (FIG. 11E). Cancer-derived transcripts with point mutations in Ciz1 could also be targeted by RNA interference, or have value as diagnostic or prognostic indicators.

Investigation of Ciz1 Variant Expression in Pediatric Cancers

Figure 12A:
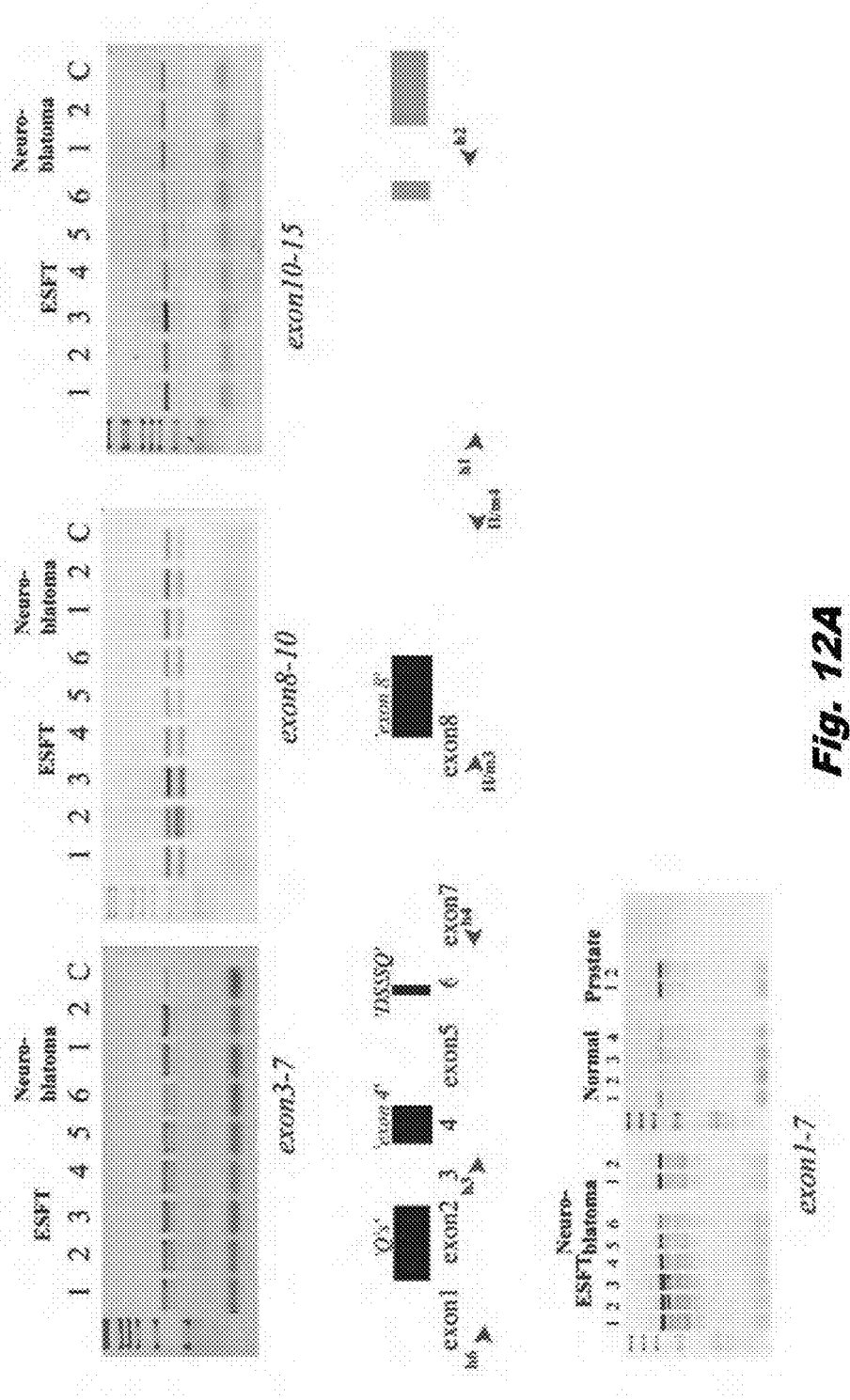

Ciz1 variant expression was investigated in 6 Ewings sarcoma family tumor cell lines (ESFTs) and two neuroblastoma cell lines, using RTPCR with primer sets that span three regions of known Ciz1 variability (FIG. 12A). This analysis showed that the pattern of Ciz1 variant expression is different in ESFT cells compared to neuroblastoma cells compared to non-transformed cells, but apparently very similar within sets of cell lines from the same tumor. Therefore, Ciz1 variant expression could have prognostic or diagnostic potential for these cancers. Minor variations within a set of lines from the same tumor type could have prognostic value.

By subcloning and sequencing amplified transcripts we found that all six ESFT lines tested express an exon 4 minus form of Ciz1. As Ciz1 is essential for cell proliferation (see below), this offers a possible route for selective restraint of ESFT cells. Transcripts from the two neuroblastoma cell lines tested rarely lack exon 4 but frequently lack sequences the DSSSQ (SEQ ID NO: 1) motif encoded by exon 6 (FIG. 12B).

This experimental analysis confirms that pediatric cancers express forms of Ciz1 with variable inclusion of exons 4, 6 and probably exons 2/3.

Two versions of the sequence encompassing exon 8 and one form of the sequence encompassing the VEEELCKQ-coding sequence were detected in ESFTs, neuroblastomas and control suggesting that these regions do not contribute to deregulation of Ciz1 in these paediatric cancers.

In all cases, Ciz1 RT-PCR products were most abundant in reactions carried out with RNA samples from cancer cell lines, compared to controls (Wi38, HEK293, NIH3T3 cells, and primary human osteoblasts). This is consistent with increased expression of Ciz1 variants in tumors.

Analysis of Ciz1 Protein Expression in Prostate Cancer Cell Lines

Figure 13A:
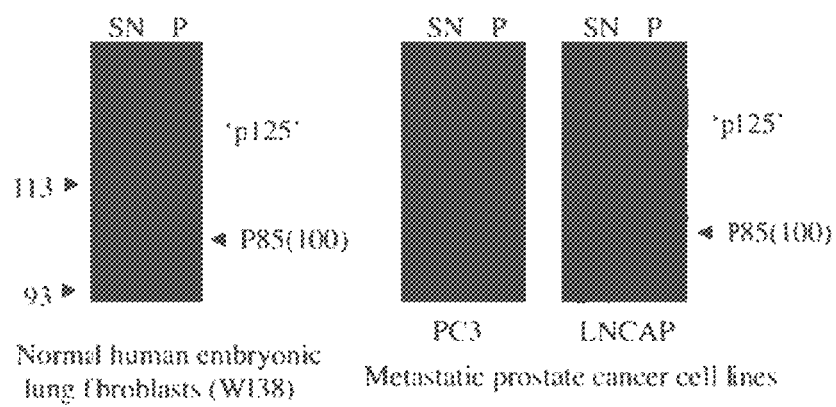
FIGS. 13A and 13B show Ciz1 isoforms in normal human fibroblasts (Wi38) and metastatic prostate cancer cell lines (PC3 and LNCAP).
Figure 13B:
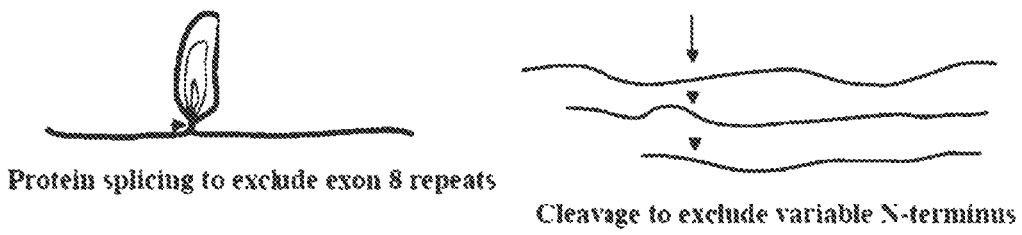

Normal, non-transformed human lung fibroblasts (and mouse NIH3T3 cells) express two major forms of Ciz1 that are detected by anti-Ciz1 polyclonal antibody 1793 in western blots (FIG. 13A). The larger (approximately 125 kDa) band resolves into three distinct bands that are present in equal proportions in Wi38 cells, but grossly uneven proportions in prostate cancer cell lines PC3 and LNCAP (and ESFT cell lines—not shown). We postulate that these protein isoforms are generated by expression of variably spliced exons. Both tumor cell lines also contain more Ciz1 antigen than Wi38 cells, consistent with over-expression of Ciz1 in these cancer cell lines.

Taken together, our results (experimental and bioinformatics analysis of genome data) support the conclusion that Ciz1 is mis-regulated in a wide range of human cancers. We have shown that the Ciz1 protein plays a positive role in the DNA replication process, therefore mutant Ciz1 could contribute to cellular transformation, rather than be a consequence of it. If deregulation of Ciz1 is a common step in this process it represents a very attractive target for development of therapeutic agents.

We have also associated particular changes with specific cancers, making it a real possibility that Ciz1 could be useful as a diagnostic or prognostic marker.

These include:—
  Alternative splicing in the N-terminal part of the protein (that contains replication activity in vitro) in pediatric cancers.
  Point mutations in cyclin-dependent kinase phosphorylation sites known to be involved in restraining Ciz1 replication activity.
  Non-typical expression and nuclear binding properties of Ciz1-p125 forms in prostate carcinoma cell lines, possibly due to mis-regulated splicing of the degenerate repeats in exon 8, or other exons.
  Conditional exclusion of a discrete motif (VEEELCKQ) in the C-terminal end of Ciz1 (probably involved in localization of Ciz1 protein within the nucleus) in small cell carcinoma of the lung and other carcinomas.
  Increased levels of Ciz1 protein and RNA (detected by Western blot and by RT-PCR) in all cancer derived cells lines tested so far, compared to Wi38 normal embryonic lung fibroblast, human osteoblast RNA and mouse NIH3T3 fibroblasts.

The sequences shown in FIGS. 14 to 21 are of use for the development of therapeutic, diagnostic, or prognostic reagents.

Materials and Methods
Cloning.

A lamba triplEx 5'-stretch, full length enriched cDNA expression library derived from 11 Day old mouse embryos (Clontech ML5015t) was used to infect E. coli Xl1blue according to the recommended protocol (Clontech). Plaques were lifted onto 0.45 micron nitrocellulose filters pre-soaked in 10 mM IPTG (Sigma). Affinity purified antibody V1 was applied to approximately $3\times10^6$ plaques at 1/1000 dilution in PBS, 10% non-fat milk powder, 0.4% Tween20, after blocking for 30 minutes in the absence of antibody. After two hours filters were washed three times with the same buffer and reactive plaques were visualized with anti-rabbit secondary antibody conjugated to horse-radish peroxidase (Sigma), and enhanced chemi-luminescence (ECL, Amersham) according to standard procedures. 43 independent plaques were picked but only two strains of phage survived a further three rounds of screening. These were converted to pTriplEx by transforming into BM25.8 and sequenced. One codes for mouse Cdc6 (clone P) and the other (clone L) for an unknown mouse protein that is homologous to human Ciz1. We refer to this as embryonic Ciz1 (ECiz1) and it was submitted to EMBL under the accession number AJ575057.

Bacterial expression pGEX based bacterial expression constructs (Amersham) were used to produce ECiz1 proteins for in vitro analysis. pGEX-ECiz1 was generated by inserting a 2.3 kb SmaI-XbaI (blunt ended) fragment from clone L into the SmaI site of pGEX-6P-3. pGEX-Nterm442 was generated by inserting the 1.35 kb XmaI-XhoI fragment into XmaI-XhoI digested pGEX-6P-3, and pGEX-Cterm274 by inserting the 0.95 kb XhoI fragment into XhoI digested pGEX-6P-3. pGEX-T(191/2)A was generated from pGEX-ECiz1 by site directed mutagenesis (Stratagene Quikchange) using primers AACCCCCTCTTCCGCCGCCCCCAATCG-CAAGA (SEQ ID NO: 5) and TCTTGCGATTGGGGGCG-GCGGAAGAGGGGGTT (SEQ ID NO: 6). pGEX-T(293)A was generated from pGEX-ECiz1 using primers AAGCA-GACACAGGCCCCGGATCGGCTGCCT (SEQ ID NO: 7) and AGGCAGCCGATCCGGGGCCTGTGTCTGCTT (SEQ ID NO: 8). Integrity and reading frame of all clones were sequence verified.

Recombinant Ciz1, Ciz1 fragments and point mutants were produced in BL21-pLysS (Stratagene) as glutathione S-transferase-tagged protein. This was purified from sonicated and cleared bacterial lysates by binding to glutathione sepharose 4B (Amersham). Recombinant protein was eluted by cleavage from the GST tag using precision protease (as recommended by the manufacturer, Amersham), into buffer (50 mM Tris-HC pH 7.0, 150 mM NaCl, 1 mM DTT). This yielded protein preparations between 0.2 and 2.0 mg/ml. For replication assays serial dilutions were made in 100 mM Hepes pH 7.8, 1 mM DTT, 50% glycerol so that not more than 1 ml of protein solution was added to 10 ml replication assays, yielding the concentrations shown. Consistent with previous observations (Mitsui et al., 1999; Warder and Keherly, 2003) recombinant Ciz1, and derived fragment N-term442 migrated through SDS-PAGE with anomalously high molecular weight. Cyclin A-cdk2 was produced in bacteria as previously described (Coverley et al., 2002).

Anti-Ciz1 Antibodies

Rabbit polyclonal antibody V1 (Coverley et al., 2000; Stoeber et al., 1998; Williams et al., 1998) was raised against an internal fragment of bacterially expressed human Cdc6 corresponding to amino-acids 145-360, and affinity purified by standard procedures (Harlow and Lane, 1988). This antibody reacts strongly with endogenous p100-Ciz1 and also with ECiz1 Nterm442 fragment. Alignment of Nterm442 with Cdc6 amino-acids 145-360 suggest that the shared epitope could be at 294-298 or 304-312 in mouse Ciz1. Recombinant Nterm442 was used to generate two Ciz1-specific polyclonal anti-sera designated 1793 and 1794 (Abcam). 1793 has been used routinely in the experiments described here. Its specificity was verified by reciprocal immuno-precipitation and western blot analysis with anti-body V, by inclusion of Nterm 442 (25 µg/ml in antibody buffer, 10 mg/ml BSA, 0.02% SDS, 0.1% Triton X100 in PBS), which blocked reactivity with endogenous epitopes, and by siRNA-mediated depletion of Ciz1 that specifically reduced 1793 nuclear staining.

Immunoprecipitation

Asynchronousy growing 3T3 cells were washed in PBS, rinsed in extraction buffer (20 mM Hepes pH7.8, 5 mM potassium acetate, 0.5 mM magnesium chloride) supplemented with EDTA-free protease inhibitor cocktail (Roche) and scrape harvested as for replication extracts. Cells were lysed with 0.1% Triton X 100 and the detergent resistant pellet fraction extracted with 0.3M NaCl in extraction buffer. 5 µl of 1793 or 2 µl of antibody V were used per 100 µl of extract and incubated for 1 hour at 4° C. Antigen-antibody complexes were extracted with 100 µl of protein G-sepharose (Sigma) and beads were washed five times with 50 mM Tris pH 7.8, 1 mM EDTA, 0.1% NP40, 150 mM NaCl. Complexes were boiled in loading buffer (100 mM DTT, 2% SDS, 60 mM Tris pH6.8, 0.001% bromophenol blue) and resolved by 6.5% SDS-polyacrylamide gel electrophoresis.

Immuno-Fluorescence

Cells were grown on coverslips and fixed in 4% paraformaldehyde, with or without brief pre-exposure to 0.05% Triton X100 in PBS. Endogenous Ciz1 was detected with 1793 serum diluted 1/2000 in antibody buffer following standard procedures. Mcm3 was detected with monoclonal antibody sc9850 (1/1000), Cdc6 with monoclonal sc9964 (1/100) and PCNA with monoclonal antibody PC10 (1/100, all Santa Cruz Biotechnology). Co-localization analysis of dual stained fluorescent confocal images was carried out as described (Rubbi and Milner, 2000; van Steensel et al., 1996).

Cell Synchrony

Mouse 3T3 cells were synchronized by release from quiescence as previously described (Coverley et al., 2002). Nuclei prepared from cells harvested 17 hours after release (referred to as 'late-G1') were used in all cell-free replication experiments described here. This yielded populations containing S phase nuclei, replication competent late G1 nuclei and unresponsive early G1/G0 nuclei, in varying proportions. Recipient, mid-G1 3T3 extracts were prepared at 15 hours (these typically contain approximately 5% S phase cells). The series of cell-free replication experiments described here required large amounts of standardized extract, therefore HeLa cells were used because they are easily synchronized in bulk. S phase HeLa extracts were prepared from cells released for two hours from two sequential thymidine-induced S phase blocks, as described (Krude et al., 1997).

Cell-Free DNA Replication

DNA replication assays were performed as described (Coverley et al., 2002; Krude et al., 1997). Briefly, 10 µl of mid G1 or S phase extract (supplemented with energy regenerating system, nucleotides and biotinylated dUTP), and $5\times10^4$ late G1 phase nuclei were incubated for 60 mins at 37° C. Reactions were supplemented with baculovirus lysate containing cyclin A-cdk2 (FIGS. 1 B and C), where 0.1 µl of lysate has the same specific activity as 1 nM purified kinase (Coverley et al., 2002). All recombinant proteins were serially diluted in 100 mM Hepes pH 7.8, 1 mM DTT, 50% glycerol, so that not more than 1 µl was added to 10 µl replication assays, generating the concentrations indicated. Reactions were stopped with 50 µl of 0.5% Triton X100 and fixed by the addition of 50 µl of 8% paraformaldehyde, for 5 minutes. After transfer to coverslips, nuclei were stained with streptavidin-FITC (Amersham) and counterstained with Toto-3-iodide (Molecular Probes). The proportion of labelled nuclei was quantified by inspection at 1000× magnification, and all nuclei with fluorescent foci or intense uniform labelling were scored positive. Images of in vitro replicating nuclei were generated by confocal microscopy at 600× magnifications, of samples counterstained with propidium iodide. For analysis of nuclear proteins, nuclei were re-isolated after 15 minutes exposure to initiating conditions, by diluting reactions two fold with cold PBS and gentle centrifugation.

Data Analysis and Presentation

Prior to use in initiation assays each preparation of synchronized G1 phase nuclei is tested so that the proportion of nuclei that are already in S phase is established ('% S'). To do this nuclei are incubated in an extract that is incapable of inducing initiation of DNA synthesis (from mid-G1 phase cells harvested 15 hours after release from quiescence), but that will efficiently support elongation DNA synthesis from origins that were initiated in vivo. The elongating fraction of nuclei incorporates labeled nucleotides efficiently during in vitro initiation assays but is uninformative. Routinely this fraction is pre-established and subtracted from the raw data. Synchronized populations in which 20% or less are in S phase are used for initiation assays.

When 3T3 cells are released from quiescence by the protocol used here no more than 70% of the total population enters S phase (Coverley et al., 2002). However, the highest observed replication frequency in vitro is nearer 50%; usually obtained by incubation with ECiz1. For the G1 population of 3T3 nuclei used here 17% were in S phase (% S) and the maximum number that replicated in any assay in vitro was 51% (% replication). Therefore, 34% of this population is competent to initiate replication in vitro (% C). Thus, for each data point in FIGS. 3B-F, % initiation=(% replication−% S)/% C×100.

RNA Interference

Endogenous Ciz1 was targeted in proliferating NIH3T3 cells using in vitro transcribed siRNAs (Ambion Silencer kit), directed against four regions of mouse Ciz1. Oligonucleotide sequences that were used to generate siRNAs are AAGCACAGTCACAGGAGCAGACCTGT (SEQ ID NO: 9) CTC and AATCTGCTCCTGTGACTGTGCCCTGTCTC (SEQ ID NO: 10) for siRNA 4, AATCTGTCACAAGTTC-TACGACCTGTCTC (SEQ ID NO: 11) and AATCGTA-GAACTTGTGACAGACCTGTCTC (SEQ ID NO: 12) for siRNA 8, AATCGCAAGGATCTTCTTCTCCTGTCTC (SEQ ID NO:13) and AAAGAAGAAGAATCCTGCGAC-CTGTCTC (SEQ ID NO:14) for siRNA 9, and AATCT-GCAGCAGTTCTTCCCCCTGTCTC (SEQ ID NO: 15) and AAGGGAAAGAACTGCTGCAGACCTGTCTC (SEQ ID NO: 16) for siRNA 11. Target sequences that are distributed throughout the Ciz1 transcript were chosen based on low secondary structure predictions and on location within exons that are consistently expressed in all known forms of Ciz1 (sequences 4, 8, 11), with the exception of one (siRNA 9) that is known to be alternatively spliced. Negative controls were untreated, mock treated (transfection reagents but no siRNA) and cells treated with GAPDH siRNA (Ambion). Cy3 labelled siRNAs (Ambion) were used to estimate transfection efficiency, which was found to be greater than 95%. RNA interference experiments were performed in 24 well format starting with $2 \times 10^4$ cells per well in 500 µl of medium (DMEM with glutamax supplemented with 4% FCS). siRNA's were added 12 hours after plating using oligofectamine reagent for delivery (Invitrogen). Unless stated otherwise, siRNAs were used in pairs (at 2 nM total concentration in medium), as two doses with the second dose delivered in fresh medium 24 hours after the first. Results were assessed at 48 hours after first exposure, by counting cell number, S phase labelling, and immunostaining. Northern blots were performed on RNAs isolated from cells treated for 24 hours with a single dose of siRNA, in reactions that were scaled up 5 fold. RNA was prepared using Trizol Reagent (Invitrogen) and samples were electrophoresed through 1% agarose, transferred onto Hybond N+ nylon membrane (Amersham), and sequentially hybridized at 50° C. with cDNA probes using NorthernMax kit reagents (Ambion), following manufacturers instructions. The membrane was stripped between each hybridization using 0.5% SDS solution at 90° C., allowed to cool slowly to room temperature. Probes were [$^{32}$P]-dCTP labelled using Random Primers DNA labelling system (Gibco BRL), and used in the following order: i. A 1.35 kb XmaI-XhoI fragment derived from ECiz1. ii. Human β-actin cDNA (Clontech) and iii. Mouse GAPDH cDNA (RNWAY laboratories). The membrane was washed twice in 2×SSC 0.2% SDS for 30-60 mins each, followed by one wash in 0.2×SSC 0.2% SDS for 30 mins, at 55-65° C., depending on probe used. Hybridization signals were quantified using an Amersham Biosciences Typhoon 9410 variable mode imager, and Image Quant TL software (v2002). Band intensities are expressed in arbitrary units (in parentheses), and results for Ciz1 and GAPDH were normalized against those for β-actin, and expressed as a %.

S Phase Labelling

The fraction of nuclei undergoing DNA synthesis in vivo was monitored by supplementing culture medium with 20 µM bromodeoxyuridine (BrdU, Sigma) for 20 minutes. Incorporated BrdU was visualized after acid treatment with FITC-conjugated anti-BrdU monoclonal antibody (Alexis Biochemicals) according to manufacturers instructions. Nuclei were counterstained with Hoescht 33258 and scored under high (1000×) magnification.

Green Fluorescent Protein Tagged Ciz1

Full-length mouse Ciz1 cDNA was obtained from UK HGMP Resource Centre (MGC clone 27988) and the sequence fully verified. A 2.8 kb SmaI-XbaI (blunt ended) full length Ciz1 fragment from this clone, and a 2.3 kb SmaI-XbaI (blunt ended) ECiz1 fragment from pTriplEx-clone L were ligated in frame with enhanced green fluorescent protein (EGFP) into the SmaI site of pEGFP-C3 (Clontech). pEGFP-C3 with no insert was used as a control. Constructs were transfected into NIH3T3 cells using TransIT-293 (Mirus), following manufacturers instructions or microinjected into the male pro-nucleus of fertilized mouse eggs at the one cell stage. Growing 3T3 cells transfected with full length EGFP-Ciz1, or EGFP-ECiz1 were analysed by live cell fluorescent microscopy up to three days after transfection. DNA synthesis was monitored during the first 24 hours after transfection, by including the nucleotide analogue BrdU in cell culture medium for various time periods as indicated in figure legends. As described above any cells undergoing DNA synthesis while exposed to BrdU stain with anti-BrdU monoclonal antibody generating red nuclei. Ciz1 transfected cells were also maintained under selection with 50 µg/ml G418, in standard culture medium (DMEM Glutamax plus 10% fetal calf serum) for up to a month, yielding cell populations with altered morphology.

EST Sequence Analysis

Individual expressed sequence tags (ESTs) mapping to NCBI unigene cluster Hs.23476 (human Ciz1) were translated using Genejockey and the predicted amino-acid sequence compared to the predicted sequence for full length Ciz1, with the aim of identifying recurrent changes in cancer cells. In order to exclude errors that reflect poor quality DNA sequence such as that which occurs at the end of long sequencing runs, only those changes positioned more than 8 amino-acids from the end of uninterrupted sequence are included in this analysis. Frame-shifts that are restored by a second alteration later in the read, and frame-shifts that are followed by a stop codon are only included if followed by uninterrupted sequence. Thus the majority of sequencing errors are excluded from this analysis. However, it is expected that many of the point mutations that remain (including frame-shifts and stops) reflect errors introduced during sequencing. Therefore, this analysis is aimed at uncovering trends, with weight being given to point mutations only if they appear more than once.

Of 567 sequences that map to Ciz1 unigene cluster, we have analyzed most (all paediatric cancers, prostate and lung carcinomas, leukemias and lymphomas and a wide range of non-diseased tissues). Some were not mapped because they are extremely short reads or yielded very short amino-acid sequences upon translation, and for a small number we detected no homology to the Ciz1 coding sequence. A small number of ESTs were excluded from the analysis because of multiple frameshifts that produced stretches of homology in all three frames, with no indication of the reading frame used in vivo. These were all from cancer derived material, usually adenocarcinomas.

RT-PCR Analysis of Ciz1 Isoform Expression

RNA was isolated using trizol reagent following recommended procedures, DNAse treated and reverse transcribed using random hexamers and superscript II, then amplified with Ciz1 specific primers:

```
h/m5
                                        (SEQ ID NO: 17)
CAGTCCCCACCACAGGCC, h/m2
                                        (SEQ ID NO: 18)
GGCTTCCTCAGACCCCTCTG.

H/m3
                                        (SEQ ID NO: 19)
ACACAGACCTCTCCAGAGCACTTAG

H/m4
                                        (SEQ ID NO: 20)
ATGGTGACCTTCAGGGAGC

H4
                                        (SEQ ID NO: 21)
TCCTTGGCGA TGTCCTCTGG GCAGG

H3
                                        (SEQ ID NO: 22)
TCCCTCCTCA ACGGCTCCAT GCTGC

H6
                                        (SEQ ID NO: 23)
CG TGGGGGCGAC TTGAGCGTTG AGG
```

-continued

H1
(SEQ ID NO: 24)
GATGCCAGGGGT ATGGGCGCC GGG

H2
(SEQ ID NO: 25)
TCCGAGCCCT TCCACTCCTC TCTGG.

Analysis of Ciz1 Protein Isoforms in Cancer Cell Lines

Cells were grown in DMEM with 10% FCS until subconfluent, rinsed in cold hepes buffered saline supplemented with EDTA free protease inhibitor cocktail (Roche) then scrape harvested and supplemented with 0.1% Triton X100. Detergent-insoluble material (including nuclei) was pelleted by gentle centrifugation to yield supernatant (SN) and pellet fractions (P). These were boiled in reducing SDS-PAGE sample buffer and proteins resolved by electrophoresis through 8% SDS-PAGE. After transfer to nitrocellulose, Ciz1 isoforms were detected with anti-Ciz1 antibody 1793). All methods used in this analysis are well documented elsewhere.

REFERENCES

Bell, S. P. and Dutta, A. (2002). DNA replication in eukaryotic cells. *Annu Rev Biochem* 71, 333-74.
Cook, P. R. (1999). The organization of replication and transcription. *Science* 284, 1790-5.
Corpet, F. (1998). Multiple sequence alignment with hierarchical clustering. *Nucl. Acids Res.* 16, 10881-10890.
Coverley, D., Laman, H. and Laskey, R. A. (2002). Distinct roles for cyclins E and A during DNA replication complex assembly and activation. *Nat Cell Biol* 4, 523-8.
Coverley, D., Pelizon, C., Trewick, S. and Laskey, R. A. (2000). Chromatin bound Cdc6 persists in S and G2 phases in human cells, while soluble Cdc6 is destroyed in a cyclin A-cdk2 dependent process. *J. Cell Sci.* 113, 1929-1938.
Fujita, M. (1999). Cell cycle regulation of DNA replication initiation proteins in mammalian cells. *Front Biosci* 4, D816-23.
Hanahan, D. and Weinberg, R. A. (2000). The Hallmarks of Cancer. *Cell* 100, 57-70.
Harlow, E. and Lane, D. (1988). Antibodies: A laboratory manual. New York: Cold Spring Harbour Laboratory Press.
Jones, D. L., Alani, R. M. and Munger, K. (1997). The human papillomavirus E7 oncoprotein can uncouple cellular differentiation and proliferation in human keratinocytes by abrogating p21Cip1-mediated inhibition of cdk2. *Genes Dev.* 11, 2101-2111.
Krude, T. (2000). Initiation of human DNA replication in vitro using nuclei from cells arrested at an initiation-competent state. *J. Biol. Chem.* 275, 13699-13707.
Krude, T., Jackman, M., Pines, J. and Laskey, R. A. (1997). Cyclin/Cdk-dependent initiation of DNA replication in a human cell-free system. *Cell* 88, 109-119.
Laman, H., Coverley, D., Krude, T. K., Laskey, R. A. and Jones, N. (2001). Viral cyclin/cdk6 complexes initiate nuclear DNA replication. *Mol. Cell. Biol.* 2, 624-635.
Mercatante, D. R. and Kole, R. (2002). Control of alternative splicing by antisense oligonucleotides as a potential chemotherapy: effects on gene expression. *Biochim Biophys Acta* 1587, 126-32.
Mitsui, K., Matsumoto, A., Ohtsuka, S., Ohtsubo, M. and Yoshimura, A. (1999). Cloning and characterization of a novel p21cip1/waf1-interacting zinc finger protein, Ciz1. *Biochem. Biophys. Res. Com.* 264, 457-464.
Nakayasu, H. and Berezney, R. (1991). Nuclear matrins: identification of the major nuclear matrix proteins. *Proc Natl Acad Sci USA* 88, 10312-6.
Ohnuma, S., Philpott, A. and Harris, W. A. (2001). Cell cycle and cell fate in the nervous system. *Curr Opin Neurobiol* 11, 66-73.
Parker, S. B., Eichele, G., Zhang, P., Rawls, A., Sands, A. T., Bradley, A., Olson, E. N., Harper, J. W. and Elledge, S. J. (1995). p53-independent expression of p21Cip1 in muscle and other terminally differentiating cells. *Science* 267, 1024-7.
Rubbi, C. P. and Milner, J. (2000). Non-activated p53 co-localizes with sites of transcription within both the nucleoplasm and the nucleolus. *Oncogene* 19, 85-96.
Sherr, C. J. and Roberts, J. M. (1999). CDK inhibitors: positive and negative regulators of G1-phase progression. *Genes Dev.* 13, 1501-1512.
Stoeber, K., Mills, A. D., Kubota, Y., Krude, T., Romanowski, P., Marheineke, K., Laskey, R. A. and Williams, G. H. (1998). Cdc6 protein causes premature entry into S phase in a mammalian cell-free system. *EMBO J.* 17, 7219-7229.
van Steensel, B., van Binnendijk, E. P., Hornsby, C. D., van der Voort, H. T., Krozowski, Z. S., de Kloet, E. R. and van Driel, R. (1996). Partial colocalization of glucocorticoid and mineralocorticoid receptors in discrete compartments in nuclei of rat hippocampus neurons. *J Cell Sci* 109 (Pt 4), 787-92.
Warder, D. E. and Keherly, M. J. (2003). Ciz1, Cip1 interacting zinc finger protein 1 binds the consensus DNA sequence ARYSR(0-2)YYAC. *J Biomed Sci* 10, 406-17.
Williams, G. H., Romanowski, P., Morris, L., Madine, M., Mills, A. D., Stoeber, K., Marr, J., Laskey, R. A. and Coleman, N. (1998). Improved cervical smear assessment using antibodies against proteins that regulate DNA replication. *Proc. Natl. Acad. Sci. USA* 95, 14932-14937.
Zezula, J., Casaccia-Bonnefil, P., Ezhevsky, S. A., Osterhout, D. J., Levine, J. M., Dowdy, S. F., Chao, M. V. and Koff, A. (2001). p21cip1 is required for the differentiation of oligodendrocytes independently of cell cycle withdrawal. *EMBO Rep* 2, 27-34.

I claim:

1. A method for determining whether a subject has cancer, the method comprising:

a) providing a biological sample from the subject;

b) contacting the biological sample with an antibody that specifically binds to a Ciz1 splice variant which lacks the sequence VEEELCKQ (SEQ ID NO: 3), thereby forming a Ciz1 splice variant-antibody complex;

c) detecting the complexes and thereby measuring the protein expression level of the Ciz1 splice variant in the sample; and d) comparing the protein expression level of the Ciz1 splice variant in the sample with the protein expression level of the Ciz1 splice variant in a control sample, wherein an elevated protein expression level of the Ciz1 splice variant indicates an increased likelihood that the subject has cancer.

2. The method of claim 1, wherein the antibody comprises a polyclonal antibody.

3. The method of claim 1, wherein the antibody comprises a monoclonal antibody.

4. The method of claim 1, wherein the Ciz1 splice variant comprises the amino-acid sequence of SEQ ID NO: 64.

5. The method of claim 1, wherein the cancer is a pediatric cancer selected from the group consisting of retinoblastoma, neuroblastoma, Burkett lymphoma, medulloblastoma, and Ewings Sarcoma family tumors.

6. The method of claim 1, wherein the cancer is carcinoma, adenocarcinoma, lymphoma or leukemia.

7. The method of claim 1, wherein the cancer is liver, lung or skin cancer.

8. The method of claim 1, wherein detecting the complexes comprises an immunosorbent assay, immunofluorimetry, or immunoprecipitation.

9. A method of detecting a Ciz1 splice variant in a subject, wherein the Ciz1 splice variant lacks the sequence VEEELCKQ (SEQ ID NO: 3), the method comprising:

a) contacting a biological sample from the subject with an antibody against the Ciz1 splice variant; and b) detecting binding between the Ciz1 splice variant and the antibody, thereby detecting the Ciz1 splice variant.

10. The method of claim 9, wherein the antibody comprises a polyclonal antibody.

11. The method of claim 9, wherein the antibody comprises a monoclonal antibody.

12. The method of claim 9, wherein the Ciz1 splice variant comprises the amino acid sequence of SEQ ID NO: 64.

13. The method of claim 9, wherein detecting binding between the Ciz1 splice variant and the antibody comprises an immunosorbent assay, immunofluorimetry, or immunoprecipitation.

* * * * *